United States Patent
Ruggero et al.

(10) Patent No.: US 9,765,337 B2
(45) Date of Patent: Sep. 19, 2017

(54) PHOSPHORIBOSYL PYROPHOSPHATE SYNTHETASE 2 (PRPS2) AS A THERAPEUTIC TARGET IN CANCER TREATMENT

(71) Applicant: THE REGENTS OF THE UNIVERSITY OF CALIFORNIA, Oakland, CA (US)

(72) Inventors: Davide Ruggero, San Francisco, CA (US); John Thomas Cunningham, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/760,690

(22) PCT Filed: Jan. 22, 2014

(86) PCT No.: PCT/US2014/012552
§ 371 (c)(1),
(2) Date: Jul. 13, 2015

(87) PCT Pub. No.: WO2014/116704
PCT Pub. Date: Jul. 31, 2014

(65) Prior Publication Data
US 2015/0337316 A1 Nov. 26, 2015

Related U.S. Application Data

(60) Provisional application No. 61/755,392, filed on Jan. 22, 2013.

(51) Int. Cl.
| | | |
|---|---|---|
| C07H 21/02 | (2006.01) |
| C07H 21/04 | (2006.01) |
| A61K 48/00 | (2006.01) |
| C12N 15/113 | (2010.01) |
| G01N 33/50 | (2006.01) |

(52) U.S. Cl.
CPC ...... *C12N 15/1137* (2013.01); *G01N 33/5011* (2013.01); *C12N 2310/14* (2013.01); *C12N 2310/531* (2013.01); *C12N 2320/30* (2013.01); *G01N 2333/91142* (2013.01)

(58) Field of Classification Search
CPC .... C12N 15/113; C12N 2310/11; A61K 48/00
See application file for complete search history.

(56) References Cited

FOREIGN PATENT DOCUMENTS

| CN | 103333893 A | 10/2013 |
| CN | 103343125 A | 10/2013 |
| WO | 2008026946 A2 | 3/2008 |

OTHER PUBLICATIONS

Clohessy et al. (Cell Research, 2012, 22, 1315-1318).*
Anonymous: "Martin Lukas Sos, MD, University of California, San Francisco: "Targeting MYC-dependent etabolism in prostate cancer,"" The 2012 Drew Foundation—PCF Young Investigator Award, 2012, retrieved on Apr. 22, 2014 from the Internet: http://www.pcf.org/site/c.LeJRIROrEpH/b.7966905/k.B60C/Young_Investigator_Award_Recipients_2012.htm.
Anonymous: "Young Investigator Award Recipients 2012—Prostate Cancer Foundation (PCF)," retrieved on Apr. 22, 2014 from the Internet: http://www.pcf.org/site/c.leJRIROrEpH/b.7966905/k.B60C/Young_Investigator_Award_Recipients_2012.htm.
Barna et al., "Suppression of Myc oncogenic activity by ribosomal protein haploinsufficiency," 2008, Nature 456:971-975.
Becker, "Phosphoribosylpyrophosphate synthetase and the regulation of phosphoribosylpyrophosphate production in human cells," Prog Nucleic Acid Res Mol Biol 69:115-48 (2001).
Ben-Sahra et al., "Stimulation of de Novo Pyrimidine Synthesis by Growth Signaling Through mTOR and S6K1," 2013, Science 339:1323-1328.
Hsieh et al., "Genetic Dissection of the Oncogenic mTOR Pathway Reveals Druggable Addiction to Translational Control via 4EBP-eIF4E ," 2010, Cancer Cell 17:249-261.
Hsieh et al., "The translational landscape of mTOR signalling steers cancer initiation and metastasis," 2012, Nature 485:55-61.
Mannava, Sudha et al., "Direct role of nucleotide metabolism in C-MYC-dependent proliferation of melanoma cells," Cell Cycle, vol. 7, No. 15, Aug. 1, 2009, pp. 2392-2400.
Nikiforov, Mikhail A. et al., "Abstract #1682: c-MYC directly regulates nucleotide metabolism," AACR, Proceedings of the Annual Meeting, 99th Annual Meeting of the AACR, vol. 49, Apr. 2008, p. 396.
Schlabach, MR et al., "Cancer Proleferation Gene Discovery Through Functional Genomics," Science, vol. 319, No. 5863, Feb. 1, 2008, pp. 620-624.
Seiden-Long, IM et al., "Transcriptional targets of hepatocyte growth factor signaling and Ki-ras oncogene activation in colorectal cancer," Oncogene, vol. 25, No. 1, Sep. 12, 2005, pp. 91-102.

* cited by examiner

*Primary Examiner* — Amy Bowman
(74) *Attorney, Agent, or Firm* — Kilpatrick Townsend Stockton LLP

(57) ABSTRACT

The present invention provides methods of selectively killing a cell, comprising contacting the cell with an agent that inhibits phospho-ribosyl pyrophosphate synthetase 2 (PRPS2). The present invention also provides methods of identifying a candidate agent that selectively kills neoplastic cells that are Myc-hyperactivated via inhibition of PRPS2.

19 Claims, 42 Drawing Sheets

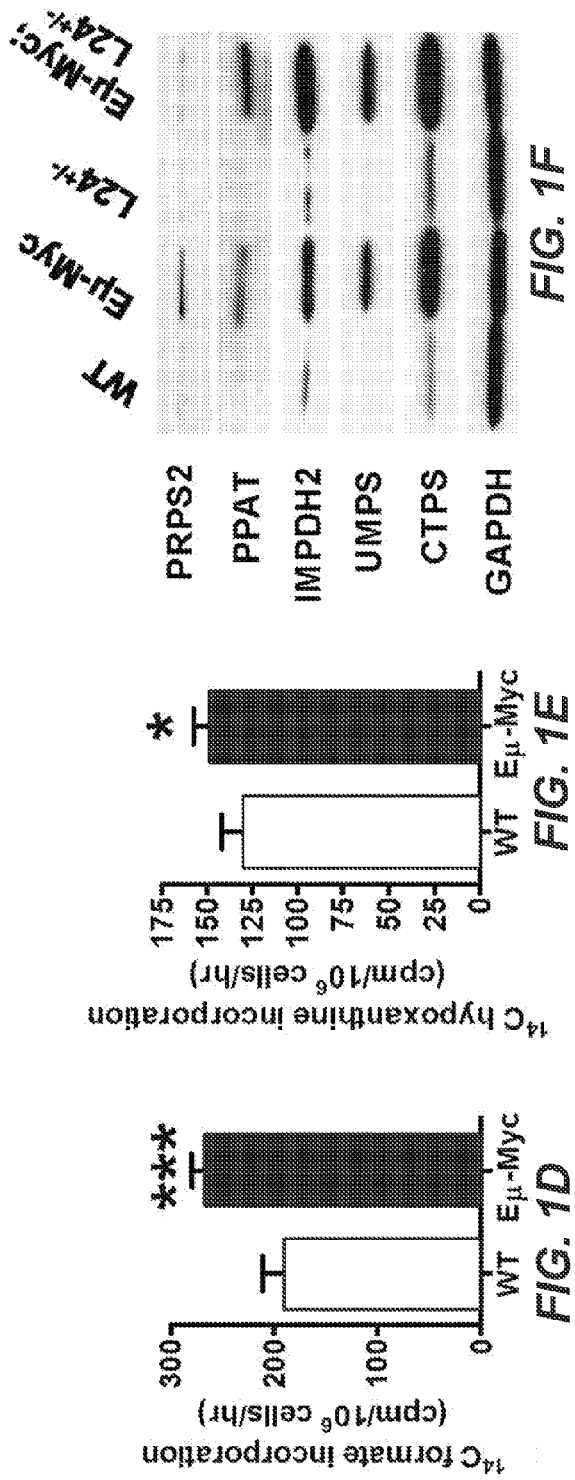
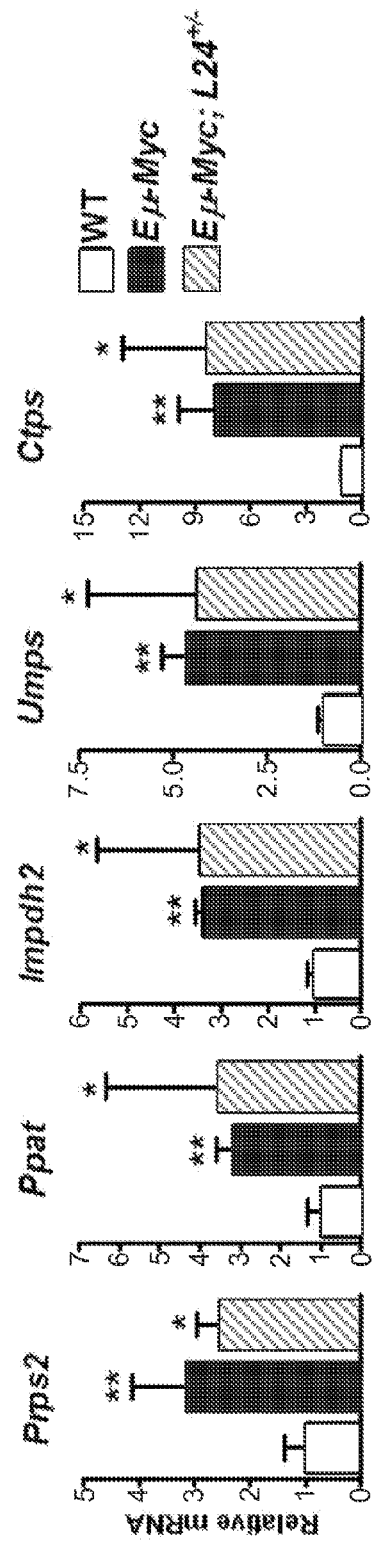

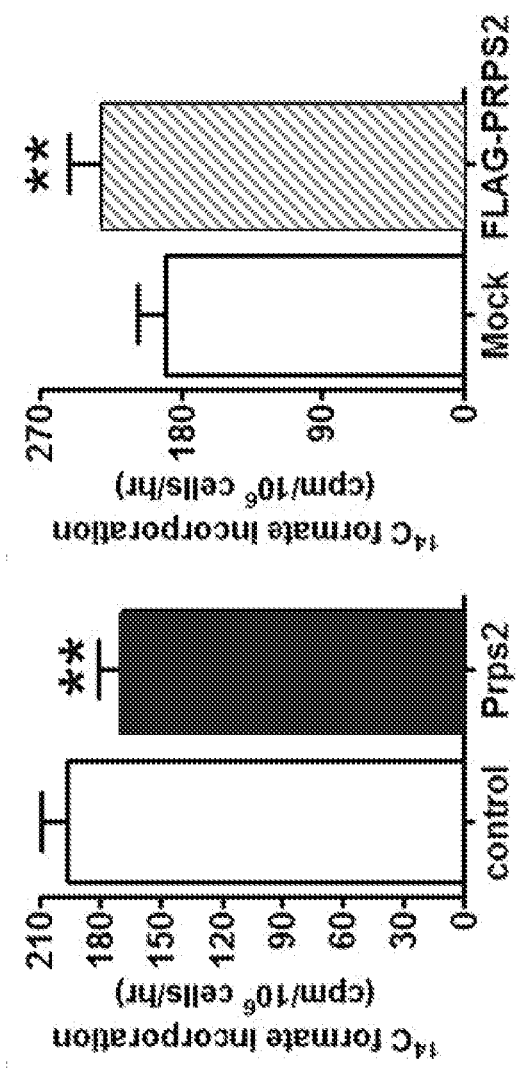

-108    Mus *Prps2* mRNA (TSS through first codon)

AGCCCAGGCCACCGCAGCAGCAGCAACAGCCGCAGCAACGGU
AGCAGUAGUCUGCAUCGCAGUCCCUUCUUCCAGCGCGCU
CCUCAGUCCCCGGUCACCAUG [SEQ ID NO: 1]
-1

-140    Mus *Prps1* mRNA (TSS through first codon)

GCCGGCGGCUGGGGCGGGAAUGAAGAUGGCGGAGUAGCAACGCGG
UACUGUUGGGUUCAGAGACUGCCUGACUUCCGUCCGUGUUGG
CAGCGGGCGGGCGGGCGGACCACUGAGCACGUUGAGGUAGUUACCA
AGAUG [SEQ ID NO: 2]
-1

*FIG. 7A*

-143  Human *Prps2* mRNA
ucucuccccucCGcucccuCCcuACAUCUAGCCGCCGCGCUUCCCG
CUCCCGCAGCAGCCUCCGGCGUCGCUGUGCUGUUGCUCCGCACCUC
CUCCGGCGGCCGCCUCCGGAGUUCCGCCCCACCAUG [SEQ ID NO:35]
−1

-87  Human *Prps1* mRNA
AGCUAAUCGUUGCCAGGGGUGGUGGACUUGCCGCUGACCCCUCCGC
CGCUUUGGGUAAUUUAGAGCCGCCGGGCGGCCUUGGGAAUG [SEQ ID NO:36]
−1

FIG. 7B

SEQUENCE LISTING

```
<160> NUMBER OF SEQ ID NOS: 40

<210> SEQ ID NO 1
<211> LENGTH: 111
<212> TYPE: RNA
<213> ORGANISM: Artificial Sequence
<220> FEATURE:
<223> OTHER INFORMATION: synthetic mouse phosphoribosyl pyrophosphate
      synthetase 2 (PRPS2) 5' untranslated region
      (5'UTR) TSS through first codon
<220> FEATURE:
<221> NAME/KEY: misc_feature
<222> LOCATION: (66)...(82)
<223> OTHER INFORMATION: pyrimidine-rich translational element (PRTE),
      consensus PRTE motif
```

```
<400> SEQUENCE: 1
agcccaggcc accgcagcag cagcagcaac agccgcagca acgguagcag uagucugcau        60
cgcagucccu uucuccuucu ccagcgcgcu ccucaguccc cggucaccau g                111

<210> SEQ ID NO 2
<211> LENGTH: 142
<212> TYPE: RNA
<213> ORGANISM: Artificial Sequence
<220> FEATURE:
<223> OTHER INFORMATION: synthetic mouse phosphoribosyl pyrophosphate
      synthetase 1 (PRPS1) 5' untranslated region
      (5'UTR) TSS through first codon

<400> SEQUENCE: 2
gccgcgcgcu gggcgggaau guaagauggc ggaguagcaa cgcgguacug uuggguguuca      60 gacugccugc ugacuuccgu ucccguguug gcagcggcgg cggcggcgac cacugagcac      120
guugagguag uuacccaaga ug                                               142

<210> SEQ ID NO 3
<211> LENGTH: 17
<212> TYPE: RNA
<213> ORGANISM: Artificial Sequence
<220> FEATURE:
<223> OTHER INFORMATION: synthetic pyrimidine-rich translational element
      (PRTE), consensus PRTE motif

<400> SEQUENCE: 3
ucccuuucuc cuucucc                                                      17

<210> SEQ ID NO 4
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      beta-actin forward primer

<400> SEQUENCE: 4
gacatggaga agatctggca                                                   20

<210> SEQ ID NO 5
<211> LENGTH: 21
<212> TYPE: DNA
<213> ORGANISM: Artificial Sequence
<220> FEATURE:
<223> OTHER INFORMATION: synthetic quantitative real-time PCR (qRT-PCR)
      beta-actin reverse primer

<400> SEQUENCE: 5
ggtctcaaac atgatctggg t                                                 21

<210> SEQ ID NO 6
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      Prps2 forward primer

<400> SEQUENCE: 6
atgaagtgga ccggatggtt                                                   20

<210> SEQ ID NO 7
<211> LENGTH: 20
```

```
<212> TYPE: DNA
<213> ORGANISM: Artificial Sequence
<220> FEATURE:
<223> OTHER INFORMATION: synthetic quantitative real-time PCR (qRT-PCR)
      Prps2 reverse primer

<400> SEQUENCE: 7
ggtggcacca gctgagagta                                                      20

<210> SEQ ID NO 8
<211> LENGTH: 21
<212> TYPE: DNA
<213> ORGANISM: Artificial Sequence
<220> FEATURE:
<223> OTHER INFORMATION: synthetic quantitative real-time PCR (qRT-PCR)
      Ppat forward primer

<400> SEQUENCE: 8
aggaatgtgg tgtgtttggg t                                                    21

<210> SEQ ID NO 9
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      Ppat reverse primer

<400> SEQUENCE: 9
caataccagc gctctcctga                                                      20

<210> SEQ ID NO 10
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      Umps forward primer

<400> SEQUENCE: 10
ccaatcacat tcccatgctc                                                      20

<210> SEQ ID NO 11
<211> LENGTH: 18
<212> TYPE: DNA
<213> ORGANISM: Artificial Sequence
<220> FEATURE:
<223> OTHER INFORMATION: synthetic quantitative real-time PCR (qRT-PCR)
      Umps reverse primer

<400> SEQUENCE: 11
aacactggct ccgctggt                                                        18

<210> SEQ ID NO 12
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      Ctps forward primer

<400> SEQUENCE: 12
gtgtgcaggt gctcaaatcc                                                      20

<210> SEQ ID NO 13
<211> LENGTH: 20
<212> TYPE: DNA
```

```
<213> ORGANISM: Artificial Sequence
<220> FEATURE:
<223> OTHER INFORMATION: synthetic quantitative real-time PCR (qRT-PCR)
      Ctps reverse primer

<400> SEQUENCE: 13
caagggtacc cggtagatgg                                                  20

<210> SEQ ID NO 14
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      Impdh2 forward primer

<400> SEQUENCE: 14
cgcaagccaa gaacctcata                                                  20

<210> SEQ ID NO 15
<211> LENGTH: 19
<212> TYPE: DNA
<213> ORGANISM: Artificial Sequence
<220> FEATURE:
<223> OTHER INFORMATION: synthetic quantitative real-time PCR (qRT-PCR)
      Impdh2 reverse primer

<400> SEQUENCE: 15
aagcgacggg catactcag                                                   19

<210> SEQ ID NO 16
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      Atic forward primer

<400> SEQUENCE: 16
tatgtgaccg gcactatcgg                                                  20

<210> SEQ ID NO 17
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      Atic reverse primer

<400> SEQUENCE: 17
gcttgtccac ccattccttc                                                  20

<210> SEQ ID NO 18
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      Prps1 forward primer

<400> SEQUENCE: 18
cctgccattt ctcgaatcaa                                                  20

<210> SEQ ID NO 19
<211> LENGTH: 20
<212> TYPE: DNA
<213> ORGANISM: Artificial Sequence
```

```
<220> FEATURE:
<223> OTHER INFORMATION: synthetic quantitative real-time PCR (qRT-PCR)
      Prps1 forward primer

<400> SEQUENCE: 19
gtgggttctc ctgatggctt                                              20

<210> SEQ ID NO 20
<211> LENGTH: 26
<212> TYPE: DNA
<213> ORGANISM: Artificial Sequence
<220> FEATURE:
<223> OTHER INFORMATION: synthetic quantitative real-time PCR (qRT-PCR)
      Rplp0 forward primer

<400> SEQUENCE: 20
gcagacaacg tgggctccaa gcagat                                       26

<210> SEQ ID NO 21
<211> LENGTH: 26
<212> TYPE: DNA
<213> ORGANISM: Artificial Sequence
<220> FEATURE:
<223> OTHER INFORMATION: synthetic quantitative real-time PCR (qRT-PCR)
      Rplp0 reverse primer

<400> SEQUENCE: 21
ggtcctcctt ggtgaacacg aagccc                                       26

<210> SEQ ID NO 22
<211> LENGTH: 40
<212> TYPE: DNA
<213> ORGANISM: Artificial Sequence
<220> FEATURE:
<223> OTHER INFORMATION: synthetic Prps2 5'UTR PRTE site-directed
      mutagenesis forward deltaPRTE oligonucleotide

<400> SEQUENCE: 22
cggtagcagt agtctgcatc gcagagcgcg ctcctcagtc                        40

<210> SEQ ID NO 23
<211> LENGTH: 40
<212> TYPE: DNA
<213> ORGANISM: Artificial Sequence
<220> FEATURE:
<223> OTHER INFORMATION: synthetic Prps2 5'UTR PRTE site-directed
      mutagenesis reverse deltaPRTE oligonucleotide

<400> SEQUENCE: 23
gactgaggag cgcgctctgc gatgcagact actgctaccg                        40

<210> SEQ ID NO 24
<211> LENGTH: 57
<212> TYPE: DNA
<213> ORGANISM: Artificial Sequence
<220> FEATURE:
<223> OTHER INFORMATION: synthetic Prps2 5'UTR PRTE site-directed
      mutagenesis forward PRTE transversion oligonucleotide

<400> SEQUENCE: 24
cggtagcagt agtctgcatc gcagagggaa agaggaagag gagcgcgctc ctcagtc     57

<210> SEQ ID NO 25
<211> LENGTH: 57
<212> TYPE: DNA
<213> ORGANISM: Artificial Sequence
<220> FEATURE:
```

```
<223> OTHER INFORMATION: synthetic Prps2 5'UTR PRTE site-directed
      mutagenesis reverse PRTE transversion oligonucleotide

<400> SEQUENCE: 25
gactgaggag cgcgctcctc ttcctctttc cctctgcgat gcagactact gctaccg        57

<210> SEQ ID NO 26
<211> LENGTH: 21
<212> TYPE: DNA
<213> ORGANISM: Artificial Sequence
<220> FEATURE:
<223> OTHER INFORMATION: synthetic control non-targeting shRNA oligo

<400> SEQUENCE: 26
caacaagatg aagagcacca a                                                21

<210> SEQ ID NO 27
<211> LENGTH: 21
<212> TYPE: DNA
<213> ORGANISM: Artificial Sequence
<220> FEATURE:
<223> OTHER INFORMATION: synthetic mouse Prps2 shRNA target sequence
      oligo, inhibitory RNA

<400> SEQUENCE: 27
gtggttattt ggtcgttaat t                                                21

<210> SEQ ID NO 28
<211> LENGTH: 22
<212> TYPE: DNA
<213> ORGANISM: Artificial Sequence
<220> FEATURE:
<223> OTHER INFORMATION: synthetic human PRPS2 shRNA target sequence
      oligo, inhibitory RNA

<400> SEQUENCE: 28
tgcagtgctt gtattggttt aa                                               22

<210> SEQ ID NO 29
<211> LENGTH: 19
<212> TYPE: DNA
<213> ORGANISM: Artificial Sequence
<220> FEATURE:
<223> OTHER INFORMATION: synthetic quantitative real-time PCR (qRT-PCR)
      5S rRNA forward primer

<400> SEQUENCE: 29
gcccgatctc gtctgatct                                                   19

<210> SEQ ID NO 30
<211> LENGTH: 20
<212> TYPE: DNA
<213> ORGANISM: Artificial Sequence
<220> FEATURE:
<223> OTHER INFORMATION: synthetic quantitative real-time PCR (qRT-PCR)
      5S rRNA reverse primer

<400> SEQUENCE: 30
agcctacagc acccggtatt                                                  20

<210> SEQ ID NO 31
<211> LENGTH: 25
<212> TYPE: DNA
<213> ORGANISM: Artificial Sequence
<220> FEATURE:
<223> OTHER INFORMATION: synthetic mutant allele genotyping forward
      primer
```

<400> SEQUENCE: 31
acattgccat aaggaattat cagag                                              25

<210> SEQ ID NO 32
<211> LENGTH: 16
<212> TYPE: DNA
<213> ORGANISM: Artificial Sequence
<220> FEATURE:
<223> OTHER INFORMATION: synthetic mutant allele genotyping reverse
      primer

<400> SEQUENCE: 32
ggcgccagcc tgcttt                                                        16

<210> SEQ ID NO 33
<211> LENGTH: 19
<212> TYPE: DNA
<213> ORGANISM: Artificial Sequence
<220> FEATURE:
<223> OTHER INFORMATION: synthetic wild-type allele genotyping forward
      primer

<400> SEQUENCE: 33
tgccagttat caccgctca                                                     19

<210> SEQ ID NO 34
<211> LENGTH: 20
<212> TYPE: DNA
<213> ORGANISM: Artificial Sequence
<220> FEATURE:
<223> OTHER INFORMATION: synthetic wild-type allele genotyping reverse
      primer

<400> SEQUENCE: 34
gctgcccaca cttcactctt                                                    20

<210> SEQ ID NO 35
<211> LENGTH: 146
<212> TYPE: RNA
<213> ORGANISM: Artificial Sequence
<220> FEATURE:
<223> OTHER INFORMATION: synthetic human phosphoribosyl pyrophosphate
      synthetase 2 (PRPS2) 5' untranslated region (5'UTR)
<220> FEATURE:
<221> NAME/KEY: misc_feature
<222> LOCATION: (18)...(28)
<223> OTHER INFORMATION: pyrimidine-rich translational element (PRTE)
<220> FEATURE:
<221> NAME/KEY: misc_feature
<222> LOCATION: (92)...(108)
<223> OTHER INFORMATION: pyrimidine-rich translational element (PRTE)

<400> SEQUENCE: 35 uccuccccu ccgcuccucc ccuucccuac aucuagccgc cgcgcuuucc cgcucccgca         60
gcagcagccu cccgcgucgc ugucgcuguu gccuccgcca ccuccuccgc cgccgcgcgc        120
cccucggagu uccgcgcccc accaug                                             146

<210> SEQ ID NO 36
<211> LENGTH: 90
<212> TYPE: RNA
<213> ORGANISM: Artificial Sequence
<220> FEATURE:
<223> OTHER INFORMATION: synthetic human phosphoribosyl pyrophosphate
      synthetase 1 (PRPS1) 5' untranslated region
      (5'UTR)

```
<400> SEQUENCE: 36
agcuaaucgu ugccagcggg guguggacuu cgccgcugac cccaccuccg ccgcuuuggg    60
uaauuuagag ccgcgcgccg ggcgggaaug                                     90

<210> SEQ ID NO 37
<211> LENGTH: 11
<212> TYPE: RNA
<213> ORGANISM: Artificial Sequence
<220> FEATURE:
<223> OTHER INFORMATION: synthetic human phosphoribosyl pyrophosphate
      synthetase 2 (PRPS2) 5' untranslated region
      (5'UTR) pyrimidine-rich translational element (PRTE)

<400> SEQUENCE: 37
uccccuuccc u                                                         11

<210> SEQ ID NO 38
<211> LENGTH: 17
<212> TYPE: RNA
<213> ORGANISM: Artificial Sequence
<220> FEATURE:
<223> OTHER INFORMATION: synthetic human phosphoribosyl pyrophosphate
      synthetase 2 (PRPS2) 5' untranslated region
      (5'UTR) pyrimidine-rich translational element (PRTE)

<400> SEQUENCE: 38
ccuccgccac cuccucc                                                   17

<210> SEQ ID NO 39
<211> LENGTH: 12
<212> TYPE: RNA
<213> ORGANISM: Artificial Sequence
<220> FEATURE:
<223> OTHER INFORMATION: synthetic human phosphoribosyl pyrophosphate
      synthetase 2 (PRPS2) 5' untranslated region
      (5'UTR) 5' terminal oligopyrimidine (5' TOP)

<400> SEQUENCE: 39
uccucccccu cc                                                        12

<210> SEQ ID NO 40
<211> LENGTH: 28
<212> TYPE: RNA
<213> ORGANISM: Artificial Sequence
<220> FEATURE:
<223> OTHER INFORMATION: synthetic human phosphoribosyl pyrophosphate
      synthetase 2 (PRPS2) 5' untranslated region
      (5'UTR) region from -143 to -116

<400> SEQUENCE: 40
uccucccccu ccgcuccucc ccuucccu                                       28
```

PHOSPHORIBOSYL PYROPHOSPHATE SYNTHETASE 2 (PRPS2) AS A THERAPEUTIC TARGET IN CANCER TREATMENT

CROSS-REFERENCE TO RELATED APPLICATIONS

The present application is a national stage application under 35 U.S.C. 371 of PCT/US2014/012552, filed Jan. 22, 2014, which claims priority to U.S. Provisional Application No. 61/755,392, filed Jan. 22, 2013, the entire content of each of which is incorporated by reference herein for all purposes.

STATEMENT AS TO RIGHTS TO INVENTIONS MADE UNDER FEDERALLY SPONSORED RESEARCH AND DEVELOPMENT

This invention was made with government support under grant no. R01 CA140456, awarded by the National Institutes of Health. The government has certain rights in the invention.

BACKGROUND OF THE INVENTION

Cancer cells exhibit altered cellular metabolism in order to promote growth and proliferation. Cells harboring oncogenic lesions that result in hyperactivated c-Myc (Myc) are characterized by an increased demand for the nutrients glucose and glutamine, which are used by the cell to generate energy and to supply metabolic precursors for anabolic processes. A hallmark of Myc-driven cancers is an increase in global translation, one of the most energetically expensive processes in the cell.

Cancer cells display upregulation of nucleotide biosynthetic pathways to meet the demands of growth and proliferation. Indeed, many chemotherapies exist that inhibit enzymes responsible for nucleotide production. However, numerous problems still remain regarding the effectiveness of these drugs in the clinic. For instance, significant side effects are associated with many nucleotide biosynthesis inhibitors. Additionally, some cancers develop mechanisms of resistance to nucleotide biosynthesis inhibitors, rendering them ineffective altogether.

Thus, there remains a need for therapeutic methods that target the nucleotide biosynthetic pathway. The present invention addresses this need and others.

BRIEF SUMMARY OF THE INVENTION

In one aspect, the present invention relates to methods of selectively killing a cell. In some embodiments, the method comprises contacting the cell with an agent that inhibits PRPS2, thereby selectively killing the cell.

In some embodiments, the cell is a neoplastic cell. In some embodiments, the neoplastic cell is a cancer cell. In some embodiments, the cancer is associated with Myc hyperactivation. In some embodiments, the cancer is bladder cancer, breast cancer, colon cancer, gastric cancer, hepatic cancer, ovarian cancer, prostate cancer, lung cancer, melanoma, neuroblastoma, or lymphoma.

In another aspect, the present invention relates to methods of treating a neoplastic disease in a subject. In some embodiments, the method comprises administering to the subject an agent that inhibits phospho-ribosyl pyrophophosphate synthetase 2 (PRPS2), wherein the agent selectively kills neoplastic cells in the subject, thereby treating the neoplastic disease.

In some embodiments, the neoplastic disease is a cancer. In some embodiments, the cancer is associated with Myc hyperactivation. In some embodiments, the cancer is bladder cancer, breast cancer, colon cancer, gastric cancer, hepatic cancer, ovarian cancer, prostate cancer, lung cancer, melanoma, neuroblastoma, or lymphoma. In some embodiments, the subject is a human.

In some embodiments, the agent directly inhibits PRPS2. In some embodiments, the agent targets at least a portion of a pyrimidine-rich translational element (PRTE) or 5' terminal oligopyrimidine (5' TOP) sequence within the 5' untranslated region (5' UTR) of PRPS2, or targets a protein that binds at least a portion of the PRTE or 5' TOP sequence. In some embodiments, the agent inhibits cap-dependent translation of PRPS2. In some embodiments, the agent inhibits cap-dependent translation of PRPS2 by inhibiting Eukaryotic translation initiation factor 4E ("eIF4E"). In some embodiments, the agent inhibits PRPS2 enzymatic activity. In some embodiments, the agent does not inhibit phosphoribosyl pyrophophosphate synthetase 1 (PRPS1).

In some embodiments, the agent is an inhibitory RNA, peptide, protein, or small molecule. In some embodiments, the inhibitory RNA is an shRNA, siRNA, or miRNA.

In still another aspect, the present invention relates to methods for identifying a candidate agent that selectively kills neoplastic cells that are Myc-hyperactivated via inhibition of phospho-ribosyl pyrophophosphate synthetase 2 (PRPS2). In some embodiments, the method comprises:
contacting a biological sample with an agent, wherein the biological sample expresses PRPS2 prior to the contacting; and
comparing the level of activity of PRPS2 in the contacted sample to the level of activity of PRPS2 in the biological sample prior to the contacting,
wherein a decreased level of activity of PRPS2 in the contacted sample as compared to the level of activity of PRPS2 in the biological sample prior to the contacting identifies the agent as a candidate agent that selectively kills Myc-hyperactivated neoplastic cells via inhibition of PRPS2.

In some embodiments, the method further comprises validating the candidate agent as an agent that selectively kills Myc-hyperactivated neoplastic cells via inhibition of PRPS2, wherein the validating comprises determining whether the candidate agent inhibits PRPS2 in an assay.

In some embodiments, the biological sample is from a human or a non-human mammal. In some embodiments, the biological sample is a cancer cell. In some embodiments, In some embodiments, the cancer is bladder cancer, breast cancer, colon cancer, gastric cancer, hepatic cancer, ovarian cancer, prostate cancer, lung cancer, melanoma, neuroblastoma, or lymphoma.

In some embodiments, the level of activity of PRPS2 is decreased by at least 20% in the contacted sample as compared to the level of activity of PRPS2 in the biological sample prior to the contacting.

In some embodiments, the agent does not inhibit phospho-ribosyl pyrophophosphate synthetase 1 (PRPS1). In some embodiments, the agent is an inhibitory RNA, peptide, protein, or small molecule. In some embodiments, the inhibitory RNA is an shRNA, siRNA, or miRNA. In some embodiments, the candidate agent targets at least a portion of a pyrimidine-rich translational element (PRTE) within the 5' untranslated region (5' UTR) of PRPS2 (e.g., SEQ ID NO:3, SEQ ID NO:37, or SEQ ID NO:38), or a protein that targets at least a portion of the PRTE. In some embodiments, the candidate agent targets at least a portion of a 5' terminal oligopyrimidine (5' TOP) sequence within the 5' UTR of PRPS2 (e.g., SEQ ID NO:39) or a protein that targets at least a portion of the 5' TOP sequence. In some embodiments, the candidate agent binds the ATP binding site of PRPS2, the 5-phosphoribosyl 1-pyrophosphate ("PRPP") binding site, or the allosteric regulatory site.

In some embodiments, the method further comprises chemically synthesizing a structurally related agent derived from the candidate agent.

In yet another aspect, the present invention relates to the structurally related agents derived from the candidate agent as described herein.

In still another aspect, the present invention relates to pharmaceutical compositions comprising an agent as described herein (e.g., a structurally related agent derived from a candidate agent as described herein) and a pharmaceutically acceptable excipient. In yet another aspect, the present invention relates to the use of an agent that inhibits PRPS2 as described herein for the selective killing of cells (e.g., cancer cells) in a subject in need thereof (e.g., in a subject having a cancer).

BRIEF DESCRIPTION OF THE DRAWINGS

FIG. 7. Prps2 is regulated at the translational level by a specific cis-acting sequence element within its 5' UTR. (A) Sequences of mouse Prps2 (SEQ ID NO:1) and Prps1 (SEQ ID NO:2) 5' UTRs. The underlined region in Prps2 denotes a pyrimidine-rich translational element (PRTE) sequence: UCCCUUUCUCCUUCUCC (SEQ ID NO:3). The bold AUG represents the start codon for each sequence. The numbering for each sequence is relative to translational start codon. (B) Sequences of human Prps2 (SEQ ID NO:35) and Prps1 (SEQ ID NO:36) 5' UTRs. The underlined regions in Prps2 denote PRTE sequences UCCCCUUCCCU (SEQ ID NO:37) and CCUCCGCCACCUCCUCC (SEQ ID NO:38). The wavy underlined region denotes a 5' terminal oligopyrimidine (5' TOP) sequence: UCCUCCCCCUCC (SEQ ID NO:39). The region from −143 to −116 (UCCUCCCCCUC- CGCUCCUCCCCUUCCCU) is SEQ ID NO:40. The bold AUG represents the start codon for each sequence. The numbering for each sequence is relative to translational start codon.

DETAILED DESCRIPTION OF THE INVENTION

I. Introduction

Figure 1A:
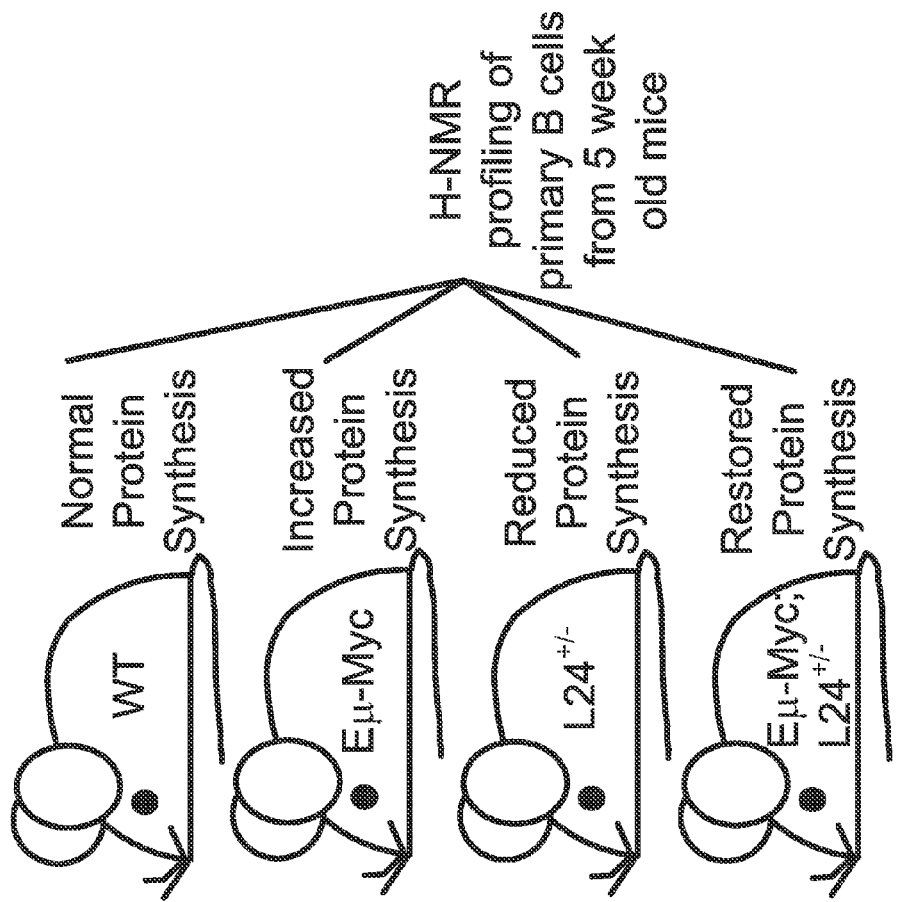
FIG. 1. Myc-dependent increases in protein synthesis lead to increased intracellular purine levels. (A) Schematic of metabolic profiling approach. (B) Heat map corresponding to intracellular concentrations of the identified metabolites in each of the given genotypes. (C) Representative H-NMR spectra and averaged spectra within the purine region of H-NMR (between 8.52 and 8.61 ppm) from cells for each of the genotypes listed (inset). (D) Metabolic flux through de novo purine synthesis pathway measured by [$^{14}$C] formate incorporation in WT and Eµ-Myc/+-derived B cells. (E) Metabolic flux through purine salvage pathway measured by [8-$^{14}$C] hypoxanthine incorporation in WT and Eµ-Myc/+ derived B cells. (F) Western blot analysis of selected nucleotide biosynthesis genes from B cells isolated from 5 week old mice of the given genotypes. (G) mRNA levels of genes in (F) were assayed by qRT-PCR and normalized to β-actin expression. Error bars represent standard deviation, N=6 for (D) and (E), N=4 for (G), * denotes $p<0.05$,  denotes $p<0.01$, * denotes $p<0.001$ by student's t-test.

The present invention relates in part to the identification of phospho-ribosyl pyrophophosphate synthetase 2 (PRPS2)

as a gene that is translationally regulated by the protooncogene c-Myc (Myc). It has previously been shown that Myc's ability to increase protein synthesis is required to effectively drive tumorigenesis. As described herein, inhibition of PRPS2 results in the selective killing of Myc-overexpressing cells (e.g., oncogenic cells) but not normal cells.

Thus, in one aspect the present invention relates to methods of selectively killing Myc-overexpressing cells such as oncogenic cells by specifically inhibiting PRPS2. In another aspect, the present invention relates to methods of identifying a candidate agent that selectively kills cells that are Myc-hyperactivated via inhibition of PRPS2. In still another aspect, the present invention relates to pharmaceutical compositions comprising an agent that specifically inhibits PRPS2. Various exemplary embodiments of the invention are described in further detail below.

II. Definitions

As used herein, the term "phospho-ribosyl pyrophophosphate synthetase 2" or "PRPS2" refers to an isoform of the phospho-ribosyl pyrophophosphate synthetase that catalyzes the synthesis of 5-phosphoribosyl 1-pyrophosphate from ATP and D-ribose 5-phosphate in nucleotide (purine and pyrimidine) synthesis. PRPS2 is described, for example, in Becker, *Prog Nucleic Acid Res Mol Biol* 69:115-48 (2001). PRPS2 gene and protein sequences are set forth in, e.g., at National Center for Biotechnology Information (NCBI) Gene ID 5634.

The term "selectively kills," as used in reference to a cell, refers to directly or indirectly reducing the number or relative percentage of a certain population of cells. In some embodiments, the subpopulation of cells are Myc-hyperactivated cells. In some embodiments, at least 10%, at least 20%, at least 30%, at least 40%, at least 50%, at least 60%, at least 70%, at least 80%, at least 90% or more of the certain population of cells (e.g., Myc-hyperactivated cells) are killed. The cells can be killed by any pathway or mechanism, such as by apoptosis, necrosis, and/or autophagy. Methods of detecting cell death by apoptosis, necrosis, or autophagy are described, e.g., in Amaravadi and Thompson, *Clin Cancer Res* 13:7271-7279 (2007). In some embodiments, apoptosis can be measured by detecting loss of plasma membrane (e.g., by staining with Annexin V) or condensation of the nucleus (e.g., by staining with a nuclear stain); by detecting apoptotically-expressed proteins (e.g., activated caspases); or by TUNEL (Terminal dUTP Nicked-End Labeling) assay.

The term "Myc-hyperactivated," as used in reference to a cell or sample, refers to a cell or sample that has at least 10%, 20%, 30%, 40%, 50%, 75%, 100%, 150%, or 200% greater Myc activity or Myc-pathway signaling than the Myc activity or signaling in a control (e.g., non-diseased) cell or sample. The control cell or sample can be from a normal (non-diseased) tissue adjacent to the Myc-hyperactivated tissue, or from a tissue or subject that is known to not have aberrantly regulated Myc signaling, or from a pool of such cells or samples.

The term "inhibit" or "inhibiting" refers to decreasing, preventing, blocking, inactivating, delaying activation, desensitizing, antagonizing, or downregulating the activity of a gene (e.g., PRPS2). In some embodiments, an agent inhibits PRPS2 if it decreases the activity of PRPS2 by at least 10%, at least 15%, at least 20%, at least 25%, at least 30%, at least 35%, at least 40%, at least 45%, at least 50%, at least 60%, at least 70%, at least 80%, or at least 90% or more in the contacted sample as compared to a control sample (e.g., the biological sample prior to the contacting). In some embodiments, an agent inhibits PRPS2 if it decreases the activity of PRPS2 by at least about 1-fold, 2-fold, 3-fold, 4-fold, 5-fold, 6-fold, 7-fold, 8-fold, 9-fold, 10-fold, 15-fold, 20-fold or more in the contacted sample as compared to a control sample (e.g., the biological sample prior to the contacting). In some embodiments, an agent specifically inhibits PRPS2 but not the phospho-ribosyl pyrophophosphate synthetase isoform PRPS1, i.e., it inhibits PRPS2 with at least 2-fold greater specificity as compared to PRPS1, e.g., at least 4-fold, 5-fold, 6-fold, 7-fold, 8-fold, 9-fold, 10-fold, 20-fold, 25-fold, 50-fold, or 100-fold greater specificity than PRPS1.

The term "agent" refers to refers to any molecule, either naturally occurring or synthetic, e.g., peptide, protein, oligopeptide (e.g., from about 5 to about 25 amino acids in length, preferably from about 10 to 20 or 12 to 18 amino acids in length, preferably 12, 15, or 18 amino acids in length), small organic molecule (e.g., an organic molecule having a molecular weight of less than about 2500 daltons, e.g., less than 2000, less than 1000, or less than 500 daltons), circular peptide, peptidomimetic, antibody, polysaccharide, lipid, fatty acid, inhibitory RNA (e.g., siRNA or shRNA), polynucleotide, oligonucleotide, aptamer, drug compound, or other compound.

A "biological sample" includes blood and blood fractions or products (e.g., serum, plasma, platelets, red blood cells, and the like); sputum or saliva; kidney, lung, liver, heart, brain, nervous tissue, thyroid, eye, skeletal muscle, cartilage, or bone tissue; cultured cells, e.g., primary cultures, explants, and transformed cells, stem cells, stool, urine, etc. Such biological samples also include sections of tissues such as biopsy and autopsy samples, and frozen sections taken for histologic purposes. A biological sample is typically obtained from a "subject," i.e., a eukaryotic organism, most preferably a mammal such as a primate, e.g., chimpanzee or human; cow; dog; cat; a rodent, e.g., guinea pig, rat, or mouse; rabbit; or a bird; reptile; or fish.

The terms "administer," "administered," or "administering" refer to methods of delivering agents or compositions to the desired site of biological action. These methods include, but are not limited to, topical delivery, parenteral delivery, intravenous delivery, intradermal delivery, intramuscular delivery, colonical delivery, rectal delivery, or intraperitoneal delivery. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

III. Methods of Selectively Killing Cells

In one aspect, the present invention relates to methods of selectively killing cells. In some embodiments, the method comprises: contacting the cell with an agent that inhibits PRPS2, thereby selectively killing the cell.

In a related aspect, the present invention provides therapeutic methods of selectively killing cells. In some embodiments, the therapeutic method is a method of treating a neoplastic disease in a subject. In some embodiments, the method comprises: administering to the subject an agent that inhibits PRPS2, wherein the agent selectively kills neoplastic cells in the subject, thereby treating the neoplastic disease.

Cells

In some embodiments, a cell that is targeted for selective killing is a Myc-overexpressing and/or Myc-hyperactivated cell. In some embodiments, a Myc-overexpressing cell is a cell that expresses the Myc gene and/or protein at a level that is at least 10%, 20%, 30%, 40%, 50%, 75%, 100%, 150%, or 200% higher or more, or at least 1-fold, 2-fold, 3-fold, 4-fold, 5-fold, 6-fold, 7-fold, 8-fold, 9-fold, or 10-fold higher or more as compared to a control cell (e.g., a non-diseased cell). In some embodiments, a Myc-hyperactivated cell is a cell that has at least 10%, 20%, 30%, 40%, 50%, 75%, 100%, 150%, or 200% greater Myc activity or Myc-pathway signaling than the Myc activity or signaling in a control cell (e.g., non-diseased cell).

In some embodiments, a cell that is targeted for selective killing is a neoplastic cell. In some embodiments, the neoplastic cell is a pre-cancerous cell. In some embodiments, the neoplastic cell is a cancer cell. In some embodiments, the neoplastic cell (e.g., cancer cell) is a diseased cell wherein the disease (e.g., cancer) is associated with Myc-hyperactivation. In some embodiments, the disease is cancer. In some embodiments, the cancer is bladder cancer, breast cancer, colon cancer, gastric cancer, hepatic cancer, ovarian cancer, prostate cancer, lung cancer, melanoma, neuroblastoma, or lymphoma (e.g., Hodgkin's lymphoma or a non-Hodgkin's lymphoma, e.g., Burkitt's lymphoma). In some embodiments, the cancer is a metastatic cancer. In some embodiments, the cancer is lymphoma.

Agents that Inhibit PRPS2

In some embodiments, an agent that can be used according to the methods of the present invention to inhibit PRPS2 is a peptide, protein, oligopeptide, circular peptide, peptidomimetic, antibody, polysaccharide, lipid, fatty acid, inhibitory RNA (e.g., siRNA, miRNA, or shRNA), polynucleotide, oligonucleotide, aptamer, small organic molecule, or drug compound. In some embodiments, the agent is an inhibitory RNA, e.g., an shRNA, siRNA, or miRNA. The agent can be either synthetic or naturally-occurring.

In some embodiments, the agent is an inhibitory RNA. In some embodiments, the inhibitory RNA targets a sequence that is identical or substantially identical (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical) to a target sequence of SEQ ID NO:27 or SEQ ID NO:28.

In some embodiments, the agent inhibits PRPS2 directly. In some embodiments, the agent inhibits cap-dependent translation of PRPS2. For example, in some embodiments, (i) the agent inhibits or represses translation by binding to at least a portion of the pyrimidine-rich translational element (PRTE) motif of PRPS2, the 5' terminal oligopyrimidine (5' TOP) motif of PRPS2 (e.g., human PRPS2), or both motifs; (ii) the agent inhibits or represses translation by regulating or modulating a protein (e.g., a human protein) that binds at least a portion of the PRTE motif of PRPS2, the 5' TOP motif of PRPS2, or both motifs; or (iii) the agent inhibits or represses translation by regulating or modulating a protein (e.g., a human protein) that binds with the protein of (ii). In another example, in some embodiments the agent inhibits or represses cap-dependent translation by regulating or modulating a component (e.g., a human gene or protein) of the eIF4E/4EBP complex (e.g., by inhibiting or repressing the expression or activity of eIF4E), a component of the eIF4F complex, or a component of the eIF2 complex. In yet another example, in some embodiments, the agent inhibits or represses cap-dependent translation by regulating or modulating a human gene or protein of eIF4A, eIF4B, eIF4E, eIF4G, eIF4H, 4EBP, MNK, eIF2, eIF1/eIF1A, eIF3, eIF5, or eFI6.

In some embodiments, the agent targets at least a portion of SEQ ID NO:1 or SEQ ID NO:35, or targets a protein that binds at least a portion of SEQ ID NO:1 or SEQ ID NO:35. In some embodiments, the agent targets at least a portion of SEQ ID NO:3, SEQ ID NO:37, or SEQ ID NO:38, or targets a protein that binds to at least a portion of SEQ ID NO:3, SEQ ID NO:37, or SEQ ID NO:38. In some embodiments, the agent targets at least a portion of SEQ ID NO:39, or targets a protein that binds at least a portion of SEQ ID NO:39. In some embodiments, the agent targets at least a portion of SEQ ID NO:40, or targets a protein that binds at least a portion of SEQ ID NO:40.

In some embodiments, the agent inhibits PRPS2 enzymatic activity. For example, in some embodiments the agent binds to and/or inhibits the ATP binding and catalytic region of PRPS2.

In some embodiments, the agent specifically inhibits PRPS2 but does not substantially inhibit PRPS1. As used herein, an agent specifically inhibits PRPS2 but does not substantially inhibit PRPS1 if it inhibits PRPS2 with at least 2-fold greater specificity as compared to PRPS1, e.g., at least 4-fold, 5-fold, 6-fold, 7-fold, 8-fold, 9-fold, 10-fold, 20-fold, 25-fold, 50-fold, or 100-fold greater specificity than PRPS1. In some embodiments, specific inhibition of PRPS2 but not PRPS1 is measured using any of a number of enzymatic assays known in the art. For examples, in some embodiments an agent that specifically inhibits PRPS2 but does not substantially inhibit PRPS1 is identified as an agent that decreases the activity of PRPS2 by at least 10%, at least 15%, at least 20%, at least 25%, at least 30%, at least 35%, at least 40%, at least 45%, at least 50%, at least 60%, at least 70%, at least 80%, or at least 90% in a sample that is contacted to the agent as compared to a control sample (e.g., the biological sample prior to the contacting) but does not decrease the activity of PRPS1 more than 20%, more than 15%, more than 10%, more than 5%, more than 4%, more than 3%, more than 2%, or more than 1% in a sample that is contacted to the agent as compared to a control sample (e.g., the biological sample prior to the contacting).

In some embodiments, the agent specifically kills at least 10%, at least 20%, at least 30%, at least 40%, at least 50%, at least 60%, at least 70%, at least 80%, at least 90% or more of the targeted population of cells (e.g., Myc-hyperactivated cells). In some embodiments, the agent selectively kills the targeted cells or population of cells via apoptosis. In some embodiments, the agent selectively kills the targeted cells or population of cells via necrosis. In some embodiments, the agent selectively kills the targeted cells or population of cells via autophagy. Detection and quantitation of cell killing by apoptosis, necrosis, and/or autophagy can be measured according to any method known in the art.

In some embodiments, multiple agents (e.g., 2, 3, 4, 5, or more agents) are used. In some embodiments, multiple agents are administered to a subject or contacted to a cell sequentially. In some embodiments, multiple agents are administered to a subject or contacted to a cell concurrently.

The agents described herein can be used at varying concentrations. In some embodiments, an agent is administered to a subject or contacted to a cell at a concentration that is known or expected to be a therapeutic dose. In some embodiments, an agent is administered to a subject or contacted to a cell at a concentration that is known or expected to be a sub-therapeutic dose. In some embodiments, an agent is administered to a subject or contacted to a cell at a concentration that is lower than a concentration that would typically be administered to an organism or applied to a cell, e.g., at a concentration that is 2, 3, 4, 5, 6, 7, 8, 9, 10, 15, 20, 25, 30, 35, 40, 45, 50, 60, 70, 80, 90, or 100 times less than the concentration that would typically be administered to an organism or applied to a cell.

Administration of Therapeutic Agents

In some embodiments, an agent that inhibits PRPS2 as described herein is administered to a subject according to a therapeutic method of the present invention. A subject can be any human or non-human mammal. In some embodiments, the subject is a human, e.g., a human adult or a human child.

In some embodiments, the subject has a disease. In some embodiments, the disease is cancer. Non-limiting examples of cancers that can be treated according to the methods of the present invention include, but are not limited to, anal carcinoma, bladder carcinoma, breast carcinoma, cervix carcinoma, chronic lymphocytic leukemia, chronic myelogenous leukemia, endometrial carcinoma, hairy cell leukemia, head and neck carcinoma, lung (small cell) carcinoma, multiple myeloma, Hodgkin's lymphoma, non-Hodgkin's lymphoma (e.g., Burkitt's lymphoma), follicular lymphoma, ovarian carcinoma, brain tumors, colorectal carcinoma, hepatocellular carcinoma, Kaposi's sarcoma, lung (non-small cell carcinoma), melanoma, pancreatic carcinoma, prostate carcinoma, renal cell carcinoma, and soft tissue sarcoma. In some embodiments, the cancer is bladder cancer, breast cancer, colon cancer, gastric cancer, hepatic cancer, ovarian cancer, prostate cancer, lung cancer, melanoma, neuroblastoma, or lymphoma. In some embodiments, the cancer is an invasive cancer. In some embodiments, the cancer is a metastatic cancer.

A therapeutic agent can be any agent that inhibits PRPS2 as described herein. Generally, the therapeutic agent is administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient. Determination of an effective amount is well within the capability of those skilled in the art.

The route of administration of a therapeutic agent can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art.

IV. Identification of Agents that Selectively Kill Myc-Hyperactivated Cells

In another aspect, the present invention relates to methods of identifying candidate agents that selectively kill cells (e.g., Myc-hyperactivated neoplastic cells) via inhibition of PRPS2. In some embodiments, the method comprises:
  contacting a biological sample with an agent, wherein the biological sample expresses PRPS2 prior to the contacting; and
  comparing the level of activity of PRPS2 in the contacted sample to the level of activity of PRPS2 in the biological sample prior to the contacting,
  wherein a decreased level of activity of PRPS2 in the contacted sample as compared to the level of activity of PRPS2 in the biological sample prior to the contacting identifies the agent as a candidate agent that selectively kills Myc-hyperactivated neoplastic cells via inhibition of PRPS2.

In some embodiments, the agent that is contacted to the biological sample is known to kill cells.

In some embodiments, the candidate agent inhibits cap-dependent translation of PRPS2. In some embodiments, the candidate agent inhibits PRPS2 enzymatic activity. In some embodiments, the candidate agent binds the ATP binding site of PRPS2, the 5-phosphoribosyl 1-pyrophosphate (PRPP) binding site of PRPS2, or the allosteric regulatory site of PRPS2. In some embodiments, the candidate agent binds the pyrimidine-rich translational element (PRTE) motif of PRPS2, the 5' terminal oligopyrimidine (5' TOP) motif of PRPS2, or to a protein that binds the PRTE motif of PRPS2 or the 5' TOP motif of PRPS2.

In some embodiments, the method further comprises measuring the level of phospho-ribosyl pyrophophosphate synthetase 1 (PRPS1) in the contacted sample as compared to the level of PRPS1 in the sample prior to the contacting. In some embodiments, an agent is identified as a candidate agent when the agent does not substantially inhibit PRPS1.

Agents that can be screened according to the methods of the present invention to identify candidate agents that selectively kill Myc-hyperactivated neoplastic cells via inhibition of PRPS2 include the agents described herein, e.g., in Section III above. In some embodiments, the agent is an inhibitory RNA, peptide, protein, or small molecule. In some embodiments, the agent is an inhibitory RNA, e.g., an shRNA, siRNA, or miRNA.

Measuring PRPS2 Activity

In some embodiments, PRPS2 has a decreased level of activity in the contacted sample as compared to the level of activity of PRPS2 in the sample prior to the contacting when the level of activity of PRPS2 is decreased by at least 10%, at least 15%, at least 20%, at least 25%, at least 30%, at least 35%, at least 40%, at least 45%, at least 50%, at least 60%, at least 70%, at least 80%, or at least 90% in the contacted sample as compared to the level of activity of PRPS2 in the biological sample prior to the contacting. In some embodiments, PRPS2 has a decreased level of activity in the contacted sample when the level of activity of PRPS2 is decreased by at least about 1-fold, 2-fold, 3-fold, 4-fold, 5-fold, 6-fold, 7-fold, 8-fold, 9-fold, 10-fold, 15-fold, 20-fold or more in the contacted sample as compared to the level of activity of PRPS2 in the biological sample prior to the contacting.

The level of activity of PRPS2 can be measured according to any methods known in the art. As a non-limiting example, the level of activity of PRPS2 can be determined by measuring the enzymatic activity of PRPS2. Methods of measuring PRPS2 activity are known in the art. See, e.g., Braven J., et al., *Ann Clin Biochem* (1984) 21:366-71), and Jensen, K. F., et al., *Analytical Biochemistry* (1979) 98:254-263. For example, PRPS2 activity can be measured by continuous spectrolphotometric rate determination to measure the rate of catalysis of phosphoribosyl pyrophosphate (PRPP) and AMP from ATP and ribose 5-phosphate.

As another non-limiting example, the level of activity of PRPS2 can be determined by measuring PRPS2 expression. PRPS2 expression can be measured using any of a number of immunoassays known in the art Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (META); capillary electrophoresis immunoassays (CEIA); radioimmunoassays (RIA); immunoradiometric assays (IRMA); immunofluorescence (IF); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)).

Specific immunological binding of an antibody to a protein (e.g., PRPS2) can be detected directly or indirectly. Direct labels include fluorescent or luminescent tags, metals, dyes, radionuclides, and the like, attached to the antibody. An antibody labeled with iodine-125 ($^{125}I$) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}I$; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously. In some embodiments, the amount of signal can be quantified using an automated high-content imaging system. High-content imaging systems are commercially available (e.g., ImageXpress, Molecular Devices Inc., Sunnyvale, Calif.).

Antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

The analysis can be carried out in a variety of physical formats. For example, the use of microtiter plates or automation could be used to facilitate the processing of large numbers of test samples.

In some embodiments, the biological sample comprises a neoplastic cell that is Myc-hyperactivated. In some embodiments, the biological sample comprises a cancer cell (e.g., a cell obtained or derived from a tumor). In some embodiments, the cancer is bladder cancer, breast cancer, colon cancer, gastric cancer, hepatic cancer, ovarian cancer, prostate cancer, lung cancer, melanoma, neuroblastoma, or lymphoma.

In some embodiments, the biological sample is from a human subject. In some embodiments, the biological sample is from a non-human mammal (e.g., chimpanzee, dog, cat, pig, mouse, rat, sheep, goat, or horse), avian (e.g., pigeon, penguin, eagle, chicken, duck, or goose), reptile (e.g., snake, lizard, alligator, or turtle), amphibian (e.g., frog, toad, salamander, caecilian, or newt), or fish (e.g., shark, salmon, trout, or sturgeon).

Validation of Candidate Agents

In some embodiments, the method further comprises validating a candidate agent identified according to the methods described herein as an agent that selectively kills Myc-hyperactivated neoplastic cells via inhibition of PRPS2, wherein the validating comprises determining whether the candidate agent inhibits PRPS2 in an assay. In some embodiments, the assay is a functional assay (e.g., an assay measuring nucleotide biosynthesis). See, e.g., Mannava et al., *Cell Cycle* 7:2392-2400 (2008). As a non-limiting example, inhibition of PRPS2 activity can be determined by measuring the enzymatic activity of PRPS2 in the presence or absence of a candidate agent. For example, PRPS2 activity can be measured by continuous spectrolphotometric rate determination to measure the rate of catalysis of phosphoribosyl pyrophosphate (PRPP) and AMP from ATP and ribose 5-phosphate.

In some embodiments, the method further comprises determining whether the candidate agent selectively kills Myc-hyperactivated cells in an assay. In some embodiments, the assay is an assay that detects and/or quantifies apoptosis. In some embodiments, the assay is an assay that detects and/or quantifies necrosis. In some embodiments, the assay is an assay that detects and/or quantifies autophagy. Any methods known in the art for detecting and/or quantifying, necrosis, or autophagy can be used. As a non-limiting example, apoptosis can be measured by detecting loss of plasma membrane (e.g., by staining with Annexin V) or condensation of the nucleus (e.g., by staining with a nuclear stain); by detecting apoptotically-expressed proteins (e.g., activated caspases); or by TUNEL (Terminal dUTP Nicked-End Labeling) assay.

Synthesizing Agents Based on Candidate Agents

In some embodiments, an agent that is identified as selectively killing Myc-hyperactivated neoplastic cells via inhibition of PRPS2 is optimized in order to improve the agent's biological and/or pharmacological properties. To optimize the agent, structurally related analogs of the agent can be chemically synthesized to systematically modify the structure of the initially-identified agent.

For chemical synthesis, solid phase synthesis can be used for compounds such as peptides, nucleic acids, organic molecules, etc., since in general solid phase synthesis is a straightforward approach with excellent scalability to commercial scale. Techniques for solid phase synthesis are described in the art. See, e.g., Seneci, *Solid Phase Synthesis and Combinatorial Technologies* (John Wiley & Sons 2002); Barany & Merrifield, *Solid-Phase Peptide Synthesis*, pp. 3-284 in *The Peptides: Analysis, Synthesis, Biology, Vol. 2* (E. Gross and J. Meienhofer, eds., Academic Press 1979).

The synthesized structurally related analogs can be screened to determine whether the analogs inhibit PRPS2 substantially as well as or better than the initial agent from which the analog was derived. In some embodiments, a selected-for structurally related analog is one that inhibits PRPS2 in a contacted sample at least as well as the candidate agent from which the analog was derived (e.g., by at least 10%, at least 15%, at least 20%, at least 25%, at least 30%, at least 35%, at least 40%, at least 45%, at least 50%, at least 60%, at least 70%, at least 80%, or at least 90% in the contacted sample as compared to the level of activity of PRPS2 in the biological sample prior to the contacting). In some embodiments, a selected-for structurally related analog inhibits cap-dependent translation of PRPS2. For example, in some embodiments a selected-for structurally related analog inhibits or represses cap-dependent translation by regulating or modulating a component of the eIF4E/4EBP complex (e.g., by inhibiting or repressing the expression or activity of eIF4E), a component of the eIF4F complex, or a component of the eIF2 complex. In some embodiments, the agent inhibits or represses cap-dependent translation by regulating or modulating eIF4A, eIF4B, eIF4E, eIF4G, eIF4H, 4EBP, MNK, eIF2, eIF1/eIF1A, eIF3, eIF5, or eIF6. In some embodiments, the selected-for structurally related analog inhibits PRPS2 enzymatic activity. In some embodiments, a selected-for structurally related analog binds the ATP binding site of PRPS2, the PRPP binding site, or the allosteric regulatory site of PRPS2. In some embodiments, a selected-for structurally related analog binds the PRTE motif or 5' TOP motif of PRPS2.

A structurally related analog that is determined to inhibit PRPS2 at least as well as the initial agent from which the structurally related analog was derived can be further screened for biological and pharmacological properties, including but not limited to oral bioavailability, half-life, metabolism, toxicity, and pharmacodynamic activity (e.g., duration of the therapeutic effect) according to methods known in the art. Typically, the screening of the structurally related analogs is performed in vivo in an appropriate animal model (e.g., a mammal such as a mouse or rat). Animal models for analyzing pharmacological and pharmacokinetic properties, including animal models for various disease states, are well known in the art and are commercially available, e.g., from Charles River Laboratories Intl, Inc. (Wilmington, Mass.).

In some embodiments, an agent that is identified as selectively killing Myc-hyperactivated neoplastic cells via inhibition of PRPS2, or a structurally related analog thereof, is used for the preparation of a medicament for the treatment of a disease or condition associated with Myc hyperactivation (e.g., a cancer associated with Myc hyperactivation).

V. Compositions and Kits

In still another aspect, the present invention relates to compositions and kits comprising an agent that selectively kills Myc-hyperactivated cells as described herein. In some embodiments, the composition or kit comprises an agent that inhibits PRPS2, wherein the agent selectively kills Myc-hyperactivated cells when the agent is contacted to the cells. In some embodiments, the composition or kit comprises an agent that inhibits PRPS2 directly. In some embodiments, the composition or kit comprises an agent that inhibits cap-dependent translation of PRPS2. In some embodiments, the composition or kit comprises an agent that inhibits PRPS2 enzymatic activity. In some embodiments, the composition or kit comprises an agent that specifically inhibits PRPS2 but does not substantially inhibit PRPS1.

In some embodiments, the agent is formulated as a pharmaceutical composition. In some embodiments, a pharmaceutical composition incorporates particulate forms, protective coatings, protease inhibitors, or permeation enhancers for various routes of administration, including parenteral, pulmonary, nasal and oral. The pharmaceutical compositions can be administered in a variety of unit dosage forms depending upon the method/mode of administration. Suitable unit dosage forms include, but are not limited to, powders, tablets, pills, capsules, lozenges, suppositories, patches, nasal sprays, injectibles, implantable sustained-release formulations, etc.

Formulations suitable for oral administration can comprise: (a) liquid solutions, such as an effective amount of an agent suspended in diluents, e.g., water, saline, or PEG 400; (b) capsules, sachets, or tablets, each containing a predetermined amount of a compound, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise an agent in a flavor, e.g., sucrose, as well as pastilles comprising the compound in an inert base, such as gelatin and glycerin or sucrose and acacia emulsions, gels, and the like containing, in addition to the agent, carriers known in the art.

The agent, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations can be presented in unit-dose or multi-dose sealed containers, such as ampoules and vials. Injection solutions and suspensions can be prepared from sterile powders, granules, and tablets of the kind previously described.

In some embodiments, a pharmaceutical composition comprises an acceptable carrier and/or excipients. A pharmaceutically acceptable carrier includes any solvents, dispersion media, or coatings that are physiologically compatible and that preferably does not interfere with or otherwise inhibit the activity of the polypeptide or peptidomimetic. Preferably, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, Remington: The Science and Practice of Pharmacy, 21st Edition, Philadelphia, Pa. Lippincott Williams & Wilkins, 2005. Various pharmaceutically acceptable excipients are well-known in the art and can be found in, for example, Handbook of Pharmaceutical Excipients ($5^{th}$ ed., Ed. Rowe et al., Pharmaceutical Press, Washington, D.C.).

The pharmaceutical preparation is preferably in unit dosage form. In such form the preparation is subdivided into unit doses containing appropriate quantities of the active component, e.g., a modulator. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In some embodiments, a composition or kit comprising an agent that selectively kills Myc-hyperactivated cells as described herein is used for the treatment of a disease or condition associated with Myc hyperactivation (e.g., a cancer associated with Myc hyperactivation).

VI. Examples

The following examples are offered to illustrate, but not to limit the claimed invention.

Example 1

Inactivation of PRPS2 Induces Apoptosis in Myc-Hyperactivated Human and Mouse Cancer Cells The proto-oncogene c-Myc directs a coordinated transcriptional program to direct cell growth, proliferation and tumorigenesis via myriad cellular processes. It has been previously shown that Myc's ability to increase protein synthesis is required to effectively drive this oncogenic program. In this example, an unbiased metabolomics approach was utilized, and it was found that the nucleotide biosynthesis pathway is regulated by Myc hyperactivation in a manner dependent on Myc-driven increases in protein synthesis. Employing a candidate gene screen within the nucleotide biosynthesis pathway by RT-PCR and western blot analysis, Phospho-Ribosyl Pyrophosphate Synthetase 2 (PRPS2) was identified as a translationally-regulated Myc target gene. Genetic approaches to specifically inhibit cap-dependent translation demonstrated that PRPS2 expression is translationally regulated through its 5'UTR by an eIF4E/4EBP-dependent mechanism. Knockdown of PRPS2 induces apoptosis specifically in Myc-hyperactivated human and mouse cancer cells but not in normal cells. This study suggests that PRPS2 can be targeted therapeutically in cancers harboring oncogenic lesions leading to Myc hyperactivation.

Experimental Procedures

Generation of $Prps2^{null}$ Mice and Other Mouse Lines Used $PRPS2^{tm1a(KOMP)Wtsi}$ ES cells used for this research project were generation by the trans-NIH Knock-Out Mouse Project (KOMP) and obtained from the KOMP Repository. $PRPS2^{tm1a(KOMP)Wtsi}$ ES cells contain a genetrap insertion in the first intron of the PRPS2 gene, which fuses the first 40 amino acids of PRPS2 to a beta-galactosidase cassette flanked by a SV40 polyadenylation site that acts as a strong transcriptional termination signal. $PRPS2^{tm1a(KOMP)Wtsi}$ ES cells were propagated by the UCSF ES cell core and microinjections of these cells into C57B16 albino females were performed by the Gladstone Institute Transgenic Core Facility to generate chimeric founders. F1 animals were then generated. This mouse strain is referred to as "$Prps2^{null}$" in the text.

Eμ-Myc/+(Eμ-Myc) mice have been previously characterized (Adams, 1985, Nature 318:533-538). $Rpl24^{BST/+}$ ($L24^{+/-}$) mice have been previously characterized (Oliver, 2004, Development 131:3907-3920). To generate Eμ-Myc/+; $Rpl24^{BST/+}$ mice, Eμ-Myc mice were intercrossed to $Rpl24^{BST/+}$ mice (Barna et al., 2008, Nature 256:971-975). CD19-Cre mice have been previously characterized (Rickert et al., 1997, Nucleic Acids Res. 25:1317-1318). TetO-DN-4EBP1 mice have been previously characterized (Hsieh et al., 2010, Cancer Cell 17:249-261). ROSA26-rtTA*M2 mice have been previously characterized and were from Jackson Laboratories (Stock #006965) (Hochedlinger et al., 2005, Cell 121:465-477). ROSA26-Lox-STOP-Lox-rtTA-IRES-GFP mice have been previously characterized (Jackson Laboratories Stock #005670) (Belteki, 2005, Nucleic Acids Res. 33:e51). The University of California San Francisco Institutional Animal Care and Use Committee approved all studies involving live mice.

Magnetic Resonance Data Acquisition and Processing

One dimensional $(1D)^1H$ MR spectra acquisition was performed on the aqueous fraction of freshly isolated B cell extracts as described in further detail below using a 600 MHz Bruker spectrometer equipped with a cryogenically cooled probe. 90° pulse and 4 s relaxation delay were used and the water resonance was suppressed using excitation sculpting (Hwang and Shaka, 1995, J. Magn. Reson. 112: 275-279).

All the MRS datasets were processed using NMRLab in the MATLAB programming environment (The MathWorks, Inc.) (Günther et al., 2000, J. Magn. Reson. 145:201-208). Following standard processing steps, selected signals arising from residual solvents (water, methanol, and chloroform)

and from TMSP were excluded and spectra were normalized according to the probabilistic quotient method (Dieterle et al., 2006, Anal. Chem. 78:4281-4290). For all datasets, MRS resonances of metabolites were assigned by comparison with spectra of standard compounds (Ludwig et al., 2011, Metabolomics 8:8-18). Peak integrals of selected metabolites were calculated using ACD/Spec Manager version 9.15 software (Advanced Chemistry Development) and normalized to the mean of WT samples for relative quantification. For the B cells samples (N=~8 per genotype) statistical significance was determined using a Student's t-test with p<0.05 considered significant.

B Cell Isolation

Splenic B lymphocytes were isolated using Miltenyi Mouse B cell isolation kit (#130-090-862) in conjunction with Miltenyi magnetic separation columns (#130-042-401) per manufacturer's instructions.

Metabolite Extraction from B Cells

B lymphocytes were isolated using MACS separation, pelleted and then re-suspended in 2 mL methanol. To isolate the intracellular aqueous metabolites, chloroform and water were then added to the methanol in equal volumes (final solution 1:1:1 methanol:chloroform:water). The solution was vortexed and centrifuged to separate the aqueous and lipid phases.

For Magnetic Resonance experiments, the dried aqueous phase polar extracts (approximately 8 replicates per genotype) were then re-dissolved in 200 μl of 100 mM phosphate buffer (pH 7.0) prepared in 90% $H_2O$-10% $D_2O$ and containing 0.5 mM sodium 3-(trimethylsilyl)propionate-2,2,3,3-d4 (TMSP, Cambridge Isotope Laboratories) as an internal reference (Ronen et al., 2001, Br. J. Cancer 84:691).

For HPLC and dNTP measurement, the aqueous phase was dried using a spin vac and resuspended in 250 μL HPLC grade water. Subsequently, aqueous extracted metabolites were passed through a Costar Spin-X 0.22 μm cellulose acetate column to remove any particulates prior to analysis by HPLC or PCR-based dNTP quantitation. Cellular dNTP concentrations were measured as described (Ferraro et al., 2009, Nucleic Acids Res. 38:e85). HPLC was performed essentially as described using a Varian Microsorb 100-5 $C_{18}$ 250×4.6 mm (particle size 5 μm) column in conjunction with a Varian ProStar HPLC system (Smolenski et al., 1990, J. Chromatogr. B. Biomed. Sci. App. 527:414-420).

Metabolic Flux Experiments

Metabolic labeling experiments were performed essentially as described (Boss and Erbe, 1982, J. Biol. Chem. 257:4242-4247). [$^{14}$C] formate and [8-$^{14}$C] hypoxanthine were purchased from American Radiolabeled Chemicals, (#ARC 0163A and #ARC 0364, respectively). Briefly, freshly isolated B cells were cultured in growth factor and serum free RPMI 1640 media at a density of 5×10$^6$ cells/mL Immediately after isolation, radiolabeled formate or hypoxanthine was added and cells were cultured for 2 hours. Cells were then harvested, pelleted and lysed in 1 ml of 0.4 N perchloric acid, heated at 100° C. for 70 min, cooled on ice for 5 min, centrifuged at 1000×g for 5 min, and the supernatant was applied to Bio-Spin Disposable Chromatography Columns (Bio-Rad #732-6008) packed with pre-equilibrated AG 50W-X4 Resin, 100-200 mesh (Bio-Rad #142-1341). The columns were washed 8 times 1.0 ml of 0.1 N HCl, and the purines were eluted with 3 washes of 1.0 ml of 6N HCl. A 1.0 mL aliquot of this eluate was added to 10 mL of scintillation fluid and radioactivity was measured by liquid scintillation counting.

qRT-PCR Analysis

RNA was isolated from cells using Trizol reagent (Invitrogen) per manufacturer's instructions. cDNA was generated using High-Capacity cDNA reverse transcription kit (Applied Biosciences). Quantitative real-time PCR was performed using iQ SYBR green mix (BioRad) on a MyIQ2 instrument. Data was analyzed using the Δ-ΔCt method, and data were normalized to expression of β-actin unless otherwise specified. The primers in Table 1 below were used to measure the indicated mouse genes.

TABLE 1 qRT-PCR Primers

| Gene | Direction | Sequence | SEQ ID NO: |
|---|---|---|---|
| β-Actin | Forward | 5'-GACATGGAGAAGA TCTGGCA-3' | 4 |
| β-Actin | Reverse | 5'-GGTCTCAAACATG ATCTGGGT-3' | 5 |
| Prps2 | Forward | 5'-ATGAAGTGGACCG GATGGTT-3' | 6 |
| Prps2 | Reverse | 5'-GGTGGCACCAGCT GAGAGTA-3' | 7 |
| Ppat | Forward | 5'-AGGAATGTGGTGT GTTTGGGT-3' | 8 |
| Ppat | Reverse | 5'-CAATACCAGCGCT CTCCTGA-3' | 9 |
| Umps | Forward | 5'-CCAATCACATTCC CATGCTC-3' | 10 |
| Umps | Reverse | 5'-AACACTGGCTCCG CTGGT-3' | 11 |
| Ctps | Forward | 5'-GTGTGCAGGTGCT CAAATCC-3' | 12 |
| Ctps | Reverse | 5'-CAAGGGTACCCGG TAGATGG-3' | 13 |
| Impdh2 | Forward | 5'-CGCAAGCCAAGAA CCTCATA-3' | 14 |
| Impdh2 | Reverse | 5'-AAGCGACGGGCAT ACTCAG-3' | 15 |
| Atic | Forward | 5'-TATGTGACCGGCA CTATCGG-3' | 16 |
| Atic | Reverse | 5'-GCTTGTCCACCCA TTCCTTC-3' | 17 |
| Prps1 | Forward | 5'-CCTGCCATTTCTC GAATCAA-3' | 18 |
| Prps1 | Reverse | 5'-GTGGGTTCTCCTG ATGGCTT-3' | 19 |
| Rplp0 | Forward | 5'-GCAGACAACGTGG GCTCCAAGCAGAT-3' | 20 |
| Rplp0 | Reverse | 5'-GGTCCTCCTTGGT GAACACGAAGCCC-3' | 21 |

Antibodies and Reagents

The following antibodies were used: PRPS2 (Abnova #H00005634-A01), β-Actin (Sigma #A5316), PPAT (Sigma #HPA036092), IMPDH2 (Sigma #HPA001400), CTPS (Epitomics #6603-1), UMPS (Abcam #ab80857), GAPDH (Cell Signaling #2118), RPS3 (Abeam #ab77772), ATIC (Abeam #ab33520), 4EBP (Cell Signaling #9644), and Tubulin (Sigma #T8203). APC-conjugated rat-anti mouse B220 was from the UCSF hybridoma core. Control and mouse Prps2 siRNA were purchased from Dharmcon. FLAG-Prps2 mRNA was generated from linearized plasmid DNA using the mMessage mMachine T7 Ultra Kit (Invitrogen). FLAG-Prps2 mRNA was transfected into B cells using TransIT transfection reagent (Mirus).

Plasmids and Retrovirus Constructs

FLAG-tagged mouse Prps2 plasmid was generated by TOPO cloning the FLAG-Prps2 PCR fragment into pCRII TOPO vector downstream of the T7 promoter. Luciferase reporter constructs were generated by cloning the mouse Prps2 or Prps1 5' UTR region into the pGL3 promoter vector (Promega) using HindIII and NcoI sites. Site-directed mutagenesis of the Prps2 5' UTR PRTE sequence was performed using oligonucleotides listed in Table 2 below.

TABLE 2

Oligonucleotides Used for Site-Directed Mutagenesis of Prps2 5' UTR PRTE Sequence

| Oligo Name | Sequence | SEQ ID NO: |
|---|---|---|
| Forward ΔPRTE | 5'-cggtagcagtagtctgc atcgcagagcgcgctcctca gtc-3' | 22 |
| Reverse ΔPRTE | 5'-gactgaggagcgcgctc tgcgatgcagactactgcta ccg'-3' | 23 |
| Forward PRTE transversion | 5'-cggtagcagtagtctgc atcgcagAGGGAAAGAGGAA GAGGAgcgcgctcctcagt c-3' | 24 |
| Reverse PRTE transversion | 5'-gactgaggagcgcgctC CTCTTCCTCTTTCCCTctgc gatgcagactactgctacc g-3' | 25 |

The dominant negative mutant of 4EBP1 (DN-4EBP1) cDNA has been previously described (Hsieh et al., 2010, Cancer Cell 17:249-261). The DN-4EBP1 cDNA was subcloned into pMSCV-hygro to generate a constitutive mammalian expression vector for luciferase reporter experiments. Retroviruses containing shRNA hairpins targeting Prps2 were cloned into a pMSCV vector harboring palmitoylated GFP cDNA subcloned downstream of the PGK promoter. The U6 promoter was cloned into the multiple cloning site and the shRNA target sequences in Table 3 below were used.

TABLE 3 shRNA Target Sequences

| Oligo Name | Sequence | SEQ ID NO: |
|---|---|---|
| Control non-targeting shRNA | 5'-CAACAAGATGA AGAGCACCAA-3' | 26 |
| Mouse Prps2 shRNA | 5'-GTGGTTATTTG GTCGTTAATT'-3' | 27 |
| Human PRPS2 shRNA | 5'-TGCAGTGCTTG TATTGGTTTAA-3' | 28 |

The retrovirus expressing inducible shRNA targeting mouse Prps2 (Tet-PRPS2 shRNA MSCV-pGFP) was constructed in the following manner. First, the mouse Prps2 shRNA sequence above was cloned into the Tet-pLKO puro vector (Addgene #21915) and the puromycin resistance gene was replaced with the palmitoylated GFP gene. Then, the region containing the Tet-inducible H1 promoter of this vector through the pGFP gene was subcloned into the MCS of the retroviral pMSCV 2.2 vector.

Cell Culture

NIH3T3 cells and primary wild-type and transformed mouse embryo fibroblasts (MEFs) were cultured in DMEM containing 10% fetal bovine serum (FBS) and penicillin/streptomycin. To generate doxycycline-inducible DN-4EBP1 MEFs, we intercrossed TetO-4EBP mice (Hsieh et al., 2010, Cancer Cell 17:249-261), with ROSA26-rtTA*M2 mice (Jackson Laboratories Stock #006965) (Hochedlinger et al., 2005, Cell 121:465-477). Embryos were harvested at 13.5 d.p.c., fetal liver, head and limbs were removed, embryos were minced with a razor and single cells were obtained by trypsin digestion. To transform MEFs, we transduced them with retroviruses generated from Myc-pWZL and HRas-pBABE plasmids. Daudi and Raji cells were purchased from American Type Culture Collection and maintained in RPMI1640 media supplemented with 10% FBS.

Luciferase Reporter Assays

NIH3T3 cells were transfected with Prps2 or Prps1 5' UTR pGL3 promoter plasmids in presence of DN-4EBP1 pMSCV hygro or empty vector pMSCV hygro in 6 well dishes using lipofectamine (Invitrogen). 24 hours post-transfection, cells were harvested, lysed in passive lysis buffer (Promega) and luciferase assays were performed using a Promega Glomax instrument as described (Hsieh et al., 2012, Nature 485:55-61).

Sucrose Gradient Fractionation and Polysome Profiling

Sucrose gradient fractionation and polysome profiling were performed as described (Hsieh et al., 2012, Nature 485:55-61). Upon polysome fractionation, RNA was extracted and purified using Trizol reagent in conjunction with PureLink RNA isolation kits (Invitrogen). RNA isolated from each fraction was reverse transcribed as described above. For qRT-PCR analysis of polysomal fractions, data are expressed relative to 5S rRNA expression and subsequently represented as a fraction of total mRNA for either Prps1 or Prps2. 5S rRNA primers used were: Forward—5'-GCCCGATCTCGTCTGATCT-3' (SEQ ID NO: 29) and Reverse—5'-AGCCTACAGCACCCGGTATT-3' (SEQ ID NO:30).

Fetal Liver Hematopoietic Stem Cell Culture, Retroviral Preparation, Infection, and Transplantation Fetal liver hematopoietic stem cell (HSC) culture, infection, and transplantation were performed essentially as described with slight variation (Zuber et al., 2010, Nat. Biotechnol. 29:79-83). Day 14.5 pregnant mice from a Eμ-Myc/+ transgenic x Black 6 wild-type cross were sacrificed to obtain fetal livers, which were minced and grown at approximately $3 \times 10^6$ cells/mL in media supporting hematopoietic stem cell (HSC) growth (50% DMEM, 50% Iscove's modified Dulbecco's Medium (Gibco), supplemented with 10% fetal calf serum, 2% L-glutamine (200 mM), 100 U/mL penicillin/streptomycin, 50 μM β-mercaptoethanol, 2 ng/mL recombinant murine interleukin-3, 2 ng/mL recombinant murine interleukin-6, and 10 ng/mL recombinant murine stem cell factor (all cytokines from Peprotech) at 37° C. in a humidified 5% CO2 incubator.

Retroviruses were prepared by transfecting HEK293 cells with Tet-PRPS2 shRNA MSCV-pGFP and pCL-Eco (Addgene #12371) plasmids using PolyFect transfection reagent (Qiagen). 12 hours later, media was replaced with media containing 50% DMEM, 50% Iscove's modified Dulbecco's Medium (Gibco), supplemented with 10% fetal calf serum, 2% L-glutamine (200 mM), 100 U/mL penicillin/streptomycin, and 50 μM β-mercaptoethanol. 24 hours later, virus-containing supernatant was collected, media was replaced and supernatant was filtered through a 0.45 μm syringe filter. Viral supplement was collected up to 72 hours post-infection.

Spinoculation of HSCs was performed 3 days after harvest and culture of HSCs. In a six well dish, approximately $3 \times 10^6$ cells were infected by spinoculation three times with five hours between infections. Briefly, viral supernatant was supplemented with the cytokines at concentrations listed above as well as 4 μg/mL polybrene (Sigma). For each round of infection, 1.5 mL of supplemented filtered viral supernatant was added and cells were spun for 15 minutes at 1500 rpm.

Two days after the last spinoculation, efficacy of infection was assessed by FACS analysis to determine the percentage of GFP positive cells. For all transplanted recipient mice, greater than 60% of donor HSCs was infected. Three days after spinoculation, HSCs were spun down, re-suspended in PBS and $5 \times 10^6$ living HSCs were injected via tail vein into recipient lethally irradiated recipient mice. After one month of recover post-transplantation wherein mice were placed on an antibiotic regimen to prevent infection, mice were segregated into two cohorts and treated with either vehicle (water) or 2 mg/mL doxycycline via their drinking water. Mice were subsequently palpated twice weekly to monitor for development of lymph tumors and survival data was plotted using GraphPad Prism software. P values were calculated using the Logrank test.

Eμ-Myc/+Tumor Cell Culture, Infection, Transplantation, and Monitoring

Eμ-Myc tumor cells were harvested, cultured, and infected with Tet-PRPS2 shRNA MSCV-pGFP essentially as described (Schmitt et al., 2000, Nat. Med. 6:1029-1035). After transplantation via tail vein of approximately $5 \times 10^6$ live tumor cells into syngeneic recipients, tumors were allowed to engraft for several days. Between days 5 and 7 post transplantation, blood samples from tail bleeds were subjected to FACS analysis to assay for tumor take by measurement of GFP positive B220 positive tumor cells. Upon detection of GFP positive population of circulating B220 positive cells, mice were placed in either vehicle (water) or doxycycline (2 mg/mL in water) treatment regimens representing day 0 of the survival curve. Survival was monitored daily and mice were sacrificed upon becoming moribund or developing tumors>1 cm in diameter. Survival was monitored daily and mice were sacrificed upon becoming moribund or developing tumors>1 cm in diameter. Survival data was plotted using GraphPad Prism software. P values were calculated using the Logrank test.

Genotyping Protocol for Prps2$^{null}$ Mice

Prps2$^{null}$ mice were genotyped using the following primers: Forward 5'-ACATTGCCATAAGGAATTATCAGAG-3' (SEQ ID NO:31) and Reverse 5'-GGCGCCAGCCT-GCTTT-3' (SEQ ID NO:32) to detect the mutant allele and Forward 5'-TGCCAGTTATCACCGCTCA-3' (SEQ ID NO:33) and Reverse 5'-GCTGCCCACACTTCACTCTT-3' (SEQ ID NO:34) to detect the wild-type allele. Promega GoTaq DNA polymerase was used to amplify genomic DNA, and cycling conditions were as follows:

1. 94° C. for 1.5 min
2. 94° C. for 30 sec
3. 55° C. for 1 min
4. 72° C. for 1 min
5. Repeat cycles 2-4×35
6. 72° C. for 2 min
7. 4° C. hold Results Elevated Rates of Protein Synthesis Sustain the Myc-Dependence Metabolic Program To assess the role of Myc-dependent increases in protein synthesis on cellular metabolism, the Eμ-Myc mouse model of B cell lymphoma was utilized. The Eμ-Myc/+ transgenic mouse faithfully recapitulates the clinical features of Burkitt's lymphoma (Adams, 1985, Nature 318:533-538; Harris et al., 1988, J. Exp. Med. 167:353-371). Eμ-Myc splenic B lymphocytes have increased rates of Myc-dependent ribosome biogenesis and protein synthesis, resulting in increased cell growth, compared to B lymphocytes from wild-type counterparts (Barna et al., 2008, Nature 456:971-975; Iritani and Eisenman, 1999, Proc. Natl. Acad. Sci. 96:13180-13185). Previous studies have revealed that haploinsufficiency of a single ribosomal protein (RP), RPL24, leads to an overall decrease in protein synthesis, and that RPL24 haploinsufficiency in the Eμ-Myc/+ genetic background is sufficient to restrain Myc-dependent hyperactivation of protein synthesis to normal levels, dramatically thwarting Myc's oncogenic activity (Barna et al., 2008, Nature 456:971-975). To restore Myc-dependent increases in protein synthesis to normal levels, mice harboring the Eμ-Myc/+ transgene were intercrossed with a mouse Minute that is heterozygous for the ribosomal protein L24 (RPL24) gene and displays a slightly decreased protein synthesis capacity.

Figure 1B:
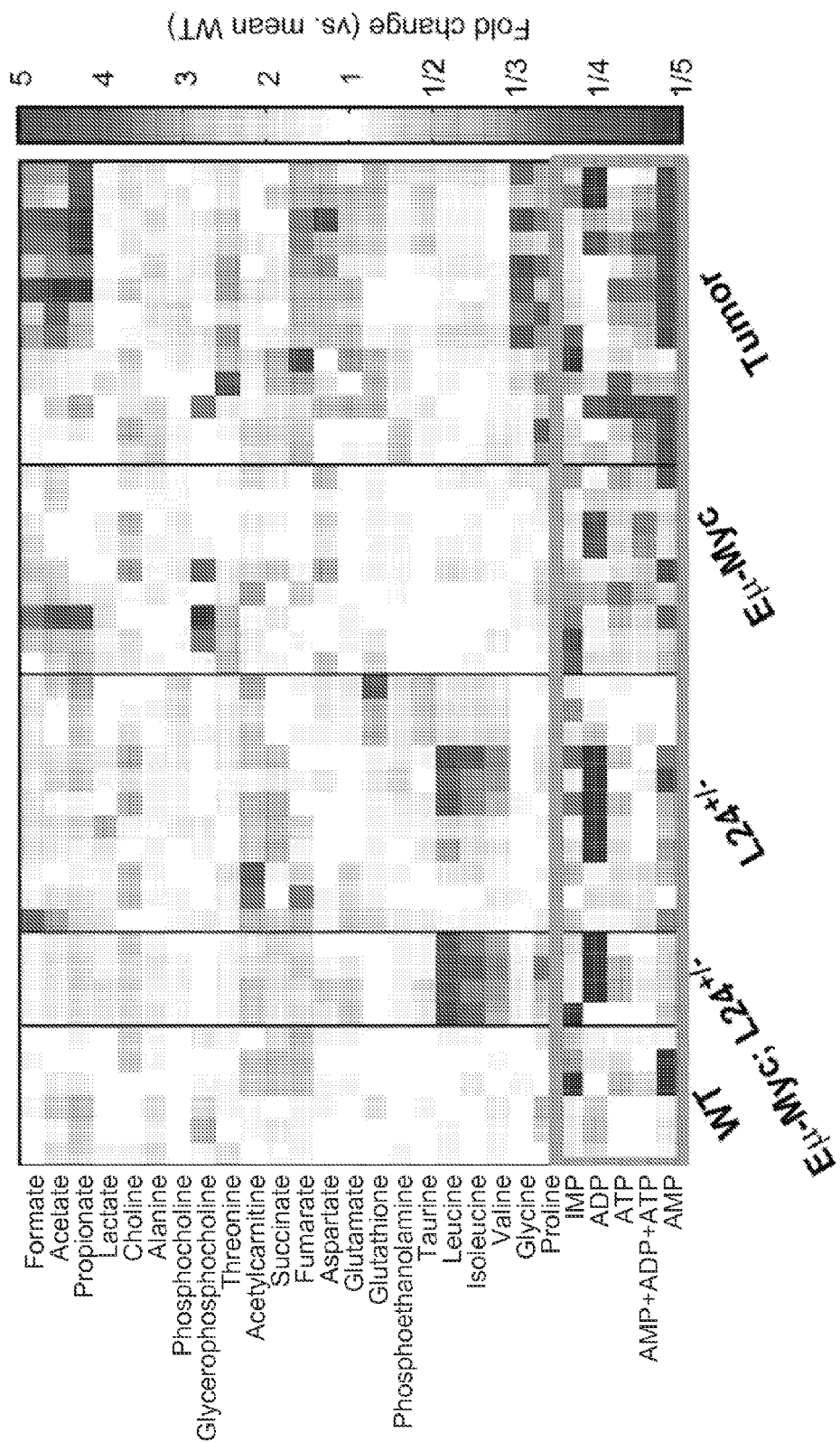

H-NMR was used to conduct an unbiased metabolomics approach to identify metabolite changes occurring as a result of Myc-induced increases in protein synthesis (FIG. 1A). Profiling studies of splenic B lymphocytes from 5 week old wild-type, Eμ-Myc/+, RPL24$^{BST/+}$, Eμ-Myc/+; RPL24$^{BST/+}$ and Eμ-Myc/+ tumor cells were performed. Myc-overexpressing cells, both in the pre-tumor and tumor setting, display an overall depletion in formate, acetate, and propionate, which are used for the construction of larger, more complex metabolites such as nucleotides, lipids, and amino acids (FIG. 1B). It was also shown that in the pre-tumor setting, Myc broadly increases the levels of metabolites frequently found increased in cancer cells such as purine nucleotides, choline, phosphocholine, acetylcarnitine and several amino acids such as glycine and proline (FIG. 1B). However, there also appears to be cell-type specificity. For example, the levels of glutamine or lactate previously linked to Myc-dependent metabolism are not altered in Eμ-Myc/+ B cells (Wise et al., 2008, Proc. Natl. Acad. Sci. 105:18782-18787; Yuneva et al., 2012, Cell Metab. 15:157-170). The changes observed in the pre-tumor setting are maintained and in most cases, amplified in the Myc-driven malignant lymphoma setting, suggesting that the alterations in the metabolic program observed in tumor cells are directly due to Myc hyperactivation.

Figure 1C:
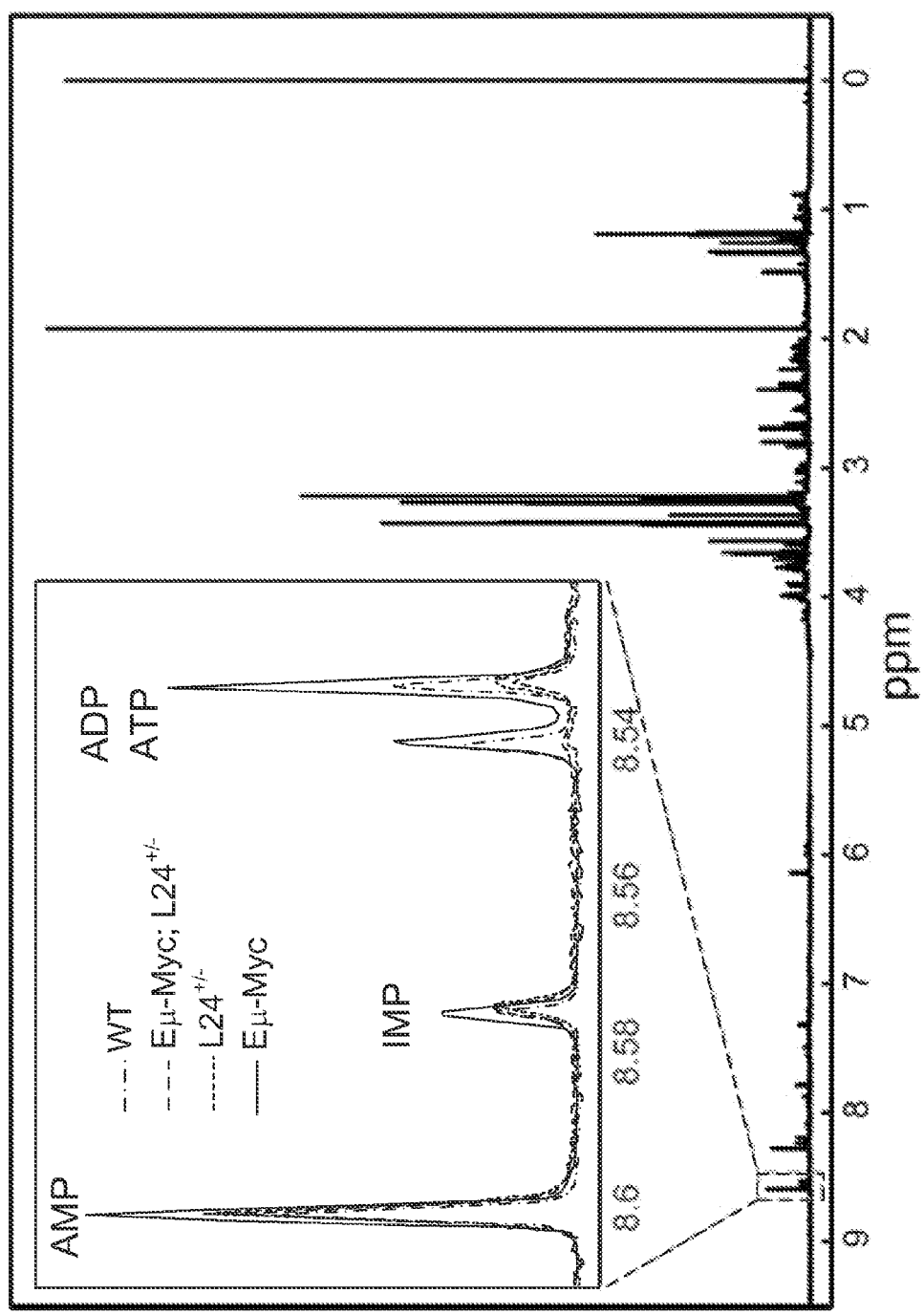
Figure 2A:
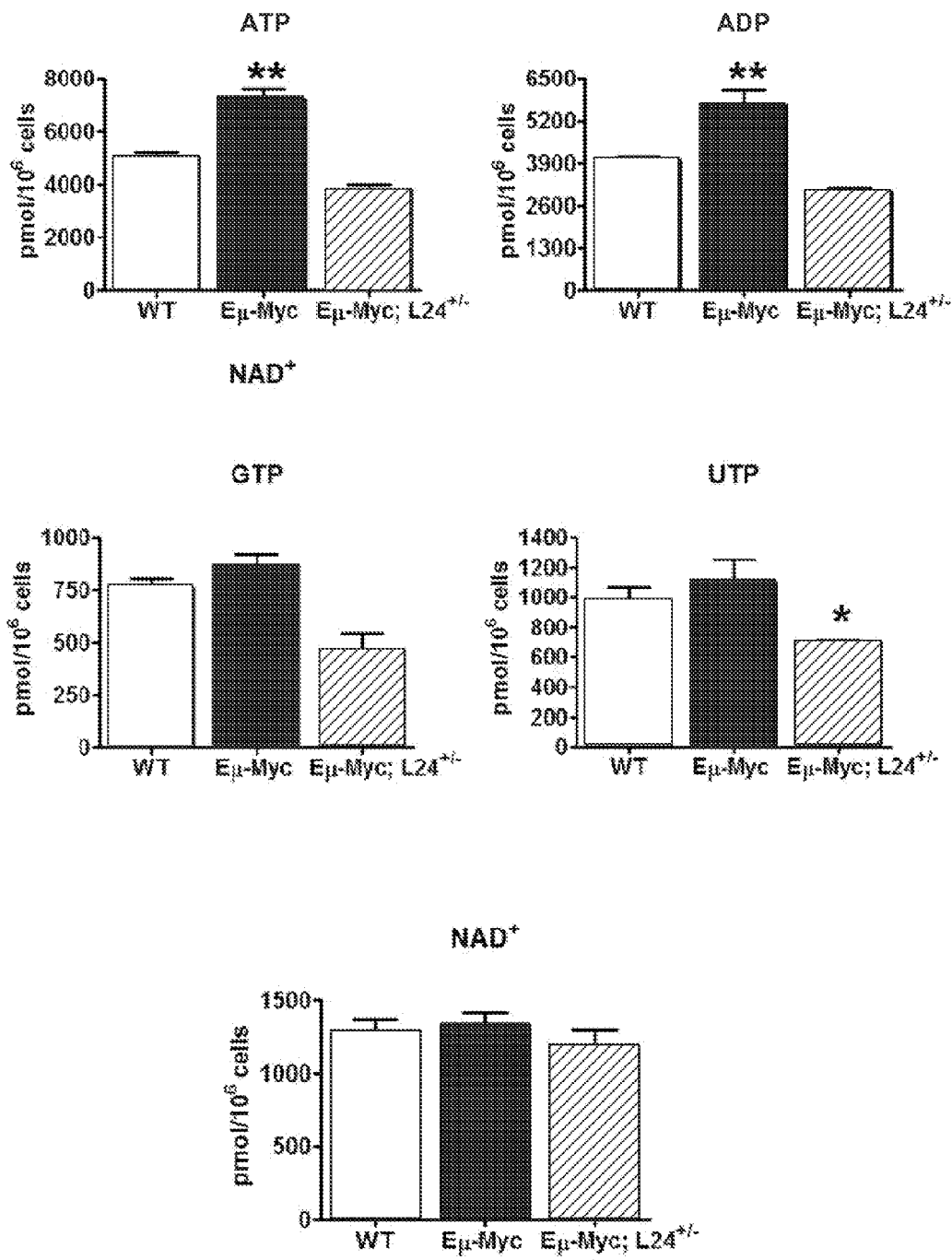
FIG. 2. Measurement of ribo- and deoxyribo-nucleotides in Myc overexpressing cells. (A) Measurement of various purine, pyrimidine, and pyridine ribonucleotides via HPLC. B) Measurement of deoxynucleotide triphosphates via [$^3$H] nucleotide PCR incorporation assay. *$P<0.05$, **$P<0.01$, N=3-6 mice per condition, error bars represent standard deviation.
Figure 2B:
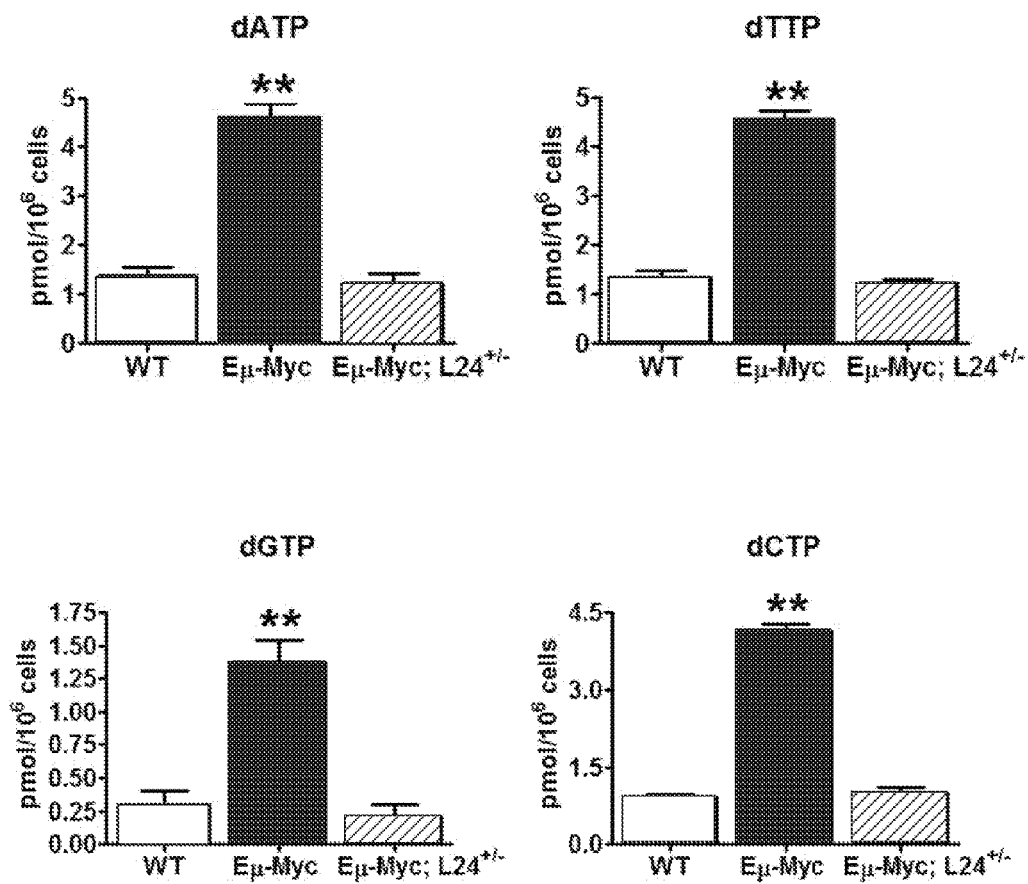

Profiling revealed a striking increase in purine nucleotide metabolites in B lymphocytes from Eμ-Myc/+ mice, which was recovered upon restoring protein synthesis rates to normal levels in Eμ-Myc/+; RPL24$^{BST/+}$ (FIG. 1B). Averaged H-NMR spectra demonstrate a specific increase in the levels of the purine nucleotides IMP, AMP, ADP, and ATP in Eμ-Myc B cells relative to wild-type that relies on Myc-induced protein synthesis (FIGS. 1B and 1C). The observed rescue in nucleotide metabolite production in Eμ-Myc/+ compared to Eμ-Myc/+; Rpl24$^{BsT/+}$ B cells was also further validated by HPLC (FIG. 2A) and a PCR-based assay to measure free dNTP concentrations from a complex mixture of intracellular metabolites (FIG. 2B). Together, these findings suggest that augmented protein biosynthesis may be directly coupled to the control of nucleotide metabolism downstream of Myc hyperactivation revealing an unexpected coordination between production of the two most abundant classes of macromolecules in cancer cells—proteins and nucleic acids.

PRPS2 is a Critical Rate-Limiting Enzyme Integrating Myc-Dependent Protein Synthesis with Nucleotide Metabolism Elevated nucleotide pools are a defining feature of many cancer cells, and are required to carry out a diverse array of cellular functions (Tong et al., 2009, *Curr. Opin. Genet. Dev.* 19:32-37). In order to promote increased biomass and growth, cells must induce a concerted increase in the production of nucleotides through either de novo synthesis from carbohydrate and amino acid precursors or by salvage enzymes that rejoin recycled nucleobase and sugar moieties. The effect of Myc on nucleotide levels was determined to be due, in large part, to increases in rates of de novo purine biosynthesis as revealed by the increased incorporation of radiolabeled precursors ([$^{14}$C]-formate) for the de novo synthesis pathway (FIG. 1D). It was also shown that Myc increases nucleotide production by promoting flux through the purine salvage pathway (FIG. 1E). Overall, results of these metabolic flux experiments suggest that Myc-dependent control of purine nucleotide concentrations relies on the increased biosynthetic production of purine precursors.

To identify Myc regulated genes that could explain alterations in the levels of IMP, AMP, ADP, and ATP observed in the metabolic profiling study, RT-PCR and Western blotting were employed to screen candidate nucleotide biosynthetic pathway genes. Using this approach, PRPS2 was identified as a candidate gene that displayed increased expression levels in Eμ-Myc/+ B cells that were restored to wild-type levels in Eμ-Myc/+; RPL24$^{BST/+}$ B cells (FIGS. 1F and 1G). Notably, other key regulated genes involved in purine biosynthesis were not restored to wild-type levels in Eμ-Myc/+; RPL24$^{BsT/+}$ B cells. mRNA levels of PRPS2 were induced to similar levels in both Eμ-Myc/+ and RPL24$^{BsT/+}$, suggesting a post-transcriptional mechanism of gene expression (FIG. 1G). Notably, haploinsufficiency of RPL24 did not impinge upon the transcriptional program of Myc. Therefore, these results unexpectedly suggest that one key enzyme within the purine biosynthetic pathway may be directly coupled to increased rates of protein synthesis elicited by the Myc oncogene to further regulate the flow of metabolic intermediates through the entire nucleotide pathway.

Figure 3A:
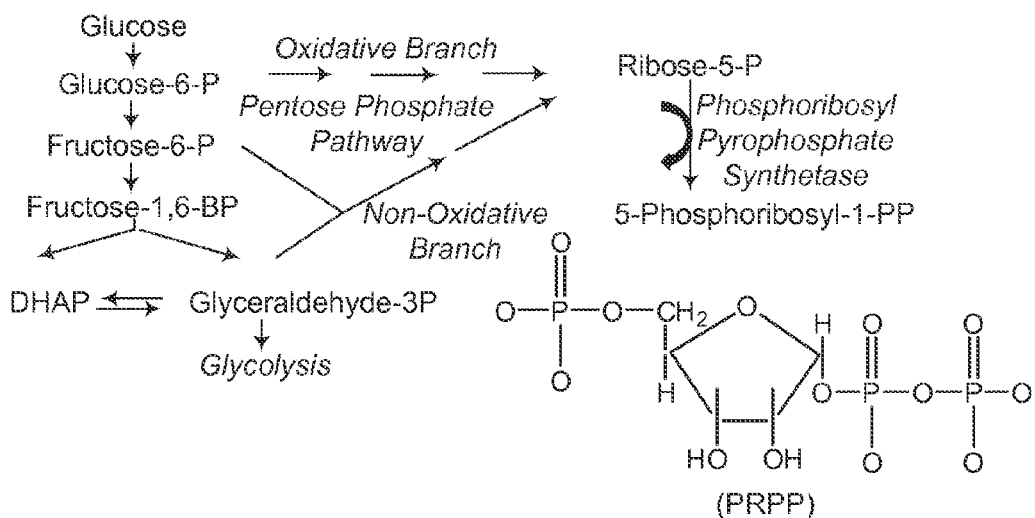
FIG. 3. PRPS2 is a rate-limiting enzyme for purine synthesis and salvage pathways. (A) Schematic of the pathway of PRPP biosynthesis produced from glucose. (B) Western blot of primary wild-type B cells transduced with control or Prps2 siRNA. (C) Western blot of primary wild-type B cells mock transfected or transfected with capped, polyadenylated Prps2 encoding mRNA. (D) Schematic illustrating [$^{14}$C] formate incorporation into de novo purine biosynthesis pathway. (E) Measurement of [$^{14}$C] formate incorporation into cells treated as in (B). (F) Measurement of [$^{14}$C] formate incorporation into cells treated as in (C). (G) Schematic illustrating [8-$^{14}$C] hypoxanthine incorporation into purines via HPRT nucleotide salvage enzyme. (H) Measurement of [8-$^{14}$C] hypoxanthine incorporation into cells treated as in (B). (I) Measurement of [8-$^{14}$C] hypoxanthine incorporation into cells treated as in (C). For all experiments, error bars represent standard deviation, N=6, * denotes $p<0.05$, ** denotes $p<0.01$ FIG. 4. PRPS2 is highly expressed in oncogenic cells and human lymphoma. (A) Western blot analysis of PRPS2 in B lymphocytes isolated from spleens of mice of the indicated genotypes. (B) Western blot analysis of PRPS2 in primary mouse embryo fibroblasts untransformed (WT) or transformed by forced overexpression of Myc and Ras (Myc+ Ras). (C) Comparative gene expression analysis of PRPS2 mRNA levels from various normal patient cells (1-5) or patients with centroblastic lymphoma (6). 1=B lymphocyte, 2=Centroblast, 3=Memory B lymphocyte, 4=Native pre-germinal center B lymphocyte, 5=Small cleaved follicle center cell, 6=Centroblastic lymphoma cells.
Figure 3B:
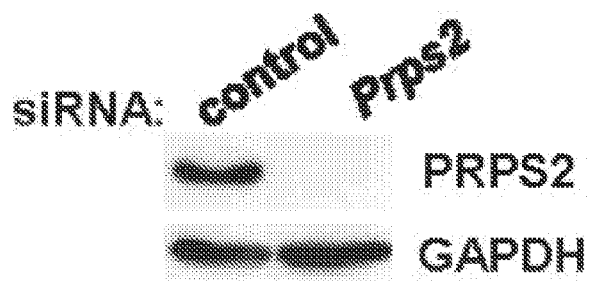
Figure 3C:
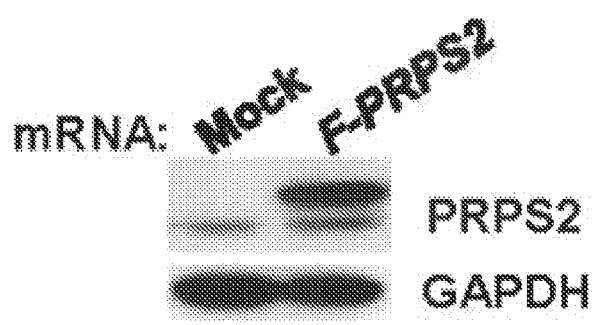
Figure 3D:
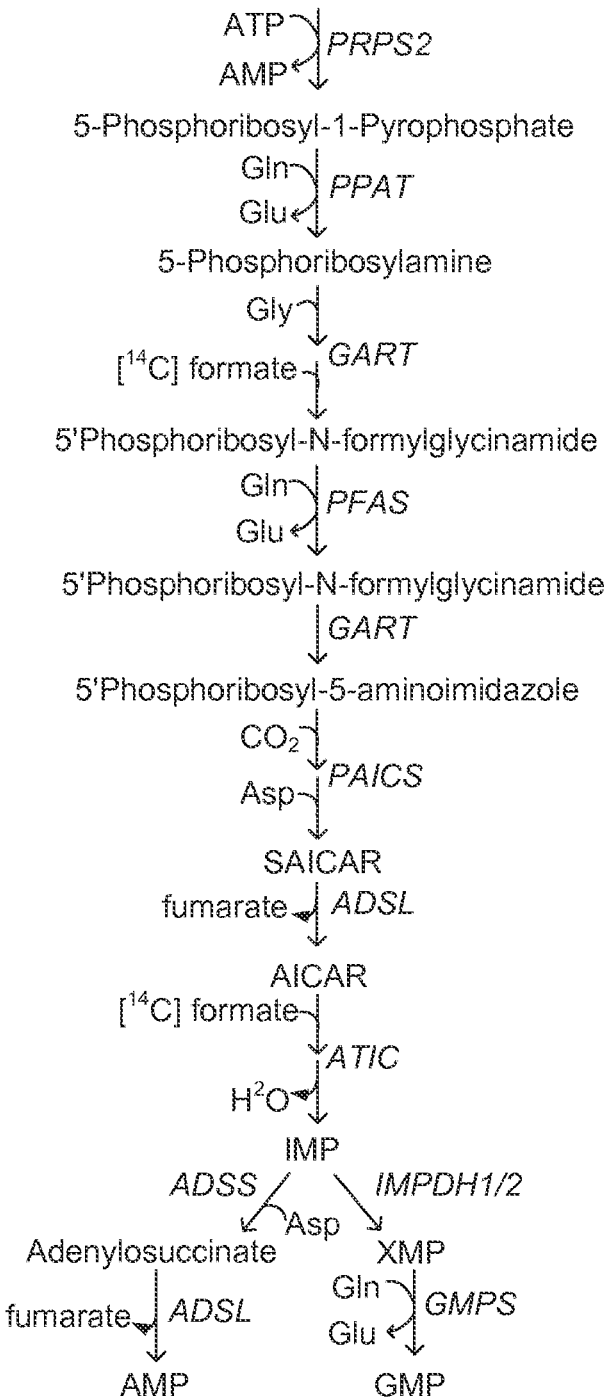
Figure 3G:
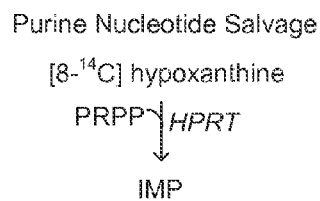
Figure 3H:
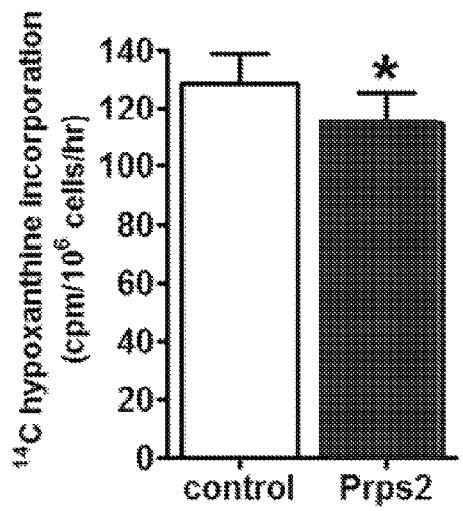
Figure 3I:
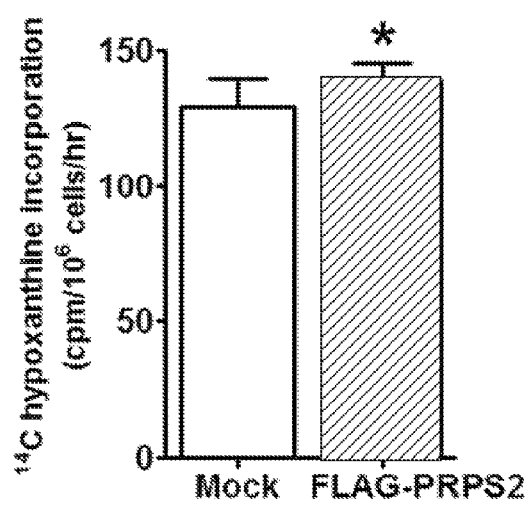

PRPS2 is one of two isoforms of phosphoribosyl pyrophosphate synthetase that are widely expressed in many tissues. PRPS2 catalyzes the rate-limiting step in nucleotide biosynthesis and is thought to be expressed preferentially in highly proliferative cells and tissues. The PRPS2 enzyme adds a pyrophosphate group donated from ATRP to ribose-5-phosphate generated from the pentose phosphate pathway to produce 5-phosphoribosyl-1-pyrophosphate (PRPP) (FIG. 3A). PRPP is a substrate for all nucleotide salvage pathway enzymes as well as the rate-limiting enzymes of purine and pyridine biosynthesis. Since the Km rate constants of nucleotide biosynthetic pathway enzymes that utilize PRPP as a substrate far exceed the physiological intracellular concentrations of this metabolite, an increase in PRPP levels may be sufficient to govern the overall nucleotide biosynthetic rate of cells. Therefore, whether PRPS2 as a single enzyme is necessary and sufficient to control the overall purine biosynthesis and salvage rates of cell was determined. Prps2 expression levels were directly modulated in freshly isolated primary B cells (FIGS. 3B and 3C). Upon knockdown of Prps2 expression in primary B cells using siRNA, a 14% decrease in the rate of [$^{14}$C] formate incorporation into purines was observed compared to control siRNA transfected cells (FIGS. 3D and 3E) demonstrating the requirement of PRPS2 enzymatic activity for the optimum rate of de novo purine biosynthesis. Conversely, overexpression of Prps2 in B cells caused a 21% increase in [$^{14}$C] formate incorporated into purine nucleotides (FIG. 3F). To assess the contribution of PRPS2 activity towards nucleotide salvage pathway function, [8-$^{14}$C] hypoxanthine labeling of purines upon knockdown or overexpression of Prps2 in B cells was employed (FIG. 3G). Although less dramatic than the effect observed on de novo purine biosynthesis, both knockdown (FIG. 3H) as well as overexpression (FIG. 3I) resulted in significant decreases or increases, respectively, in [$^{14}$C] incorporation.

Figure 4B:
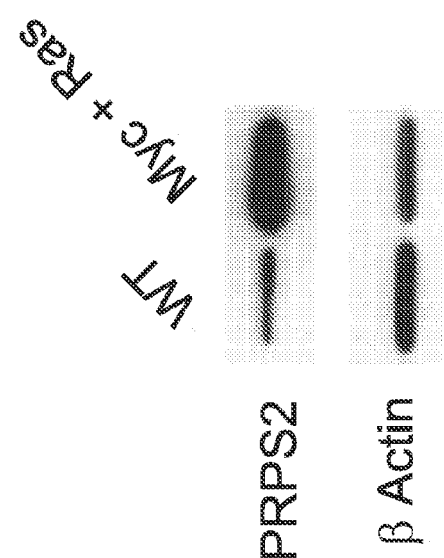
Figure 4A:
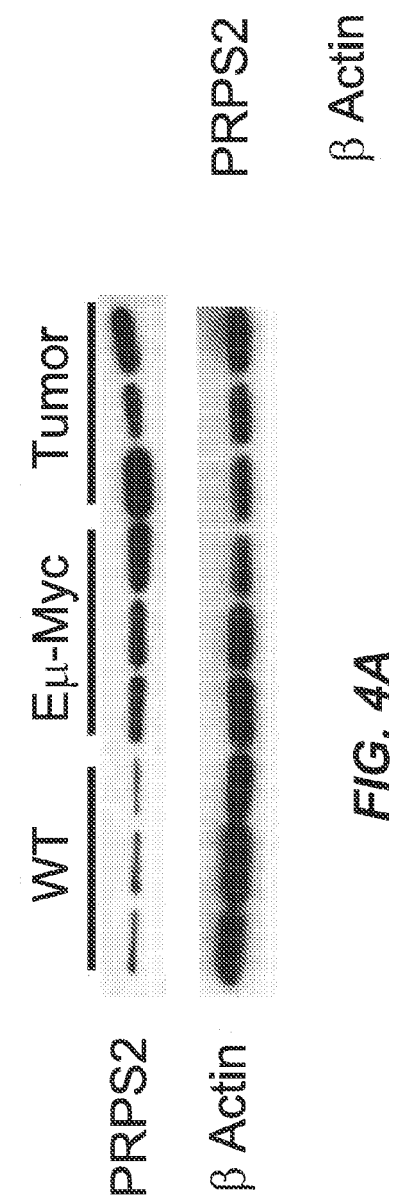
Figure 4C:
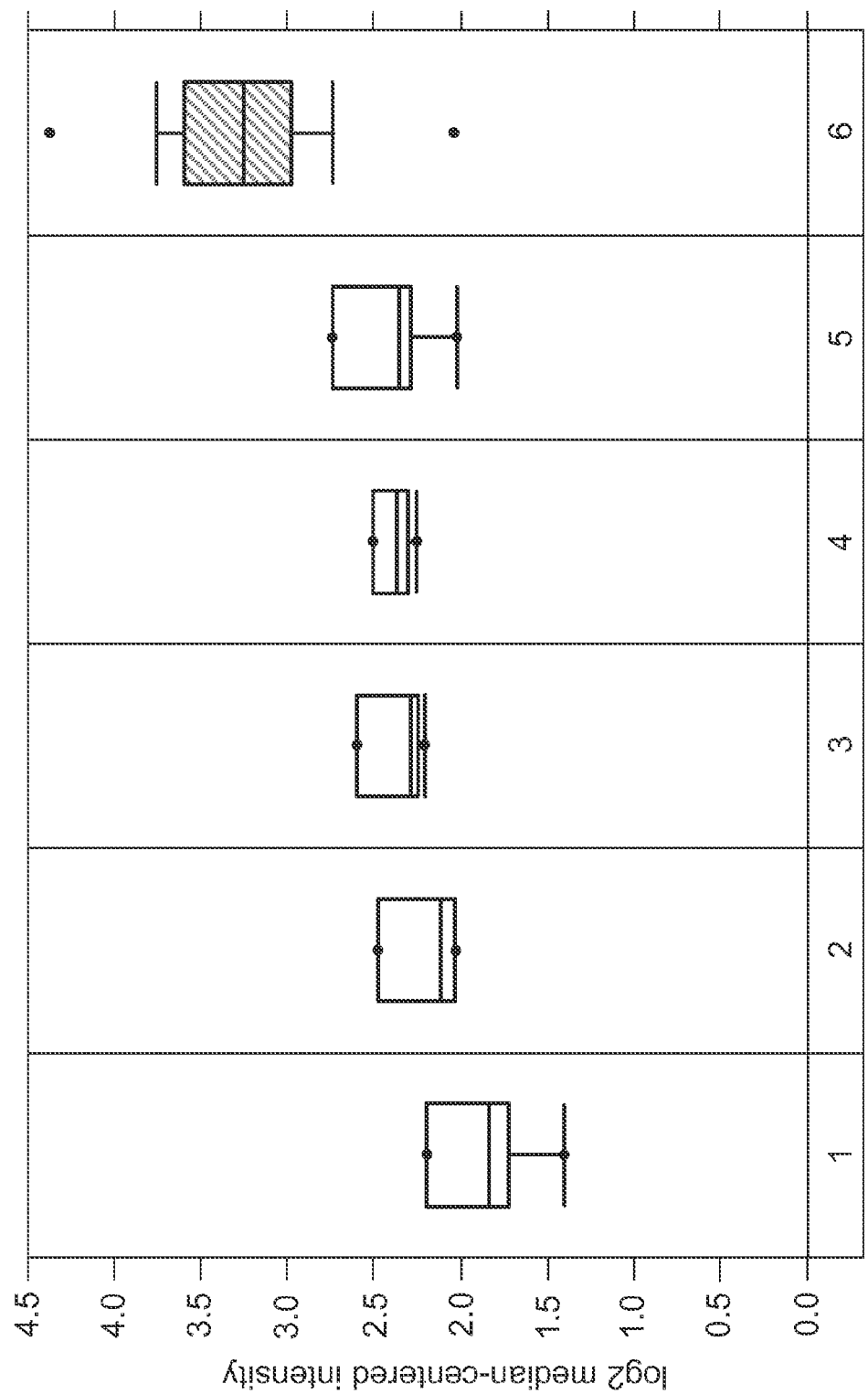

The results of these metabolic flux experiments demonstrate that PRPS2 levels are rate limiting and important for controlling nucleotide biosynthesis rates, revealing a key enzyme that promotes nucleotide metabolism and is regulated at the post-transcriptional level by Myc hyperactivation during oncogenic insult. Consistent with this hypothesis, PRPS2 levels were found to be increased in Eμ-Myc cells and tumors (FIG. 4A) as well as in mouse embryo fibroblasts oncogenically transformed with Myc and Ras (FIG. 4B). Human lymphoid tumors also displayed increased PRPS2 expression levels relative to normal human tissue. Using the Oncomine expression database and a previously published dataset containing 336 samples, it was discovered that PRPS2 fell within the top 3% of all genes overexpressed in centroblastoid lymphoma with a highly significant p value of 2.76×10$^{-12}$ (FIG. 4C).

Figure 5A:
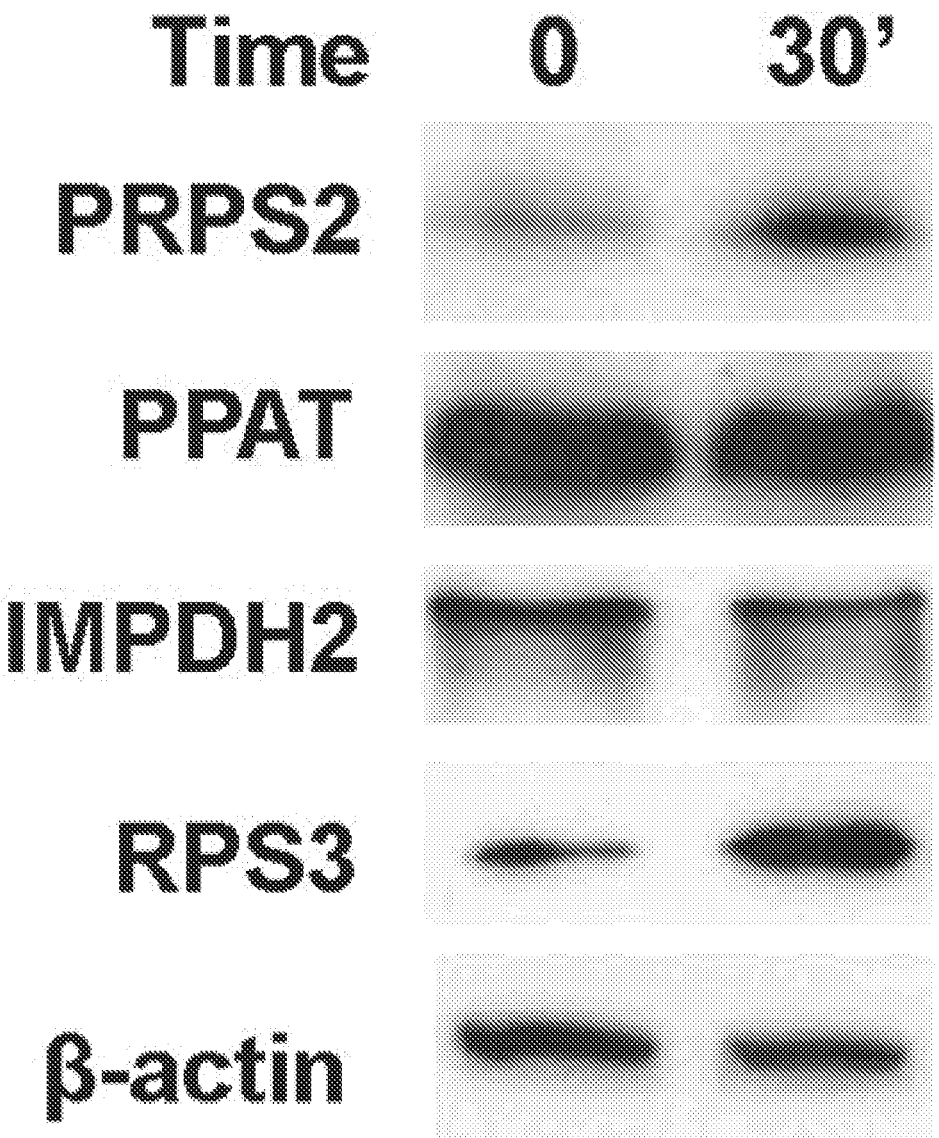
FIG. 5. PRPS2 is regulated acutely at the translational level. (A) Western blot analysis using the indicated antibodies against purine biosynthesis enzymes for NIH3T3 cells serum-starved for 48 hr-/+ treatment with 20% FBS for 30 min. (B) qRT-PCR analysis of mRNA levels of indicated enzymes from cells under conditions as described in (A). (C) RT-PCR analysis of polysome-associated PRPS2 and PRPS1 mRNA in cells under conditions described in (A). The polysomal association of PRPS2 mRNA was tested by fractionating cytoplasmic lysates through a sucrose gradient and measuring mRNA abundance by qRT-PCR analysis in each of the 14 resulting fractions. Graph shows the relative levels of PRPS2 and PRPS1 mRNA in each gradient normalized to the corresponding 5S rRNA levels and expressed as a fraction of the total mRNA. Error bars represent standard deviation, N=4, *$P<0.05$. (D) Polysome profiles of serum starved and serum stimulated NIH3T3 cells treated as in (A).
Figure 5B:
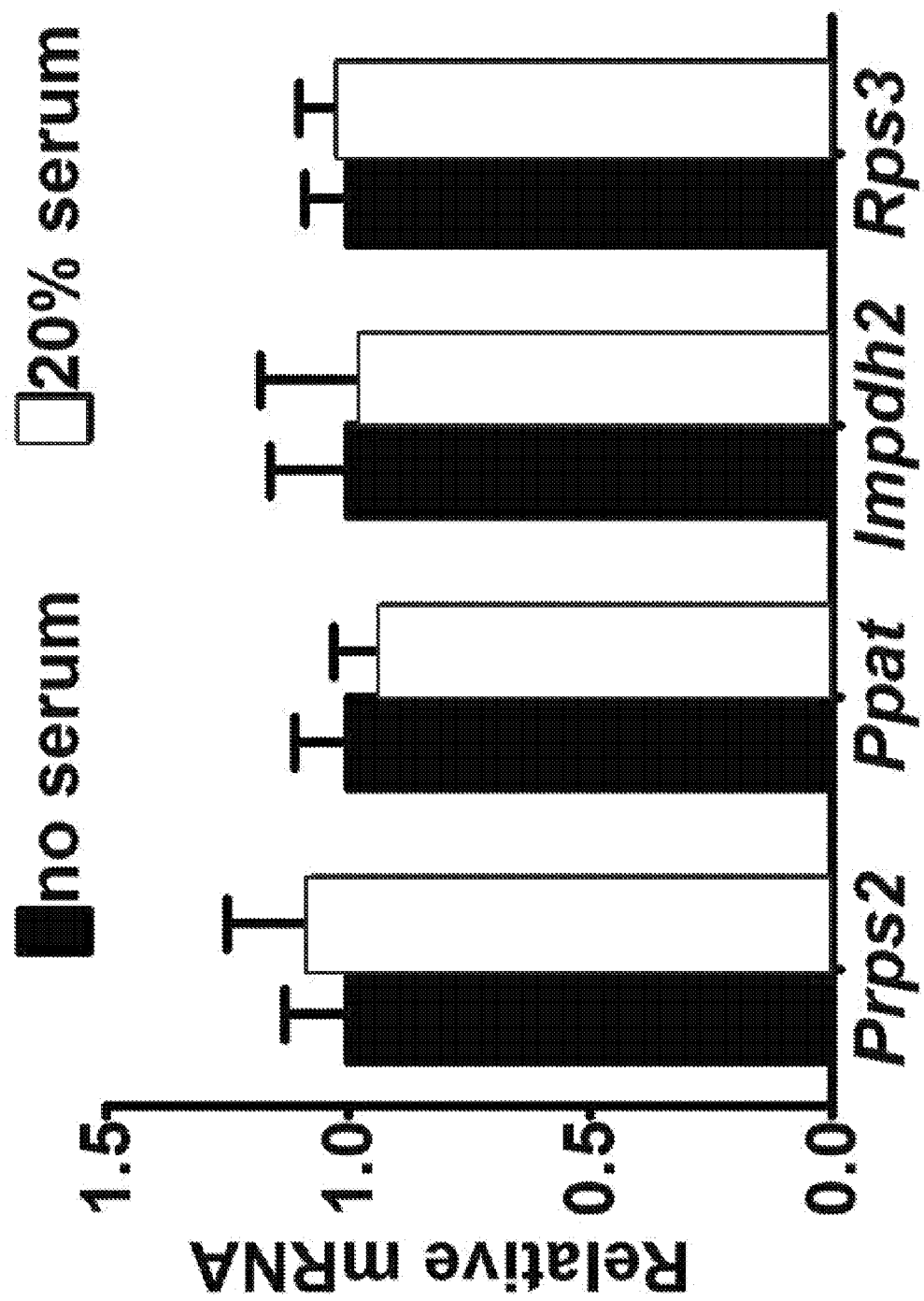
Figure 5C:
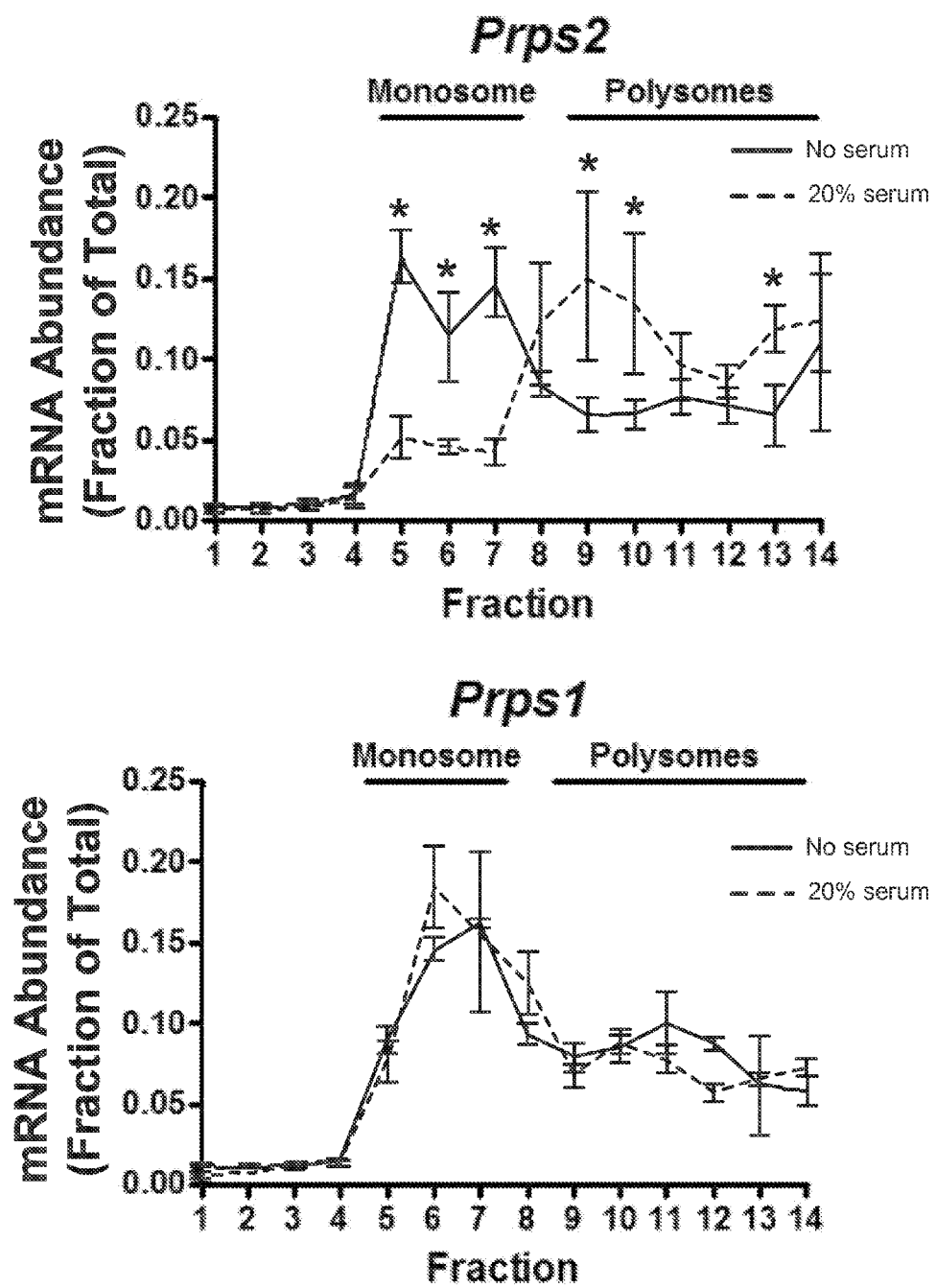
Figure 5D:
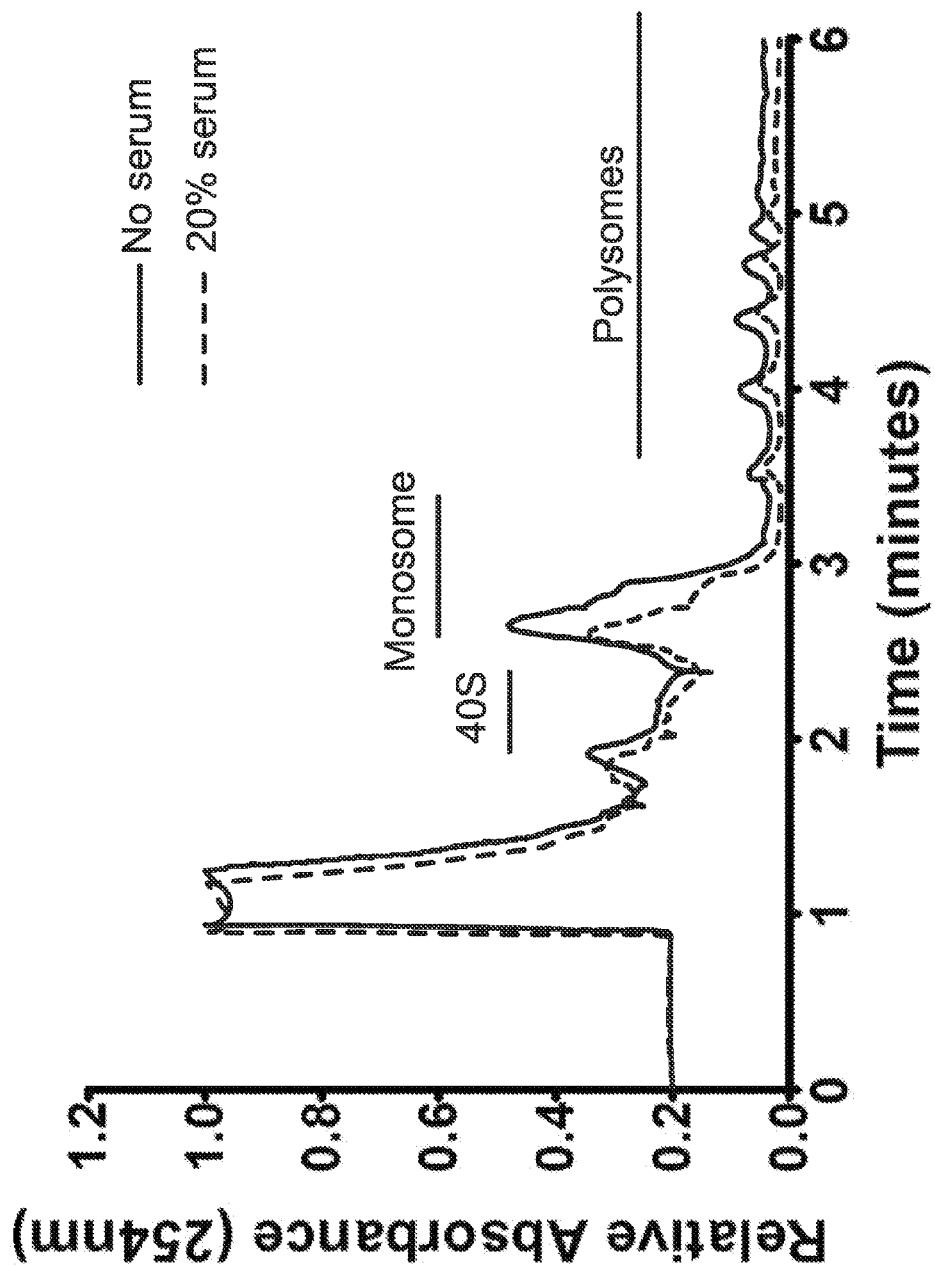

Prps2 but not Prps1 Gene Expression is Regulated Acutely at the Translational Level To determine whether PRPS2 was controlled at the translational level in normal cells, NIH3T3 cells were serum-starved for 48 hours and then protein synthesis was stimulated in the cells with 20% fetal bovine serum for 30 minutes (Geyer et al. 1982, *Mol. Cell Biol.* 2:685-693). Upon activation of cells with serum, PRPS2 protein levels were induced (FIG. 5A), whereas PRPS2 mRNA levels remained unchanged (FIG. 5B), suggesting regulation of PRPS2 expression occurs post-transcriptionally. To test whether the serum-induced expression was the result of increased translation, polyribosome-associated RNA was isolated and RT-PCR analysis was performed to measure PRPS2 levels. Increased levels of polysome-associated PRPS2 mRNA were observed compared to serum-starved cells, indicating that increased levels of PRPS2 observed after 30 minutes of serum stimulation were a result of enhanced translation of PRPS2 mRNA (FIGS. 5C and 5D). Moreover, Prps2 showed the same acute translational activation as Ribosomal Protein (S3) (Rps3), a bona fide translationally regulated mRNA that responds immediately and rapidly to acute serum stimulation.

While there are two isoforms of PRPP synthetase expressed in somatic tissues, only Prps2, and not Prps1, displays increased translation upon serum-stimulation (FIG. 5C). Interestingly, the PRPS2 isoform is largely resistant to feedback inhibition by the nucleotide biosynthesis products ADP and GDP that is a feature of the PRPS1 enzyme (Nosal et al., 1993, *J. Biol. Chem.* 268:10168-10175). This enzymatic property of PRPS2 may facilitate the unrestrained, elevated production of nucleotides observed in Myc-overexpressing cells as well as explain why the levels of PRPS2 but not PRPS1 are increased in cancer cells. The translational regulation of Prps2 is highly specific, as other members of the purine biosynthetic pathway are not regulated in this manner (FIG. 5A). Therefore, translational control of Prps2 is a rapid sensor of the total rate of protein biosynthesis within the cell, which precedes biomass accumulation.

Figure 6A:
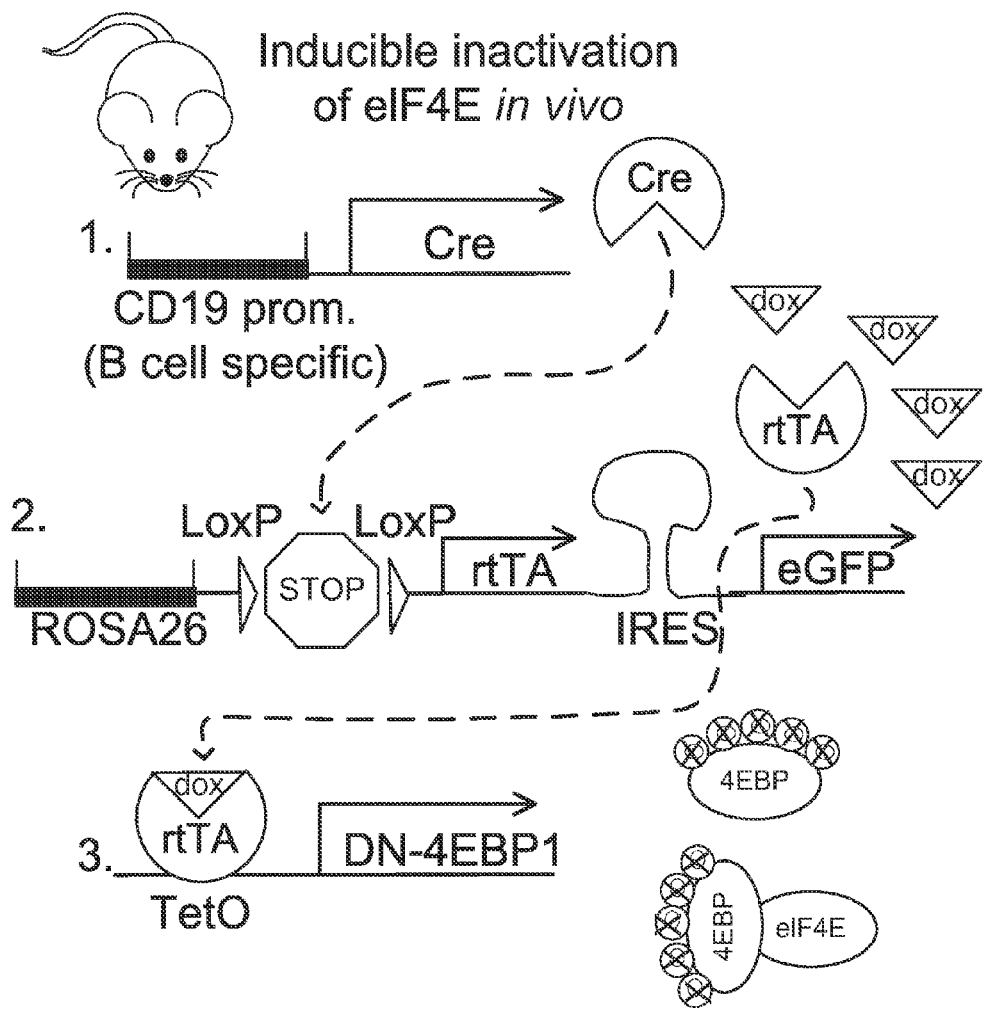
FIG. 6. PRPS2 mRNA translation, but not Prps1, is regulated via a cis tegulatory motif in its 5' UTR by the eIF4E oncogene. (A) Schematic representing compound transgenic mice utilized to drive inducible expression of dominant-negative-4EBP1 (DN-4EBP1) specifically in B lymphocytes. (B) Western blot analysis of indicated purine biosynthesis enzymes from protein lysates derived from splenic B lymphocytes isolated from inducible DN-4EBP1 mice described in (A)-/+ intraperitoneal doxycycline administration for the indicated times. (C) qRT-PCR measurement of indicated mRNA levels from cells treated as in (B). (D) Luciferase reporter assay of transiently-transfected 293T cells expressing the indicated constructs. Error bars represent standard deviation, N≥3, * $p<0.05$. (E) Luciferase reporter assays of NIH3T3 cells co-transfected with the indicated 5'UTR reporter construct and a plasmid expressing either empty vector or DN-4EBP1. Error bars represent standard deviation, N=4, ***$P<0.001$ by student's t-test.
Figure 6B:
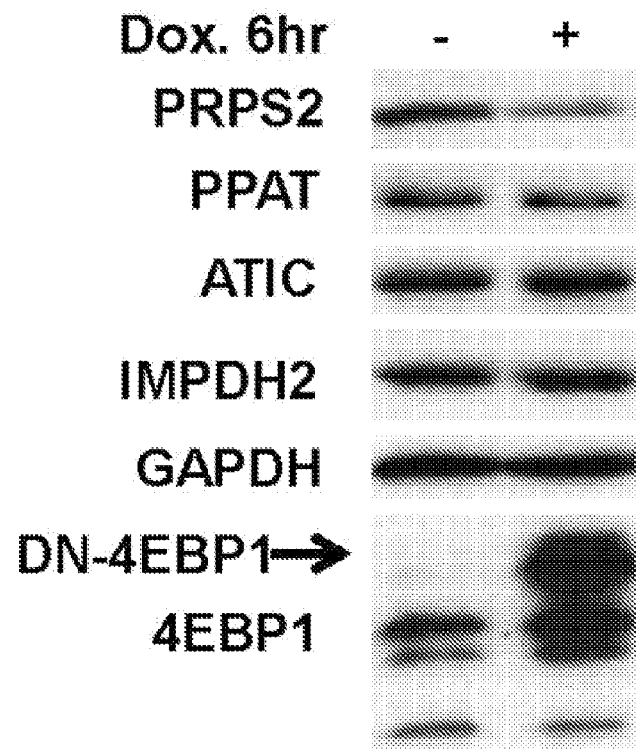
Figure 6C:
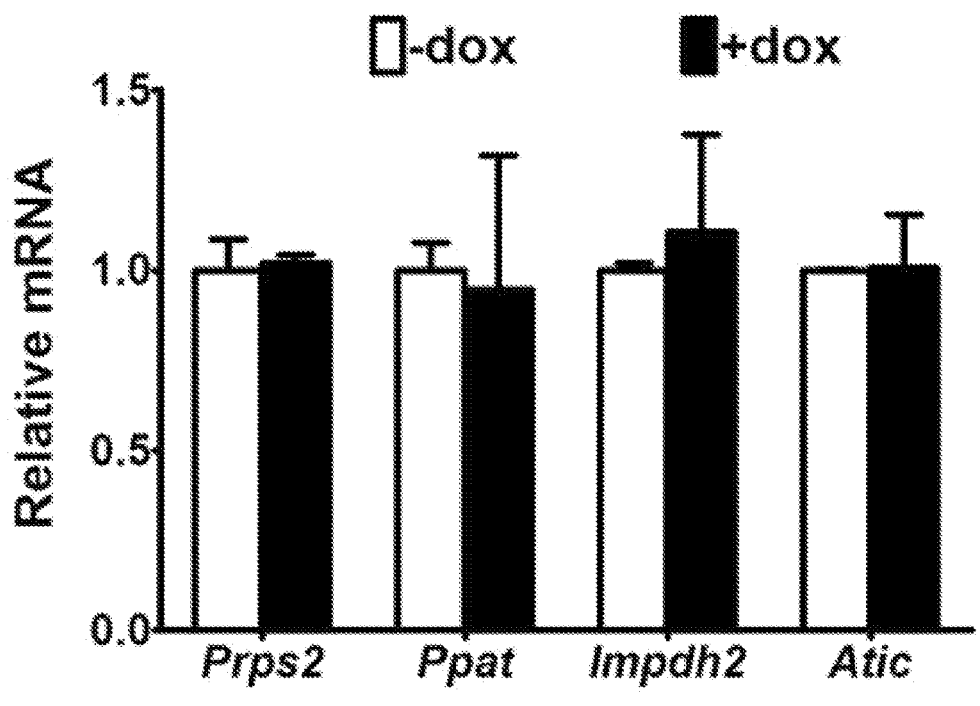
Figure 6D:
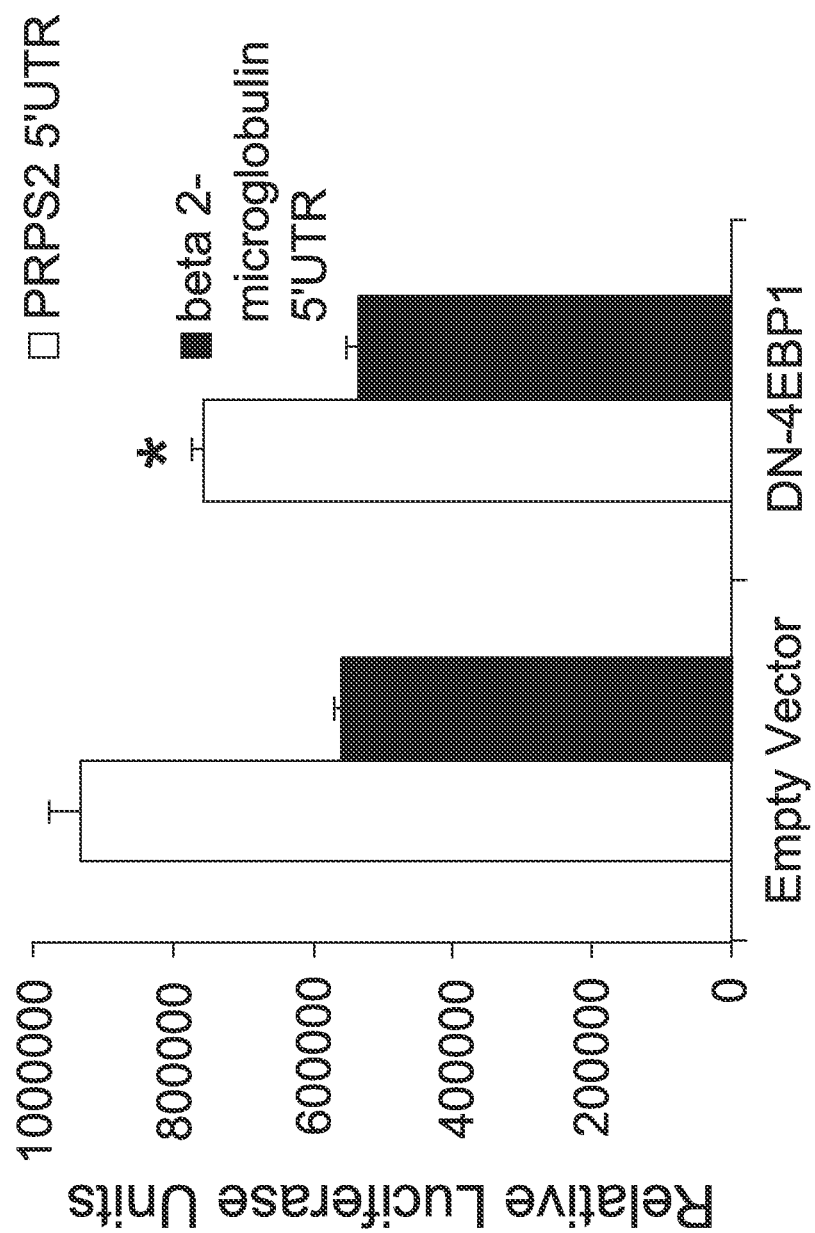

PRPS2 Translation is Controlled by the eIF4E Oncogene Through a Conserved Cis-Acting Regulatory Element An outstanding question is how Prps2, but not other members of the purine biosynthesis pathway, is specifically and acutely regulated at the translation level downstream of Myc hyperactivation. Pro-growth signals such as serum stimulation and Myc hyperactivation are thought to regulate translation of specific subsets of mRNAs through increases in the activity of the major cap-binding protein, eIF4E (Topisirovic and Soneneberg, 2011, *Cold Spring Harb. Symp. Quant. Biol.* 76:355-367; Hsieh and Ruggero, 2010, *Clin. Cancer. Res.* 16:4914-4920). Importantly, eIF4E is also a direct transcriptional target of Myc (Jones et al., 1996, *Mol. Cell. Biol.* 16:4754-4764) and is a master regulator of the rate-determining step in translation initiation. Therefore, whether the effects of Prps2 translational control are mediated through eIF4E hyperactivation was tested. To this end, a genetic system to specifically express a doxycycline-inducible dominant negative eIF4E binding protein 1 (DN-4EBP1) transgene in B cells (FIG. 6A) was employed in order to decrease eIF4E activity in vivo (Hsieh et al., 2010, *Cancer Cell* 17:249-261; Pourdehnad et al., 2013, *Proc. Natl. Acad. Sci.* 110:11988-11993). This genetic strategy does not perturb global protein synthesis nor cell viability, but rather only affects the translation of eIF4E rate-limiting target mRNAs. Strikingly, the inducible downregulation of eIF4E activity decreased expression of PRPS2 protein (FIG. 6B) without affecting Prps2 mRNA levels (FIG. 6C). The eIF4E-dependent translational control within the nucleotide biosynthesis pathway is selective for Prps2 as the expression levels of additional key enzymes in this pathway such as IMPDH2, PPAT, and ATIC remain unchanged in DN-4EBP1 transgenic mice.

Figure 6E:
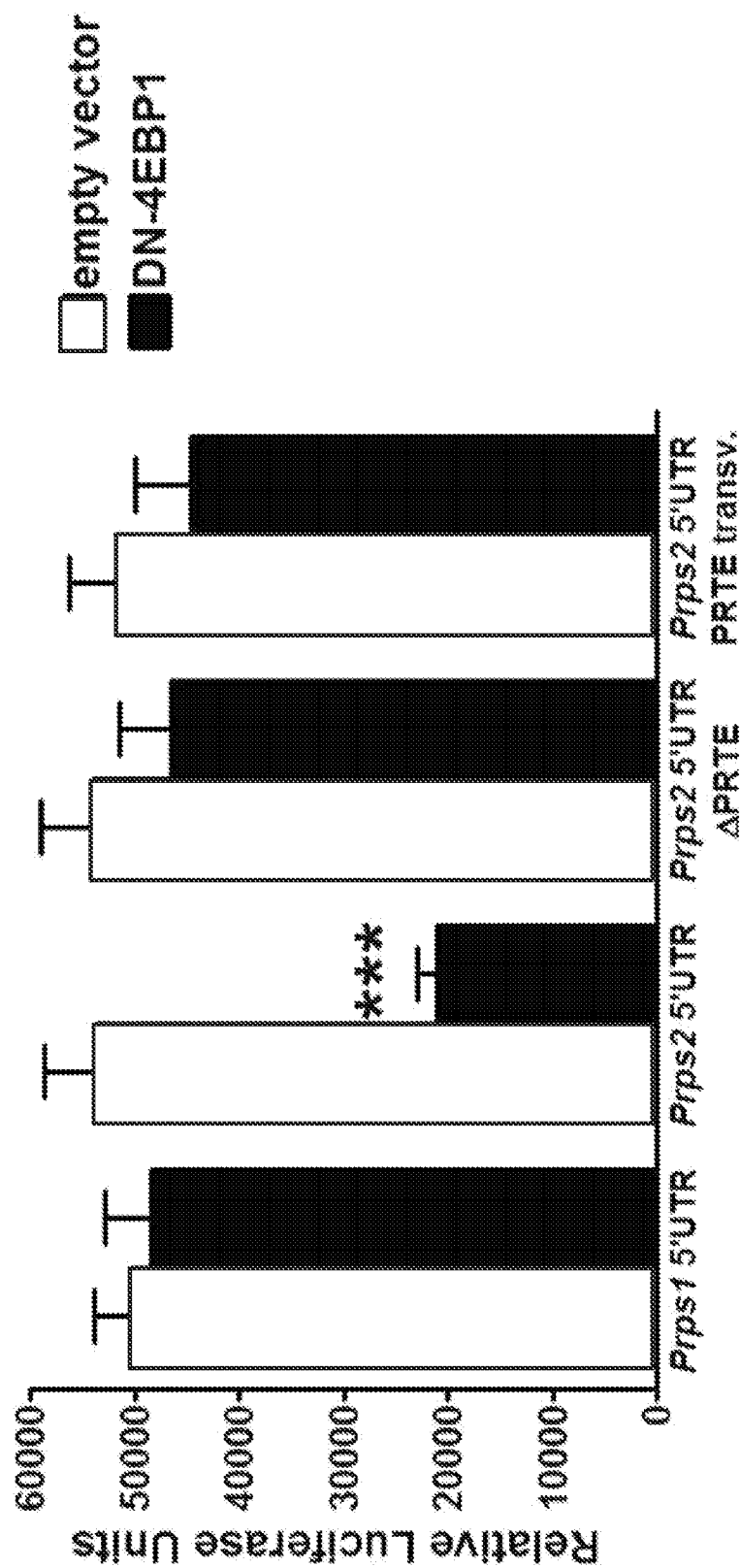

To further understand the mechanisms by which Prps2 is selectively sensitive to translational regulation by eIF4E, a specific element or motif within the 5' UTR was tested for its role in translational regulation of Prps2. A recently identified, important eIF4E cis-regulatory element that confers translational specificity is the pyrimidine-rich translational element (PRTE) (Hsieh et al., 2012, *Nature* 485:55-61). Consistent with our findings that PRPS2, and not PRPS1, is regulated at the level of translational control, only Prps2 contains a consensus PRTE motif within its 5' UTR (FIGS. 7A-B). Lucierfase reporter constructs fused to the 5' UTR of Prps1, Prps2, as well as deletion and transversion mutants of the PRTE motif within Prps2 were constructed. Strikingly, transfection of these reporter constructs revealed that the PRTE motif is sufficient to direct translational control of Prps2 in an eIF4E-dependent manner and that the related PRPS1 isoform is not translationally controlled by eIF4E (FIG. 6E). Importantly, other genes of the nucleotide biosynthesis pathway lack this motif within their 5' UTRs (FIGS. 7A-B and data not shown) demonstrating exquisite specificity for the eIF4E-dependent PRTE element in regulating Prps2 mRNA translation. Thus, Prps2 possesses a unique translational enhancer element within its 5' UTR, and the amount of PRPS2 present in cells can therefore be viewed as a critical bottleneck in the production of nucleotides in cancer that is coupled to protein synthesis.

Figure 8A:
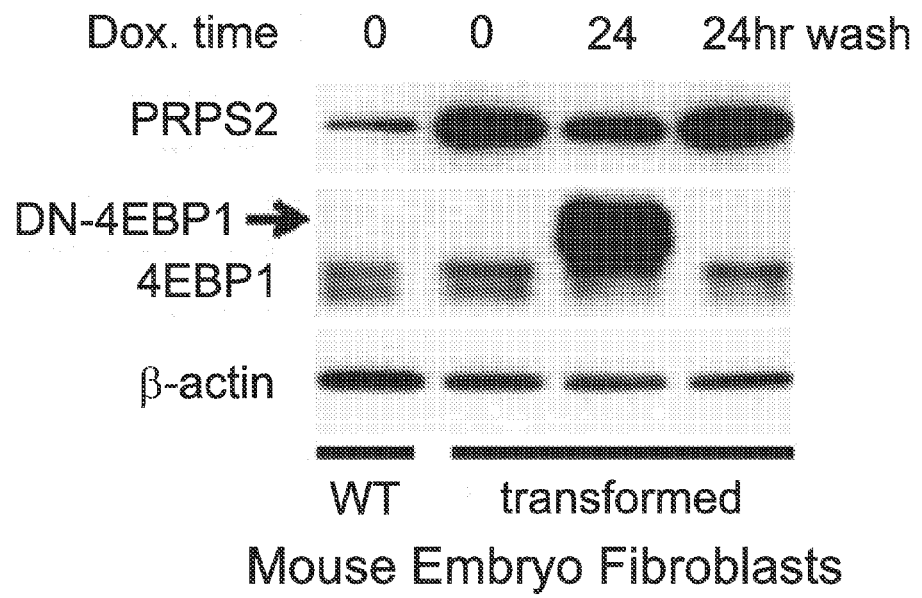
FIG. 8. Loss-of-function of PRPS2 leads to apoptosis of cancer cells and delays Myc-dependent tumor initiation and maintenance in vivo. (A) Western blot analysis of indicated proteins from lysates derived from wild-type ("WT") or oncogene-transformed ("Myc+Ras") mouse embryo fibroblasts harboring inducible DN-4EBP1 allele treated as indicated. 24 hr wash represents sample with replenished media lacking doxycycline. (B) Western blot analysis of SV40T-immortalized MEFs stably transduced with the indicated shRNA. (C) Wild-type or Myc+Ras transformed mouse embryo fibroblasts transduced with control or Prps2 siRNA for 48 hr were stained for Annexin V/Propidium Iodide (PI) and analyzed by FACS. Data in graph represents percent increase in Annexin V+/Propidium Iodide+Prps2 siRNA transfected cells relative to control siRNA transfected cells. Error bars represent standard deviation, N=4, **P<0.01. n.s.=not significant. (D) Splenic B lymphocytes cultured in vitro were transduced with palmitoylated GFP (pGFP) expressing retrovirus co-expressing either control or PRPS2-targeting shRNA and 48 hr post-tranduction, cells were stained with Annexin V/Propidium Iodide (PI) followed by FACS analysis. Data in graph represents percent increase in Annexin V+/PI+GFP_labeled Prps2 shRNA transduced cells relative to Annexin V+/PI+GFP-labeled control shRNA transduced cells. Error bars represent standard deviation, N=4, *P<0.05. (E) Western blot analysis using indicated antibodies on lysates prepared from B lymphocytes harvested from lethally irradiated wild type mice transplanted with bone marrow reconstituted from Eμ-Myc/+ fetal liver cells infected with a doxycycline-inducible PRPS2 shRNA and treated as indicated. Mice were given an intraperitoneal injection of vehicle (−) or 500 μl 1 mg/mL doxycycline and 24 hours later mice were sacrificed and B cells were isolated. (F) Annexin V/PI analysis of B lymphocytes harvested from mice treated as in (E). (G) Percent apoptotic cells represent Annexin V/PI+ percentage of GFP+ B lymphocytes prepared from mice treated as in (E). Error bars represent standard deviation, N=3 mice per group, **P<0.01. (H) Fetal liver-derived Eμ-Myc/+ hematopoietic stem cells were transduced with palmitoylated-GFP expressing retrovirus that co-express doxycycline (dox) inducible shRNA targeting Prps2 and subsequently transplanted to lethally-irradiated syngeneic mice. Survival curves measure days free of palpable lymph nodes between cohorts of mice treated with or without 2 mg/mL doxycycline in their drinking water. (I) Eμ-Myc/+ tumor cells were isolated from a lymphoma-bearing mouse, transduced with pGFP-expressing dox-inducible Prps2 shRNA, and subsequently transplanted into syngeneic mice. Five days post-transplantation, mice with GFP+ B220+ circulating cells were treated with vehicle or 2 mg/mL doxycycline in their drinking water. Survival curves begin at start of treatment regimen and monitor the time to sacrifice of tumor-bearing mice.
Figure 8B:
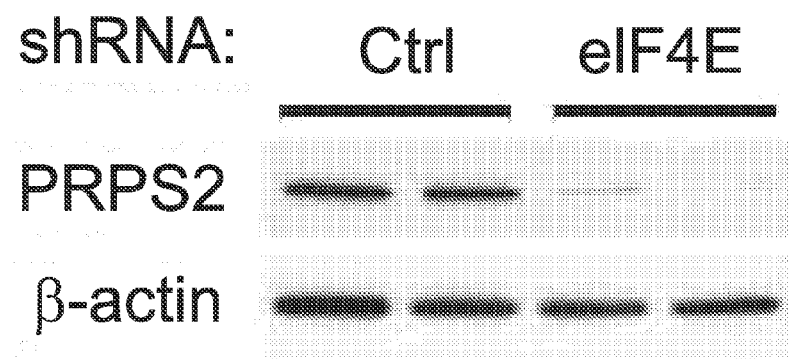

PRPS2 Activity is Synthetically Lethal in Myc-Overexpressing Cells and Required for Myc-Dependent Tumor Initiation and Maintenance In Vivo Although it is well established that oncogenic pathways promoter a high metabolic flux, it is rare to identify a specific node that is self-sufficient to control the flow of biosynthetic precursors to achieve this anabolic state. It was hypothesized that interference with the translational control of Prps2 mRNA could represent a key vulnerability in Myc-overexpressing cancer cells. It was tested whether inhibiting translational regulation of Prps2 mRNA could represent a potential synthetic lethal interaction with Myc hyperactivation. At first, it was asked whether translational regulation of eIF4E-dependent translational control of Prps2 is an integral response to the oncogenic transformation program. Primary mouse embryonic fibroblasts (MEFs) derived from compound transgenic mice, where the dominant negative 4EBP (DN-4EBP) allele is expressed in an inducible fashion, were used. In these cells, doxycycline administration drives DN-4EBP1 expression and eIF4E activity is specifically restrained. These MEFs were subsequently transduced with retroviral vectors overexpressing Myc and HRas$^{G12V}$ in order to induce cellular transformation. A dramatic increase in Prps2 translation was observed upon oncogenic cellular transformation drive by Myc and Ras that relies on eIF4E activity, demonstrating that translational regulation of Prps2 occurs as an early event during oncogenic transformation (FIG. 8A). This is consistent with the upregulation in PRPS2 protein during the early pre-tumor stage of Myc-driven lymphomagenesis (FIG. 1F).

Figure 8D:
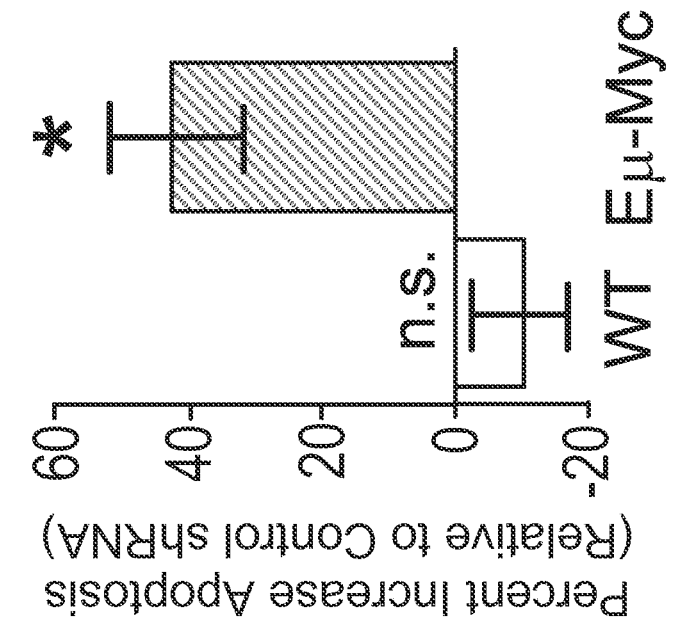
Figure 8C:
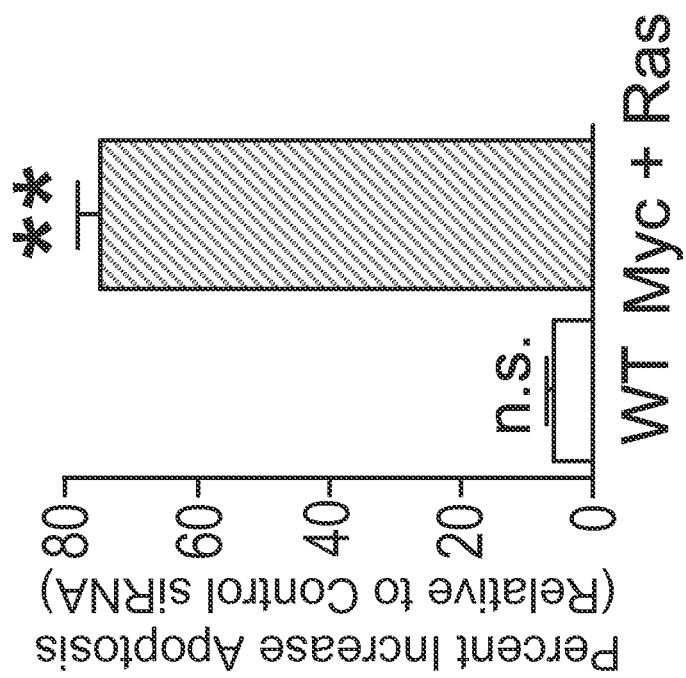

Given the specific upregulation of PRPS2 expression occurring downstream of both the Myc and mTOR/4EBP oncogenic pathways, the effect of loss-of-function of PRPS2 on cancer cells (Ras and Myc-transformed MEFs) was tested. Strikingly, knockdown of PRPS2 with siRNA induced a 70% increase in apoptosis of oncogene-transformed mouse embryo fibroblasts, but not untransformed wild-type mouse embryo fibroblasts, indicating a requirement for optimal PRPS2 function in cancer cells (FIG. 8C). Knockdown of Prps2 was also tested for whether it could confer synthetic lethality in premalignant Eμ-Myc/+ B cells. Similarly, a 40% induction of apoptosis assessed by Annexin V and propidium iodide staining was observed in Eμ-Myc B lymphocytes, but not wild type B lymphocytes, suggesting that PRPS2 may be necessary for survival of cells which harbor oncogenic lesions resulting in Myc hyperactivation (FIG. 8D). These results suggest that targeting PRPS2 may have important and selective therapeutic effects on either the initiation and/or maintenance of Myc-driven cancers, which are at present not druggable.

To test the role of loss-of-function of PRPS2 in human cancers, two Burkitt's lymphoma cell lines—Daudi and Raji, in which Myc is found translocated and overexpressed—were utilized. Burkitt's lymphoma is characterized by Ig enhancer chromosomal translocations to the c-Myc genomic locus that ultimately results in aberrantly high levels of Myc expression. Upon shRNA-mediated knockdown of PRPS2 in both Daudi and Raji cells, a significant induction of apoptosis was observed (FIG. 13B), revealing that PRPS2 expression is required to sustain enhanced anabolic metabolism in both mouse and human cancers that rely on Myc hyperactivation.

To model the therapeutic potential of inhibition of PRPS2 on in vivo Myc-driven tumor development, Eμ-Myc/+ fetal liver hematopoietic stem cells (HSCs) were infected with lentivirus expressing a doxycycline-inducible PRPS2 shRNA followed by transplantation of these cells into lethally-irradiated wild-type mice.

Figure 8E:
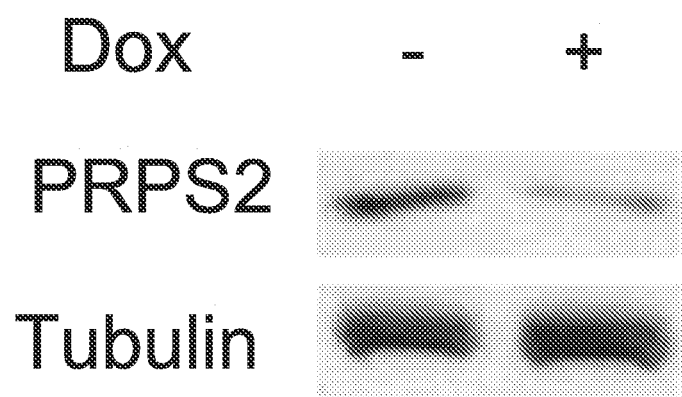
Figure 8F:
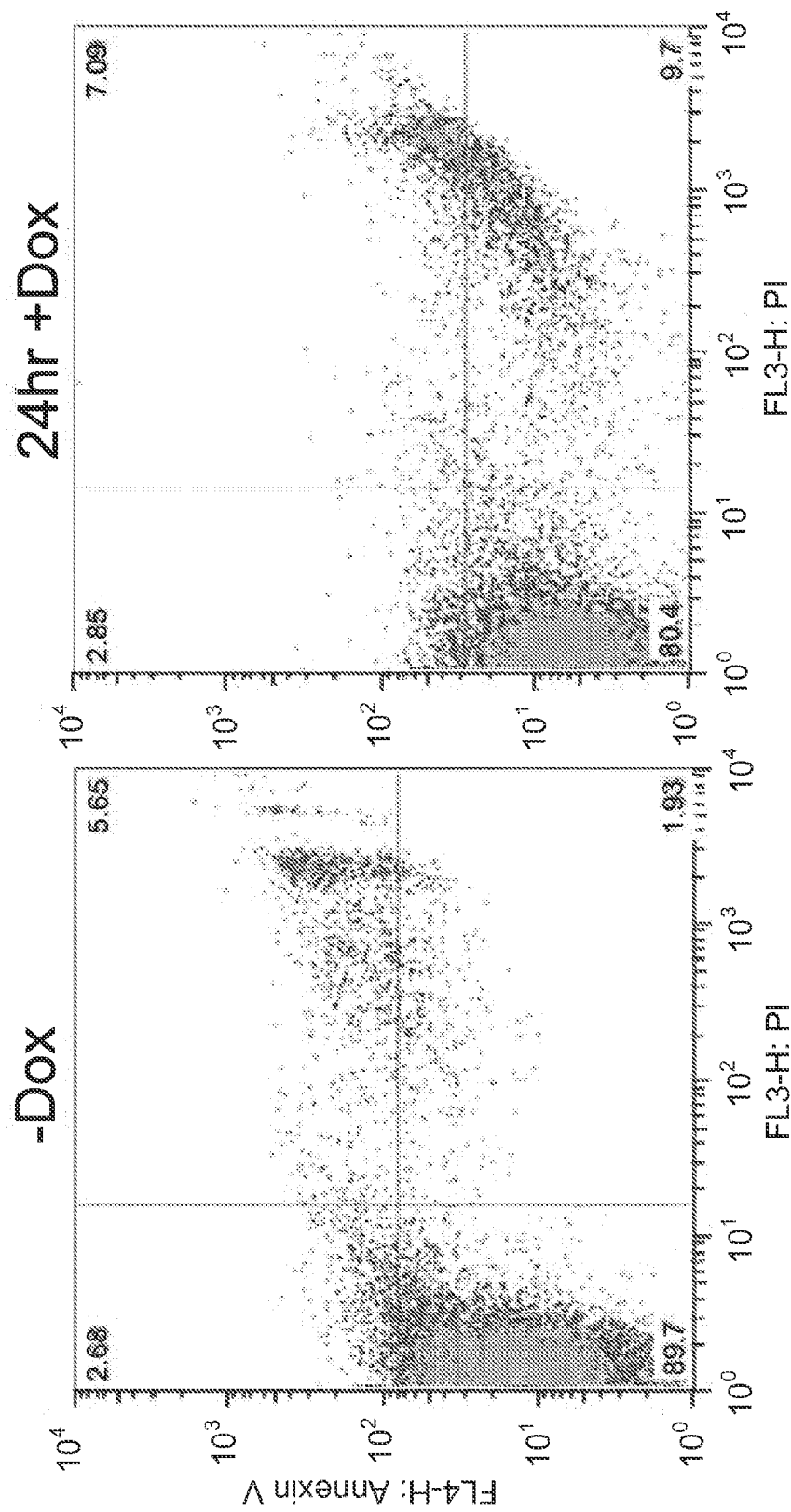
Figure 8G:
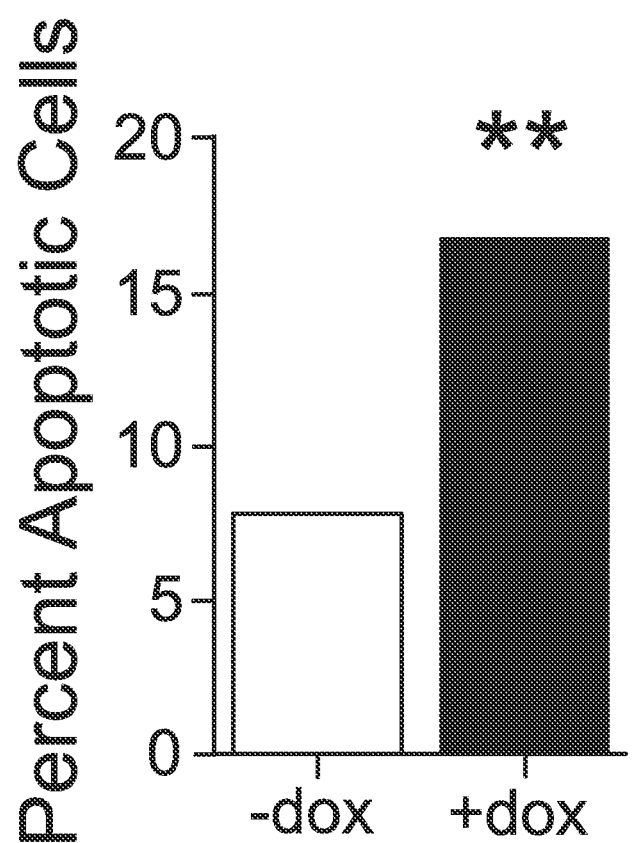
Figure 8I:
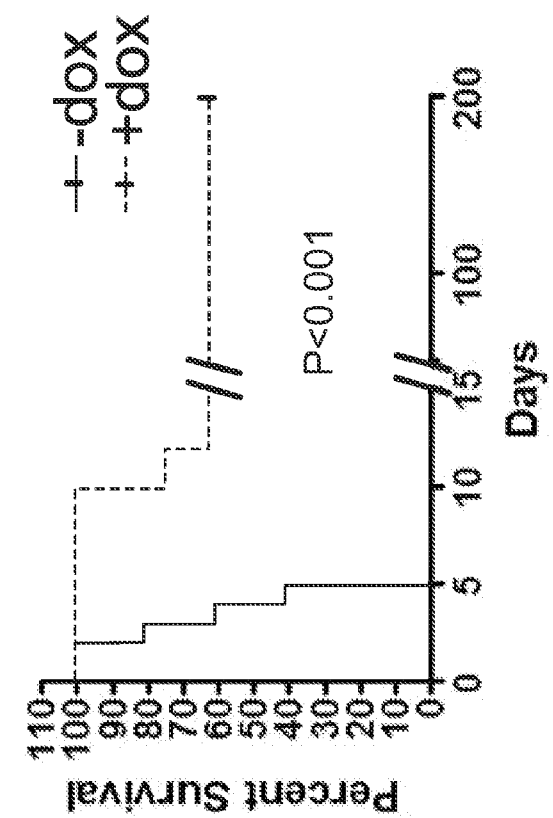
Figure 8H:
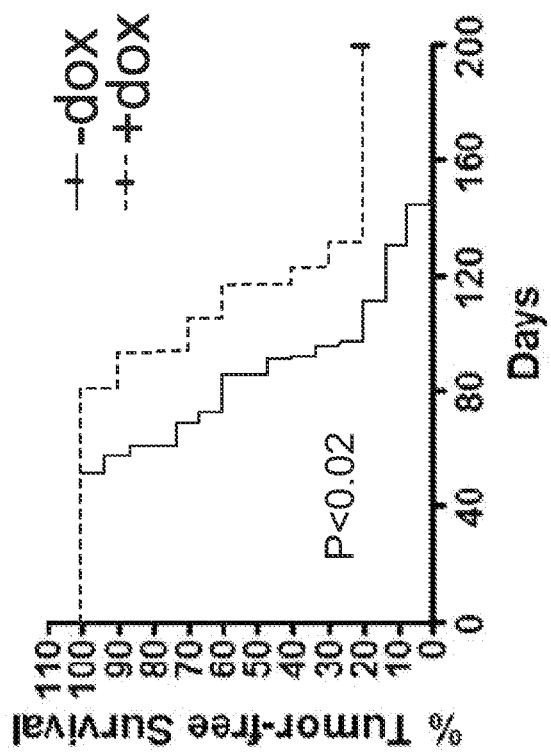
Figure 9:
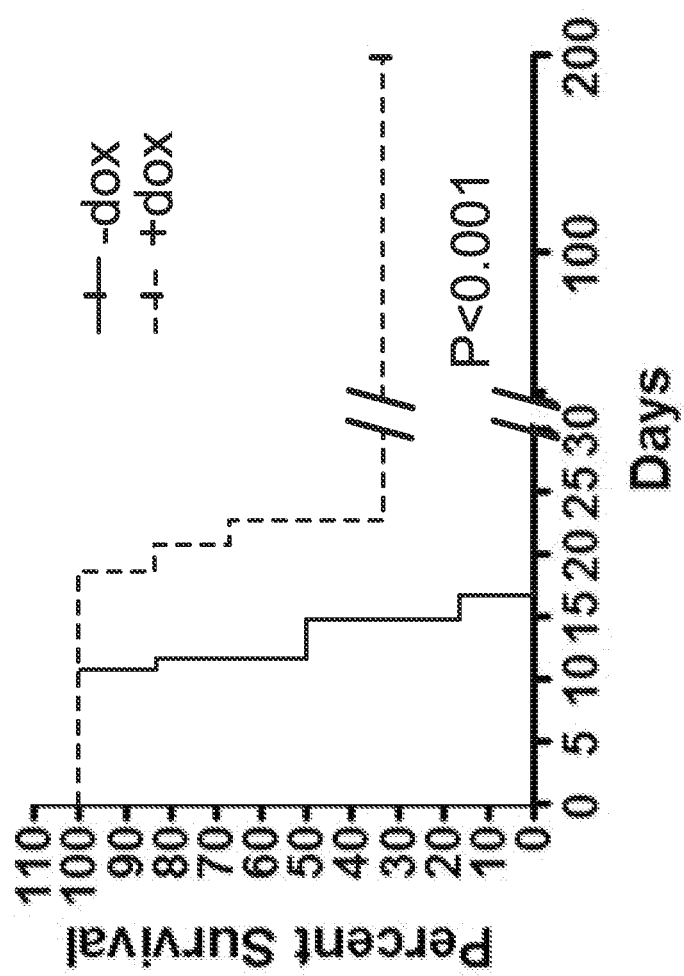
FIG. 9. PRPS2 expression is required for Myc-driven tumor progression. (A) Survival curves of Eμ-Myc/+ tumor transplanted mice. Cells were infected with retroviruses encoding constitutive GFP and doxycycline-inducible Prps2 shRNA hairpin and subsequently transplanted via tail vein to syngeneic animals. Upon engraftment, mice were dosed with vehicle (−dox) or 2 mg/mL doxycycline (+dox) in their drinking water.

To test the efficacy of doxycycline-induced shRNA knockdown of PRPS2 doxycycline was injected intraperitoneally into mice successfully engrafted with lentivirus-transduced Eµ-Myc/+HSCs. Twenty-four hours post-doxycycline administration, splenic B cells were isolated followed by Western blot analysis that revealed successful knockdown of PRPS2 (FIG. 8E) and a significant increase in apoptosis in Eµ-Myc/+ B cells from mice treated with doxycycline relative to the control (FIGS. 8F and 8G). Notably, mice induced to express shRNA directed toward Prps2 show a significant delay in Myc-driven tumor onset (FIG. 8H). To next assess the therapeutic efficacy of PRPS2 loss of function in already established Myc-driven lymphomas, tumor cells derived from two separate Eµ-Myc/+ mice were infected with GFP-expressing doxycycline-inducible Prps2 shRNA retroviruses and subsequently transplanted the infected cells into syngeneic mice. After tumor formation, Prps2 shRNA expression was induced and tumor progression was monitored (FIG. 8I and FIG. 9). A strong impairment in tumor progression upon knockdown of Prps2 was observed, and remarkably, at least 30% of these mice between the two experiments displayed complete tumor regression and survival beyond 7 months of age revealing a critical oncogenic role of PRPS2. Taken together, these results suggest that PRPS2 is a therapeutic target for in vivo inhibition of Myc-driven lymphomagenesis.

Figure 10A:
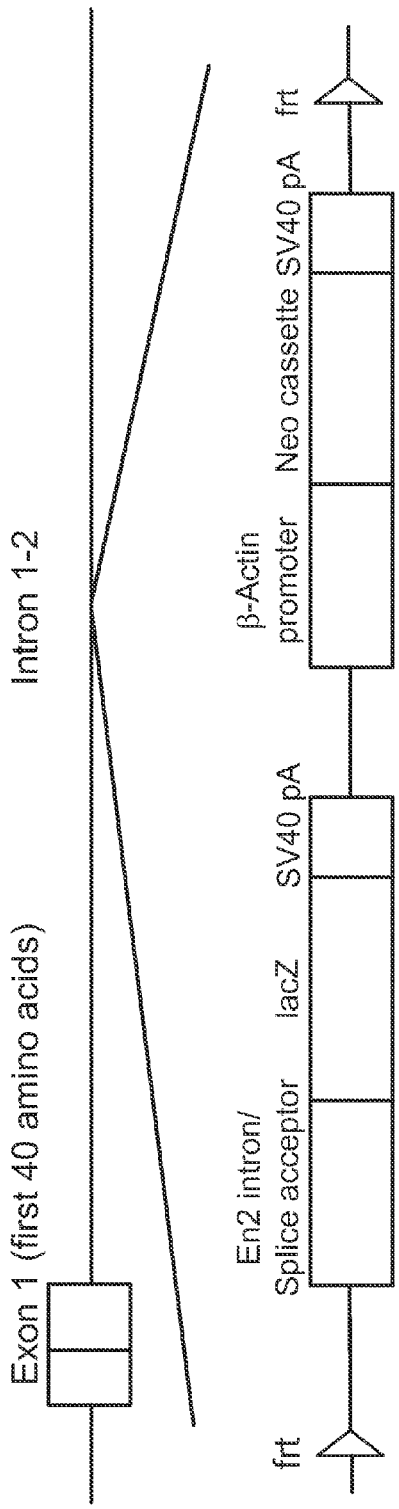
FIG. 10. Prps2$^{null}$ mice design and validation. (A) Schematic depicting Prps2$^{null}$ targeting vector in genomic context of the Prps2 gene. (B) Western blot using indicated antibodies of embryonic stem cell lysates from wild-type (WT) or Prps2$^{null}$ cells. (C) qRT-PCR analysis of mRNA levels of Prps1 or Prps2 in indicated tissues from WT or Prps2$^{null}$ mice. Data are expressed as relative to Rplp0 expression and then normalized to WT tissue. N=3, error bars represent standard deviation. (D) Prps1 (white bars) and Prps2 (black bars) mRNA abundance was quantified by qRT-PCR performed on tissues indicated from WT mice. Data are expressed as relative values using Rplp0 as a standard. N=3, error bars represent standard deviation.
Figure 10B:
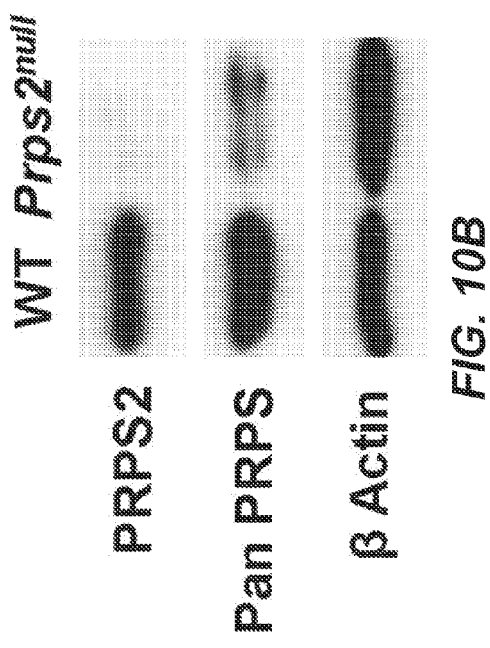
Figure 10C:
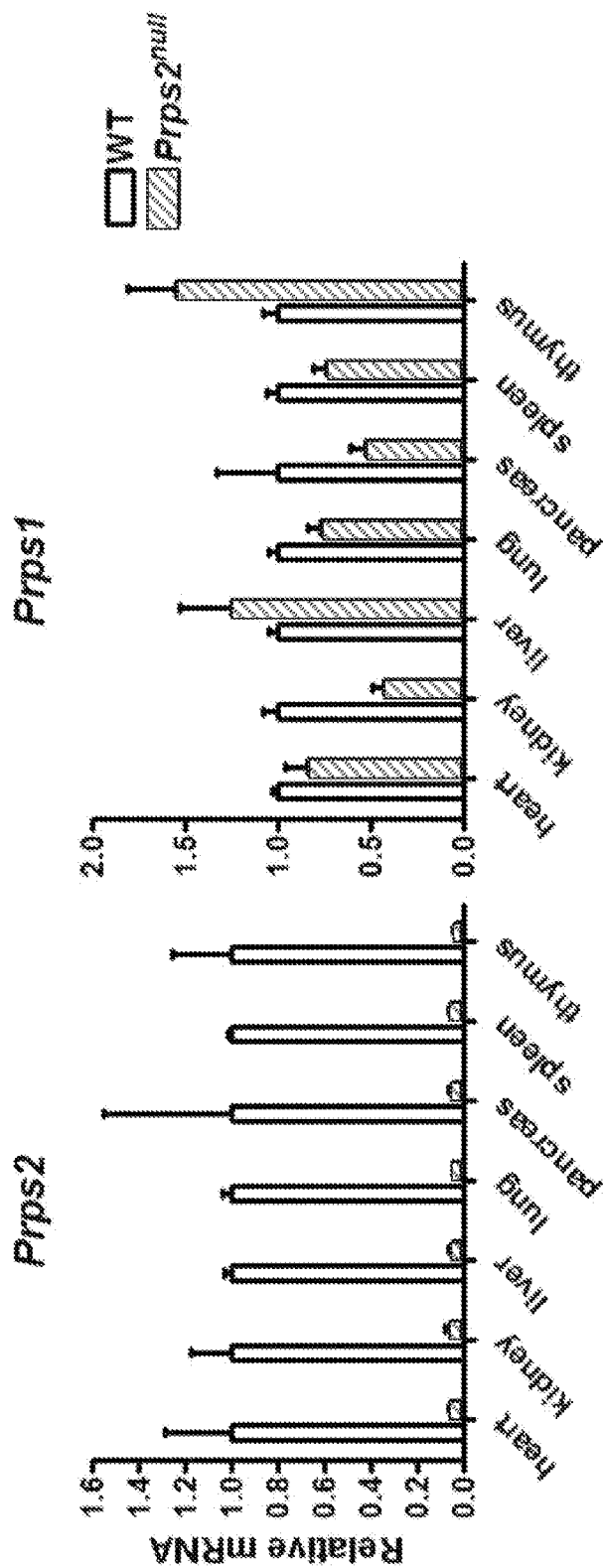
Figure 10D:
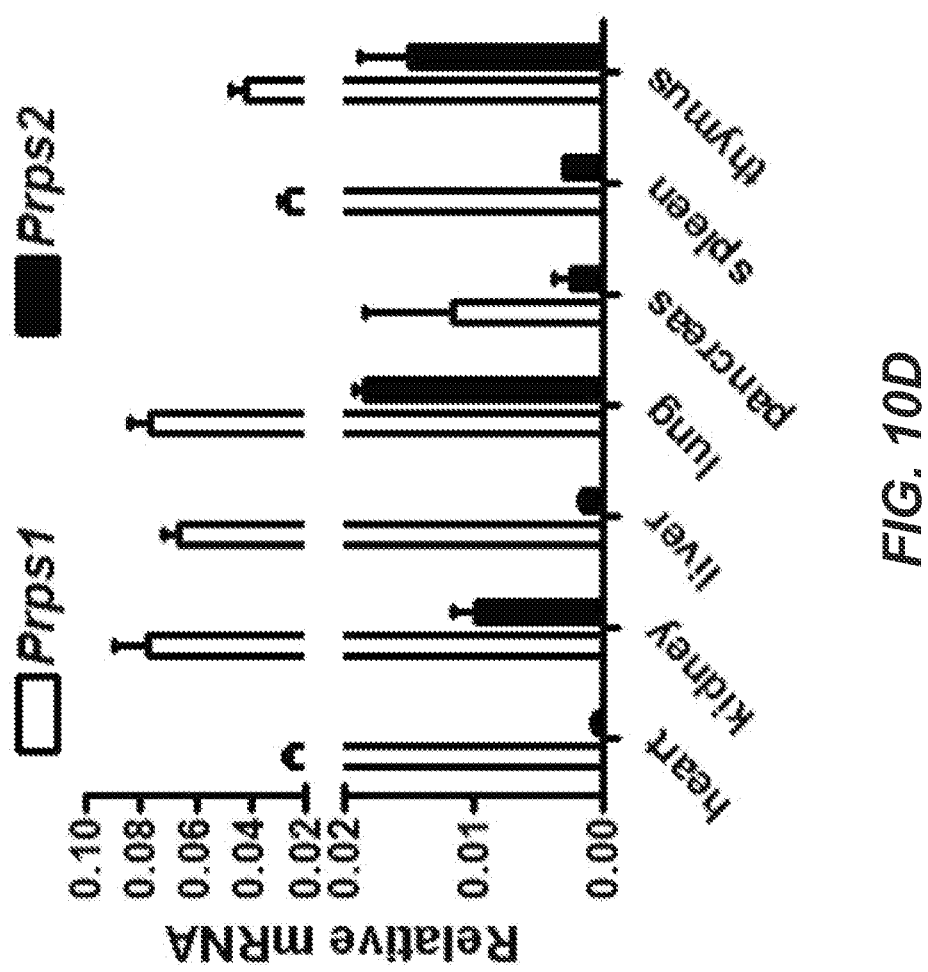

Generation of a Prps2 Knockout Mouse Reveals that PRPS2 is Normally Dispensable for Cell Viability and Organismal Physiology, but is Critically Required for Myc-Driven Lymphomagenesis in Both Mice and Humans An outstanding question is whether PRPS2 is normally essential for cell and organismal physiology in vivo. As PRPS2 shares approximately 95% amino acid identity with the PRPS1 isoform (Becker et al., 1990, *Genomics* 8:555-561), it remains unknown whether cancer cells have evolved a mechanism to promote cell survival through only one of the two PRPS isoforms and thereby illuminating a synthetic lethal interaction specific to cancer cells. To address this outstanding question, the first Prps2 knockout mouse was generated (FIG. 10A). Strikingly, mice homozygous null for the Prps2 gene (Prps2$^{null}$) are viable and fertile and display no gross phenotypic abnormalities despite lacking Prps2 mRNA and protein expression (FIGS. 10B and 10C). Notably, there was no compensatory upregulation of Prps1 mRNA levels in tissues from Prps2$^{null}$ mice, suggesting that normal expression levels and enzymative activity of PRPS1 are sufficient to maintain metabolic homeostasis (FIG. 10C). As PRPP is only produced by PRPS enzymes, these findings are consistent with the continued activity of the PRPS1 isozyme, whose mRNA is interestingly normally found expressed at higher levels than Prps2 in all tissues that were surveyed (FIG. 10B and FIG. 10D).

Figure 11A:
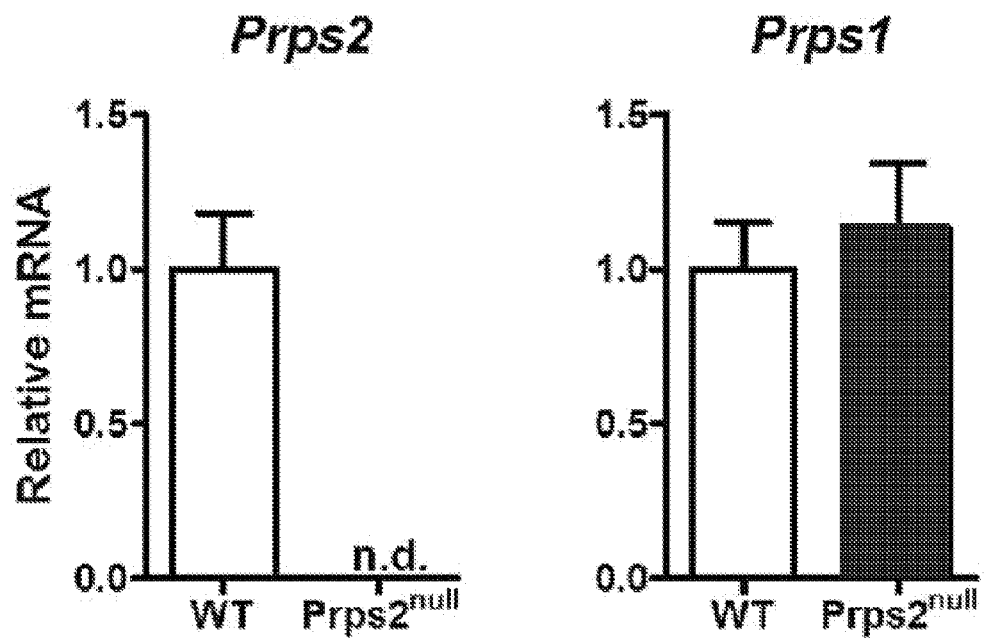
FIG. 11. Prps2$^{null}$ Spleens and B Cells are Indistinguishable Phenotypically from Wild-type Counterparts. (A) RNA was isolated from purified B cells derived from wild-type (WT) or Prps2$^{null}$ mice and qRT-PCR was performed to measure Prps2 or Prps1 RNA levels relative to β-actin mRNA. N=3, error bars represent standard deviation. N.d.=not detected. (B) Western blot of B cell lysates from mice with indicated genotype using antibodies specified. (C) Spleen weights of 8 wk old WT or Prps2$^{null}$ mice. (D) Haematoxylin and Eosin stained tissue sections from WT or Prps2$^{null}$ spleens imaged at low magnification. (E) The percentage of splenic B220+ cells was assessed by FACS analysis performed using red-cell depleted splenocytes from WT and Prps2$^{null}$ mice. (F) Percent apoptosis was assessed by Annexin V staining of B220+ B cells derived from WT or Prps2$^{null}$ mice. N=3, error bars represent standard deviation.
Figure 11B:
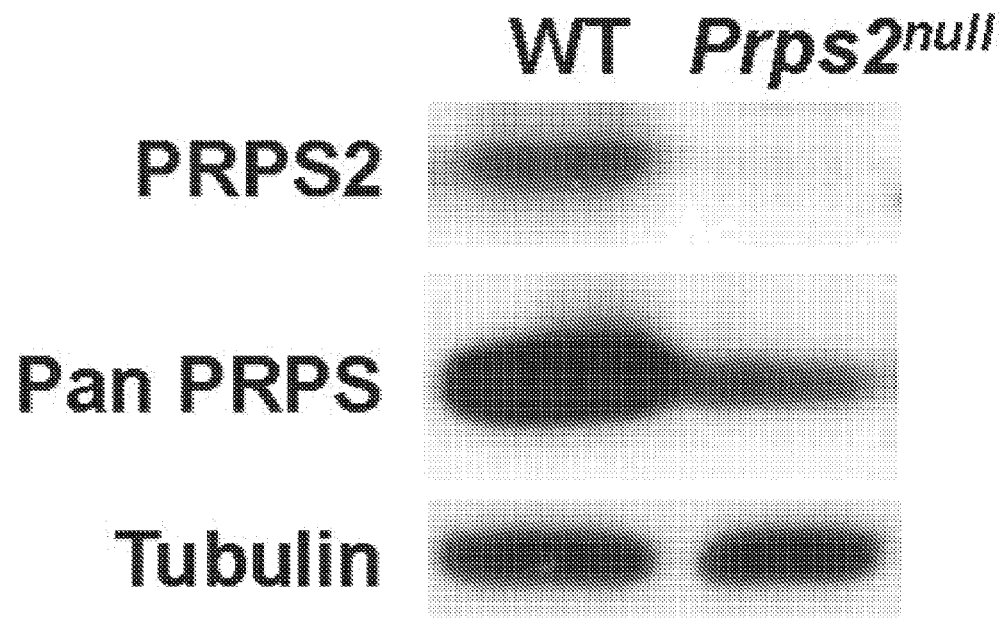
Figure 11C:
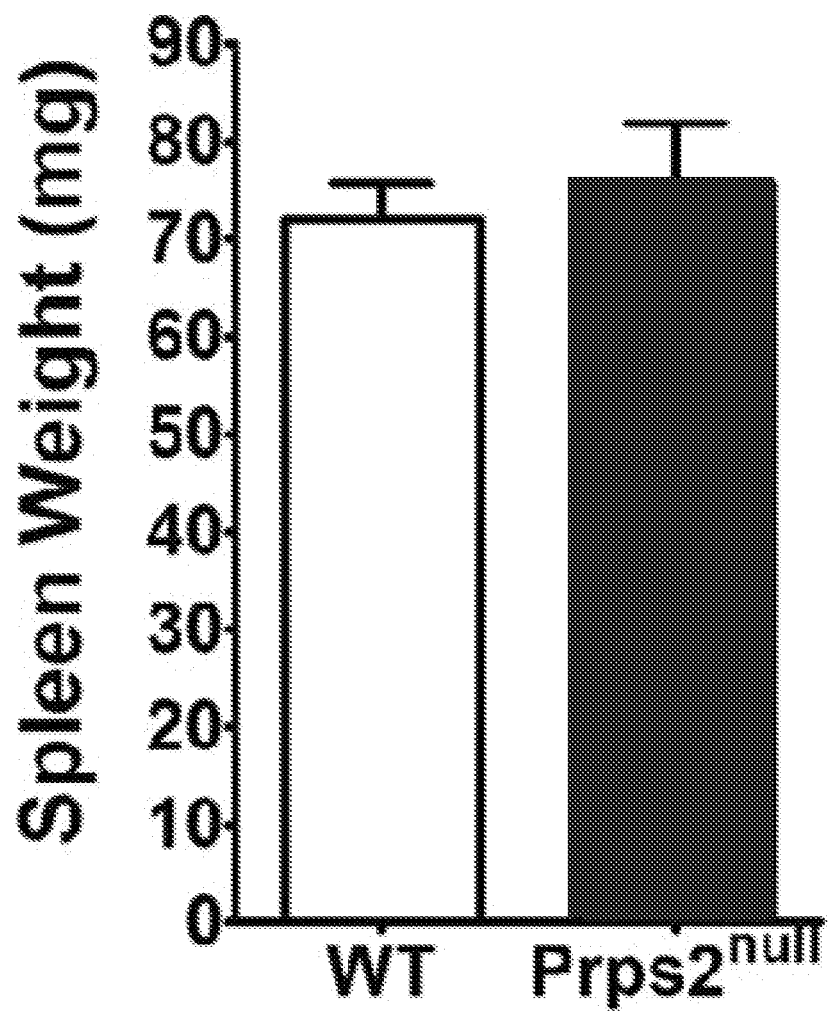
Figure 11D:
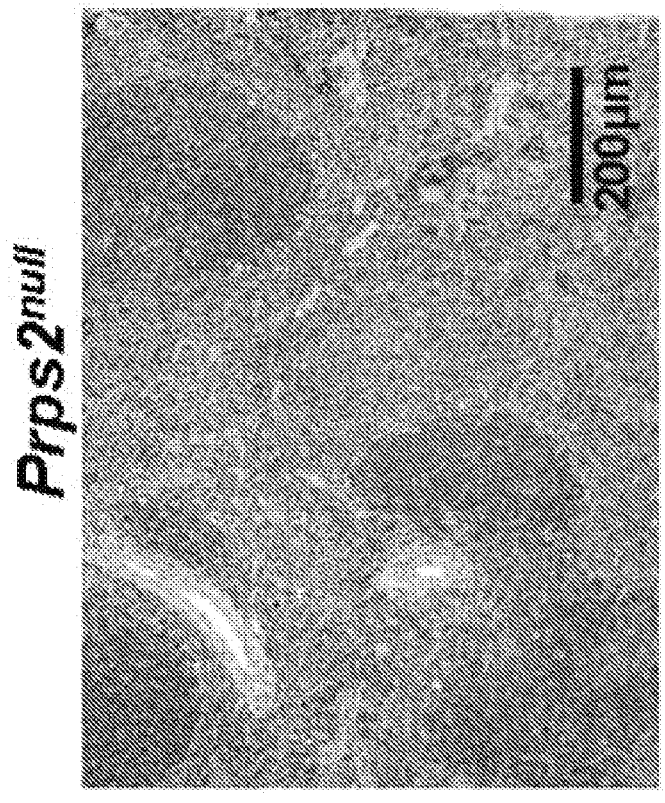
Figure 11D:
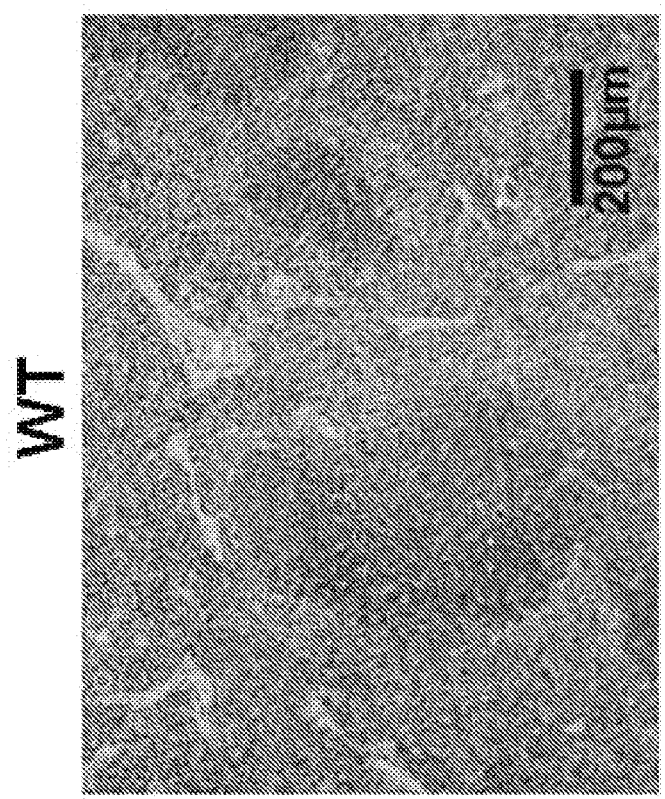
Figure 11E:
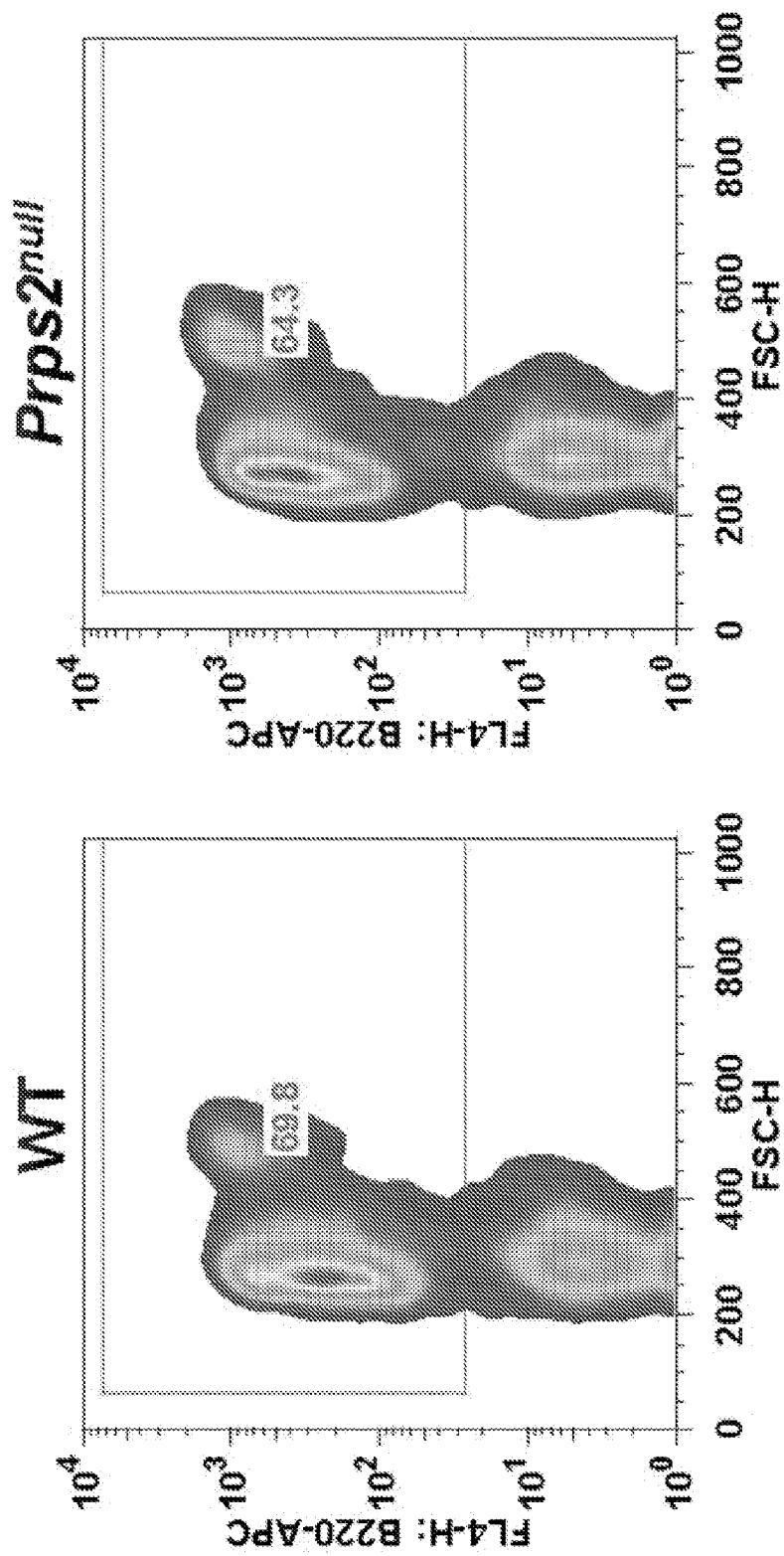
Figure 11F:
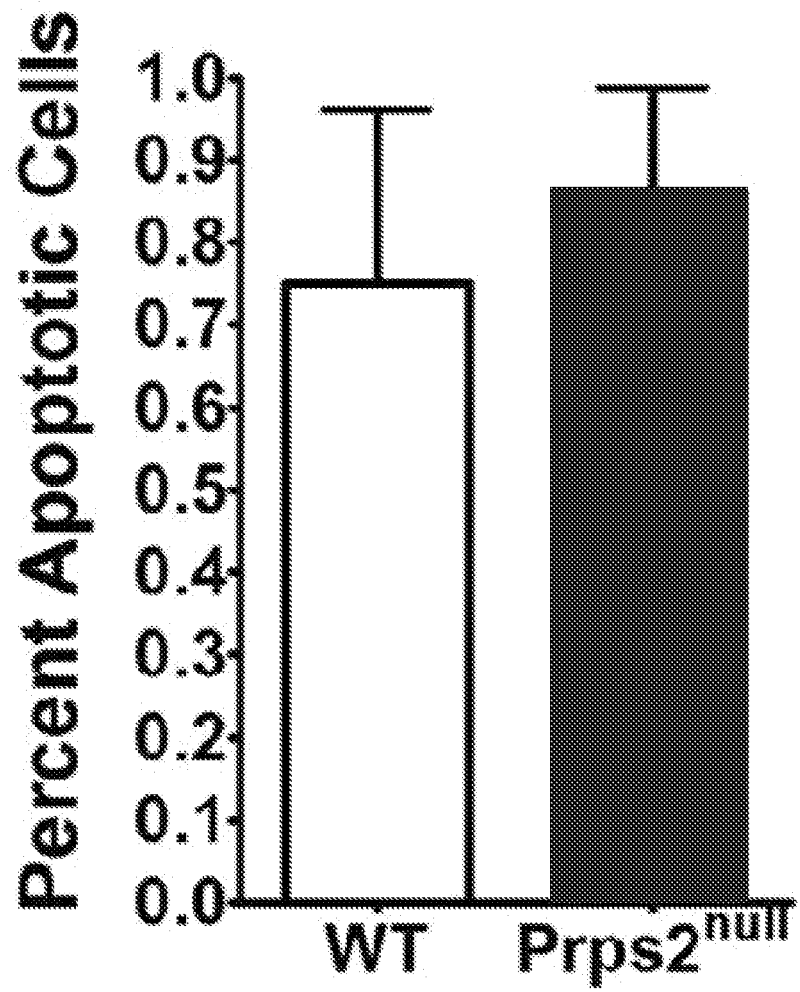
Figure 12A:
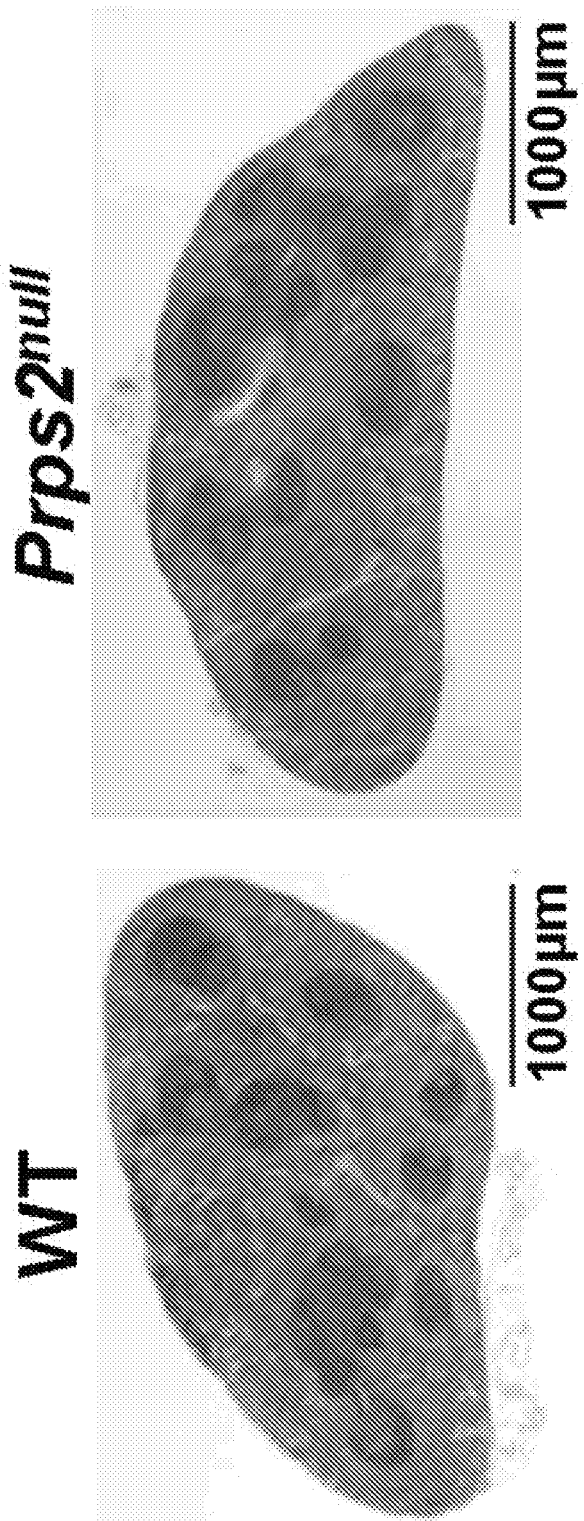
FIG. 12. Prps2$^{null}$ spleens and B cells are indistinguishable phenotypically from wild-type counterparts. (A) Haematoxylin and Eosin stained tissue sections from wild-type (WT) or Prps2$^{null}$ spleens. (B) Cell size of WT (red histogram) or Prps2$^{null}$ (blue histogram) B220+ B cells was assessed by FACS analysis. (C) Cell cycle distribution of splenic B cells purified from WT or Prps2$^{null}$ mice FIG. 13. Inhibition of PRPS2 is a Viable Therapeutic Strategy for Human Cancers. (A) Survival curves showing tumor-free survival between Eμ-Myc/+(N=24) and Eμ-Myc/+; Prps2$^{null}$ (N=17) male mice. Tick marks represent censored animals. (B) Apoptosis of human Myc-dependent lymphoma cell lines, Daudi and Raji, was assessed by Annexin V staining upon transduction with control or PRPS2 shRNA expressing retroviruses. Data in graph represents percent increase in Annexin V+GFP-labeled PRPS2 shRNA transduced cells relative to Annexin V+GFP-labeled control shRNA transduced cells. Error bars represent standard deviation, N=6, **P<0.01. (C) Proposed model for PRPS2 regulation of nucleotide (NT) production in normal and cancer cells. PRPS2 levels regulated via translational control act as a bottleneck in regulating the flow of Ribose-5-phosphate (R5P) from the pentose phosphate pathway to 5-phosphoribosyl 1-pyrophosphate (PRPP) used in NT production. Normal cells regulate PRPS2 levels via translational mechanisms to control NT production (left), whereas Myc-overexpressing cells with elevated translational capacity increase PRPS2 expression to produce more NTs for cancer cell survival (center). Interference with the Myc-dependent translational control of PRPS2 via siRNA or genetic strategies results in synthetic lethality in Myc-overexpressing cells (right).
Figure 12B:
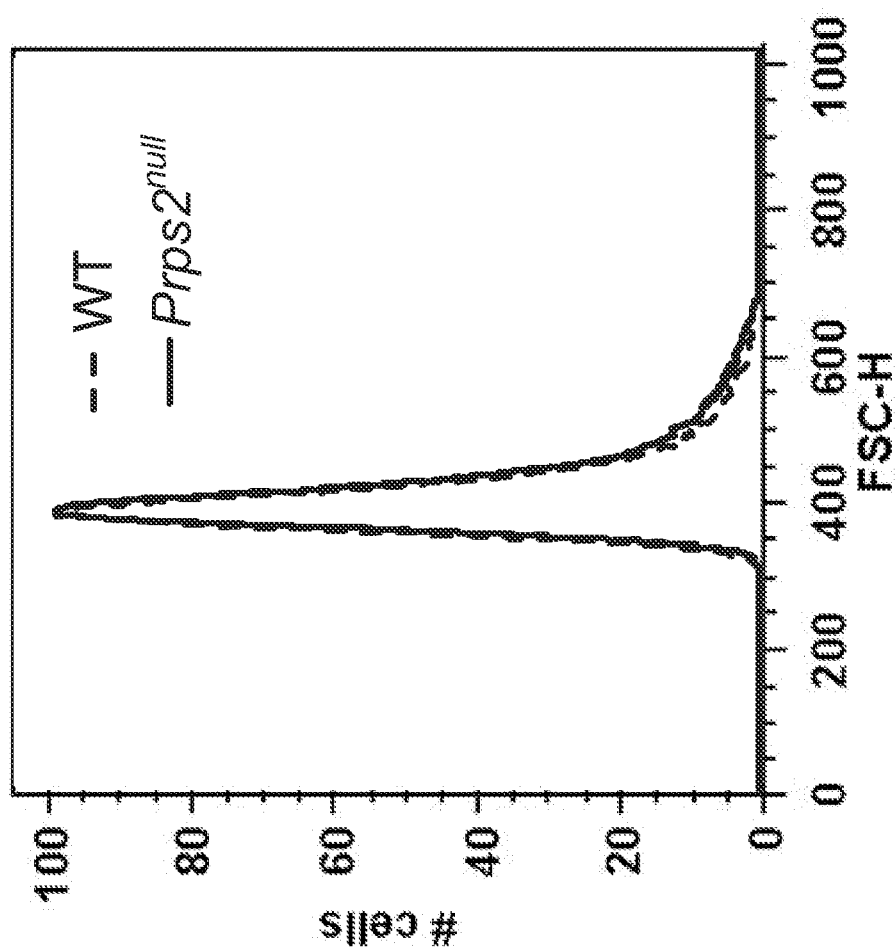
Figure 12C:
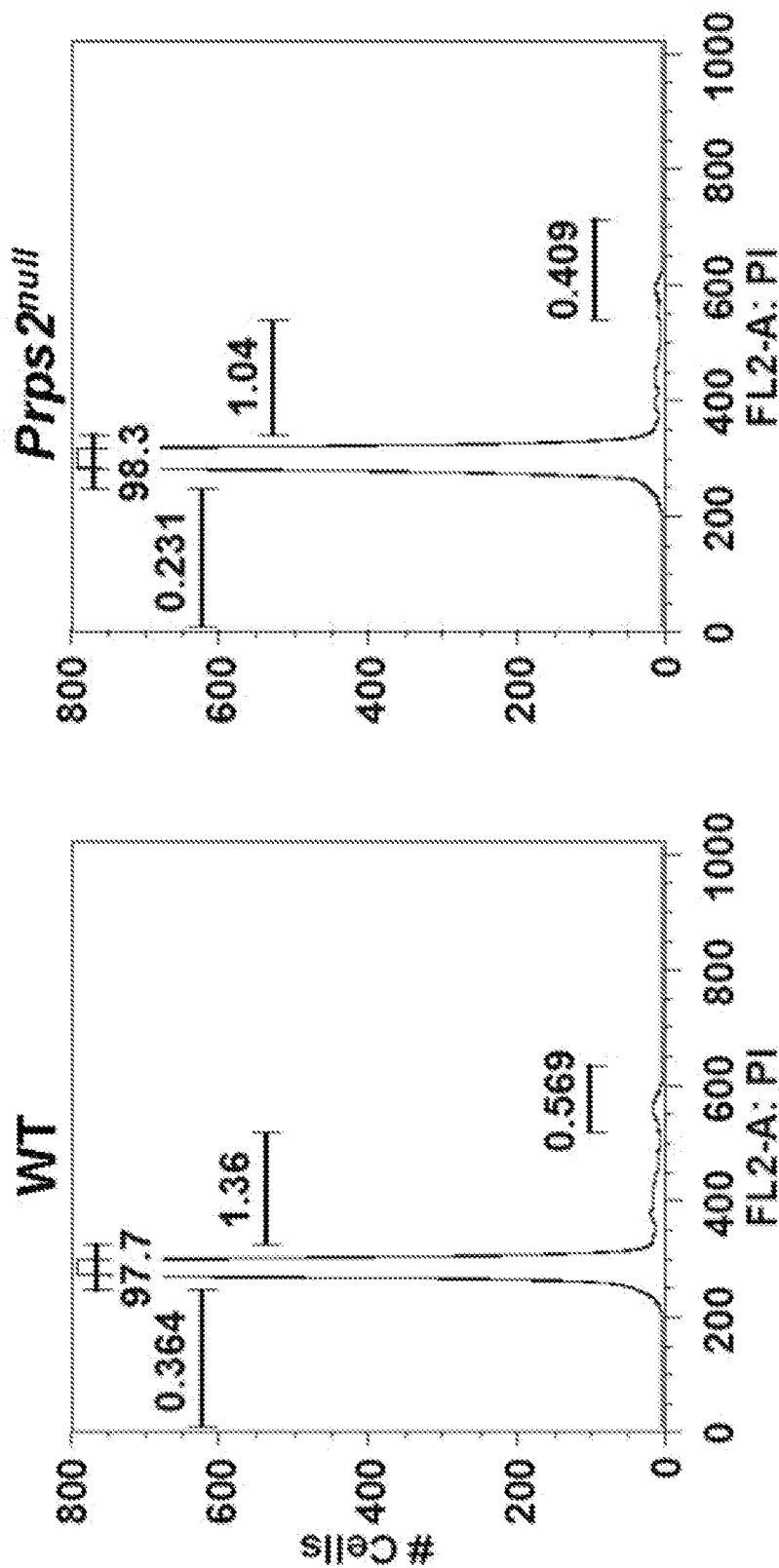

The function of PRPS2 in normal B-cell homeostasis as well as Myc-driven lymphomagenesis was next investigated. In Prps2$^{null}$ mice, Prps1 expression in splenic B cells was maintained at the same levels observed in wild type cells (FIGS. 11A and 11B). Complete loss of Prps2 expression did not alter spleen weight, tissue architecture or morphology (FIG. 11C, FIG. 11D, and FIG. 12). Moreover, the percent of B lymphocytes present in the spleen (FIG. 11E), as well as B cell size (FIG. 12B), cell cycle distribution (FIG. 12C), or cell viability (FIG. 11F) were not altered. Together, these results suggest that the activity of PRPS1 alone is sufficient to maintain the normal function of B lymphocytes and spleen development, whereas PRPS2 function is dispensable.

Figures 13A, 13B:
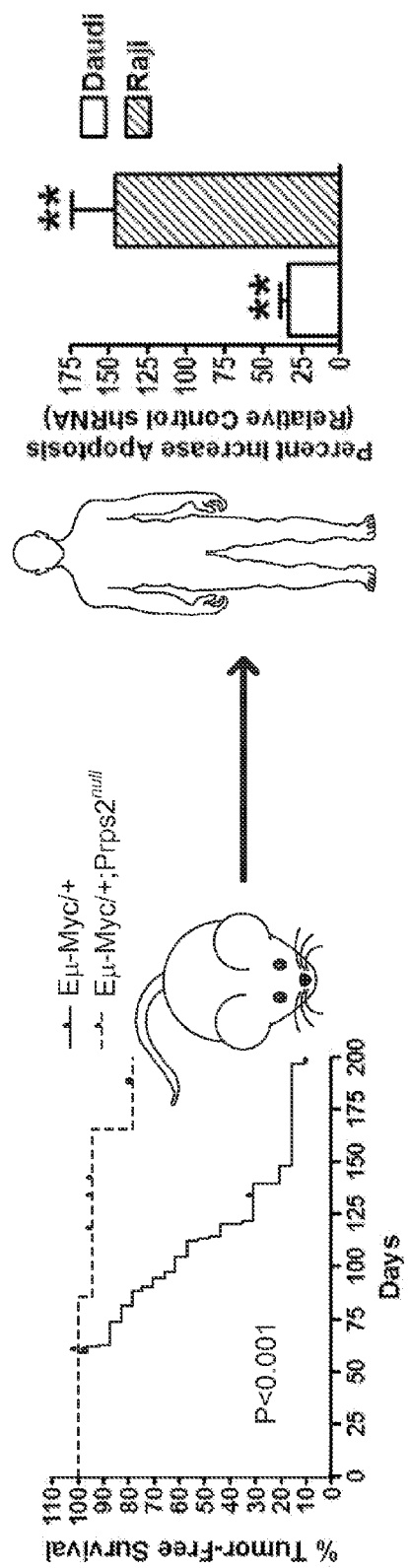

Prps2$^{null}$ mice was then employed to genetically address the requirement of PRPS2 activity in Myc-driven lymphomagenesis. Strikingly, Eµ-Myc/+; Prps2$^{null}$ mice displayed a remarkable delay in tumor initiation compare to their Eµ-Myc/+ littermates (FIG. 13A). In fact, while 50% (12/24) of Eµ-Myc/+ mice developed tumors by 115 days, only 5.9% (1/17) of Eµ-Myc/+; Prps2$^{null}$ mice developed tumors by this same age. Taken together, the results of these studies support the model that presence of PRPS2 activity is not required for normal B lymphocyte function, but it is essential for tumorigenesis.

Figure 13C:
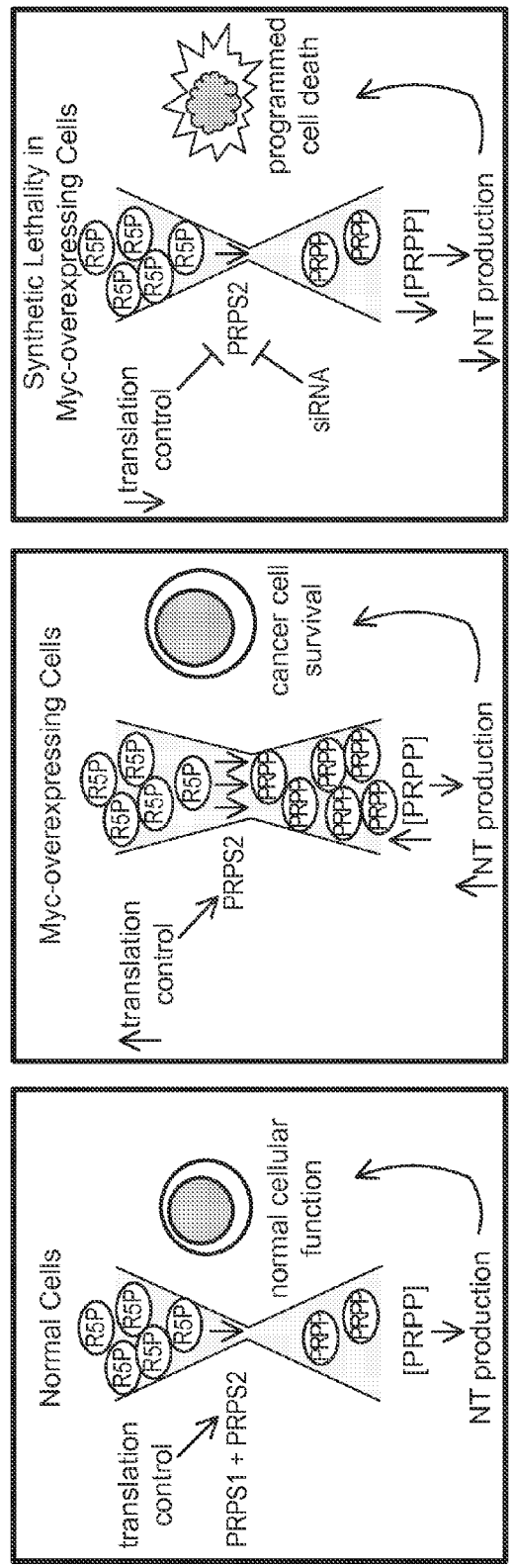

Altogether, these findings point to a model whereby translational regulation of PRPS2 couples protein synthesis to metabolism and directly acts as a molecular rheostat for the nucleotide biosynthesis pathway in cancer cells, controlling the flow of ribose-5-phosphate from the pentose phosphate pathway into the nucleotide biosynthetic precursor PRPP (FIG. 13C). Therapeutic strategies that interfere with this Myc-dependent translational control or direct inhibition of PRPS2 expression create a 'bottleneck' between the pentose phosphate pathway and nucleotide precursors to decrease the nucleotide production that is specifically required for cancer but not normal cell survival, and consequently, tumor initiation and progression.

Discussion

The Role of Translational Control in Cellular Metabolism

These results demonstrate that protein synthesis is coupled to metabolism and is actively required for the metabolic reprogramming of cancer cells. Therefore, these findings highlight a novel mode of regulating the cancer metabolome. This contrasts with other common mechanisms of metabolic re-programming performed by oncogenic pathways including transcriptional control or phosphorylation-dependent activation of metabolic enzymes, such as phosphorylation of carbmoyl-phosphate synthetase 2, aspartate transcarbamoylase, dihydroorotase (CAD) resulting in increased pyrimidine nucleotide biosynthesis by mTOR (Ben-Sahra et al., 2013, Science 339:1323-1328).

It has been shown that translational control, rather than affecting gene expression of an entire metabolic pathway, unexpectedly regulates the expression of a key metabolic enzyme to exert influence over the cancer metabolome. This level of specificity can serve dual functions in cells. First, selective regulation of only one rate-limiting enzyme of the pathway bypasses the need for an energy-consuming response that requires coordinated transcription, mRNA processing and nuclear export prior to ribosome recruitment and translation. Second, the ability to translationally up- or down-regulate already existing mRNAs that encode enzymes capable of controlling metabolic flux ensures a quick phenotypic response to intracellular signals that directly integrate the protein synthesis demands of cancer cells. By coupling the cellular processes of protein biosynthesis and nucleotide metabolism, cancer cells have evolved a very rapid and integrated response that facilitates uncontrolled cancer cell growth and survival.

Elevated nucleotide concentrations are a critical feature of many cancers that contribute to tumorigenesis in a variety of ways. An increased pool of RNA nucleotides is utilized by cancer cells for incorporation into rRNA and tRNA to generate increased numbers of ribosomes (Ben-Sahra et al., 2013, *Science* 339:1323-1328). Additionally, a direct role for elevated nucleotide production has been demonstrated in the bypass of oncogene-induced sensescence (Aird et al., 2013, *Cell Reports* 3:1252-1265). Sufficient pools of deoxyribonucleotides are also required to maintain DNA fidelity during replication (Bester et al., 2011, *Cell* 145:435-446). Interestingly, a non-cell autonomous role for tumor cell-activated platelet-derived secreted nucleotides has been recently found to promote metastasis suggesting that alternative means by which nucleotides contribute to cancer may have yet to be discovered (Schumacher et al., 2013, *Cancer Cell* 24:130-137). Thereby the ability of key oncogenes such as Myc to post-transcriptionally regulate the expression of PRPS2, a single rate-limiting enzyme within the nucleotide biosynthetic pathway, reveals a significant vulnerability to cancer cell homeostasis.

Interestingly, the mechanistic basis for translational regulation of Prps2 occurs through a sequence-specific pyrimidine-rich translational element contained within the 5'UTR of the mRNA. It was demonstrated that translation of Prps2, through this element, is dictated by eIF4E, which in addition to direct activation by Myc, also serves as a hub for growth factor signaling. Pro-growth signals emanating from the Ras, phosphoinositol-3 kinase (PI3K), and Myc pathways activate eIF4E through different mechanisms to facilitate translation of specific eIF4E-responsive mRNAs (Topisirovic and Sonenberg, 2011, *Cold Spring Harb. Symp. Quant. Biol.* 76:355-367). Therefore, the identification of PRPS2 as a key, translationally regulated enzyme may have broad implications for metabolic control in many cancer types.

Oncogenic Conversion of Glucose Metabolic Enzymes

Recent studies have highlighted novel ways in which cancer cells utilize distinct isoforms of enzymes within the glucose metabolic pathway that possess tailored activities promoting the "Warburg Effect" (Vander Heiden et al., 2009, *Science* 324:1029-1033). These "oncozymes" are normally either expressed at low levels or in a small subset of cells or tissues, and their expression and activity are co-opted upon oncogenic transformation. The ultimate goal of this metabolic restructuring is to channel glucose metabolites from catabolic to anabolic pathways in order to support cancer cell growth and proliferation. Oncogenes hijack this metabolic remodeling via several modes of action. For example, oncogenic activation of the glycolytic enzyme pyruvate kinase isoform M2 occurs through a mechanism that relies on alternative splicing, and its expression restrains the flow of glycolytic metabolites through catabolic pathways so that they may be utilized for macromolecular synthesis (Clower et al., 2010, *Proc. Natl. Acad. Sci.* 107:1894-1899). This work suggests that PRPS2 falls into this same category of enzymes whose activation in cancer cells specifically directs the flow of glucose metabolites into anabolic pathways that support growth and proliferation.

PRPS2 shares approximately 95% amino acid identity with the PRPS1 isoform (Becker et al., 1990, *Genomics* 8:555-561). However, distinguishing features of the enzyme are present that may provide intriguing insight as to why PRPS2 may be favored to promote nucleotide biosynthesis in oncogenic cells. First, PRPS2 has been demonstrated to be more resistant to the allosteric feedback inhibition by nucleotide biosynthetic pathway by products ADP and GDP (Nosal et al., 1993, *J. Biol. Chem.* 268:10168-10175). Notably, only Prps2 but not Prps1 contains the PRTE cis-acting translational element within its 5' UTR. These enzymatic properties of the different PRPS isoforms may be of particular interest with regards to therapeutic design as they suggest a biochemical basis for the development of specific inhibitors to selectively inhibit PRPS2.

PRPS2 as a Therapeutic Target

PRPS2 has been identified as a relevant therapeutic target downstream of the Myc and mTOR/4EBP pathways important for cancer cell survival. PRPS2 is one of two isoforms of the phosphoribosyl pyrophosphate synthetase enzyme, which is expressed in most tissues. Because of the presence of PRPS1 throughout most tissues, a large therapeutic window may exist for drugs that selectively target PRPS2.

Previous studies by the inventors have established the essential role of deregulated protein synthesis in Myc-driven cancers. However, the cellular processes downstream of Myc-induced protein synthesis that are responsible for promoting tumorigenesis were previously largely unknown. Here, it has been shown that Myc-overexpressing cells display altered metabolism (more specifically, increased purine biosynthesis) in response to increased protein synthesis. We show that one mechanism by which cells can achieve increased purine biosynthesis is through the cap-dependent translational control of PRPS2. Taken together, our results elucidate a mechanism illustrating crosstalk between the protein synthesis and nucleotide biosynthesis pathways and identify PRPS2 as a translationally-regulated therapeutic target for cancers in which Myc is hyperactivated.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of selectively killing a cell, wherein the cell expresses Myc, the method comprising contacting the cell with an inhibitory RNA that inhibits phospho-ribosyl pyrophophosphate synthetase 2 (PRPS2) in an amount sufficient to induce apoptosis, thereby selectively killing the cell.

2. The method of claim 1, wherein the cell is a neoplastic cell.

3. The method of claim 2, wherein the neoplastic cell is a cancer cell and wherein the cancer is associated with Myc hyperactivation.

4. The method of claim 1 wherein the inhibitory RNA directly inhibits PRPS2.

5. The method of claim 1, wherein the inhibitory RNA does not inhibit phospho-ribosyl pyrophophosphate synthetase 1 (PRPS1).

6. The method of claim 1, wherein the inhibitory RNA targets at least a portion of a pyrimidine-rich translational element (PRTE) or a 5' terminal oligopyrimidine (5' TOP) sequence within the 5' untranslated region (5' UTR) of PRPS2.

7. The method of claim 1, wherein the inhibitory RNA is an shRNA, siRNA, or miRNA.

8. A method of treating a neoplastic disease in a subject, the method comprising: administering to the subject an inhibitory RNA that inhibits phospho-ribosyl pyrophophosphate synthetase 2 (PRPS2) in an amount sufficient to induce apoptosis, wherein the inhibitory RNA selectively kills neoplastic cells in the subject and wherein the neoplastic cells express Myc, thereby treating the neoplastic disease.

9. The method of claim 8, wherein the neoplastic disease is a cancer.

10. The method of claim 8, wherein the cancer is associated with Myc hyperactivation.

11. The method of claim 8, wherein the subject is a human.

12. The method of claim 8, wherein the inhibitory RNA is an shRNA, siRNA, or miRNA.

13. The method of claim 8, wherein the inhibitory RNA directly inhibits PRPS2.

14. The method of claim 8, wherein the inhibitory RNA does not inhibit phospho-ribosyl pyrophophosphate synthetase 1 (PRPS1).

15. The method of claim 8, wherein the inhibitory RNA targets at least a portion of a pyrimidine-rich translational element (PRTE) or a 5' terminal oligopyrimidine (5' TOP) sequence within the 5' untranslated region (5' UTR) of PRPS2.

16. The method of claim 6, wherein the inhibitory RNA targets at least a portion of SEQ ID NOs: 3, 37, 38, 39 or 40.

17. The method of claim 8, wherein the inhibitory RNA targets at least a portion of SEQ ID NOs: 3, 37, 38, 39 or 40.

18. The method of claim 9, wherein the cancer is bladder cancer, breast cancer, colon cancer, gastric cancer, hepatic cancer, ovarian cancer, prostate cancer, lung cancer, melanoma, neuroblastoma, or lymphoma.

19. The method of claim 18, wherein the cancer is lymphoma.

* * * * *